United States Patent [19]
Albertsen et al.

[11] Patent Number: 5,352,775
[45] Date of Patent: Oct. 4, 1994

[54] APC GENE AND NUCLEIC ACID PROBES DERIVED THEREFROM

[75] Inventors: Hans Albertsen, Salt Lake City, Utah; Rakesh Anand, Cheshire, England; Mary Carlson; Joanna Groden, both of Salt Lake City, Utah; Philip J. Hedge, Cheshire, England; Geoff Joslyn, Salt Lake City, Utah; Kenneth Kinzler, Baltimore, Md.; Alexander F. Markham, Cheshire, England; Yusuke Nakamura, Tokyo, Japan; Andrew Thliveris, Salt Lake City, Utah; Bert Vogelstein, Baltimore, Md.; Raymond L. White, Salt Lake City, Utah

[73] Assignees: The Johns Hopkins Univ., Baltimore, Md.; The Univ. of Utah, Salt Lake City, Utah; Imperial Chemical Industries, London, England; Cancer Institute, Tokyo, Japan

[21] Appl. No.: 741,940

[22] Filed: Aug. 8, 1991

[30] Foreign Application Priority Data

| Jan. 16, 1991 [GB] | United Kingdom | 9100962 |
| Jan. 16, 1991 [GB] | United Kingdom | 9100963 |
| Jan. 16, 1991 [GB] | United Kingdom | 9100974 |
| Jan. 16, 1991 [GB] | United Kingdom | 9100975 |

[51] Int. Cl.⁵ .................. C07H 21/00; C12Q 1/68
[52] U.S. Cl. .................. 536/23.1; 935/8; 935/9; 435/6
[58] Field of Search .......... 435/6, 810; 935/8, 78; 536/27

[56] References Cited

U.S. PATENT DOCUMENTS

5,098,823 3/1992 Bodmer et al.
5,137,806 8/1992 LeMaistre et al. .......... 435/6

FOREIGN PATENT DOCUMENTS

8901481 2/1989 PCT Int'l Appl.

OTHER PUBLICATIONS

Groden, et al., Cell, vol. 66, pp. 589–600, 1991.
Joslyn, et al., Cell, vol. 66, pp. 601–613, 1991.
Kinzler, et al., Science, vol. 253, pp. 661–665, 1991.
Nishisho, et al., Science, vol. 253, pp. 665–669, 1991.
Orita, et al., Genomics, vol. 5, pp. 874–879, 1989.
Stanbridge, et al., Science, vol. 247, pp. 12–13, 1990.
Bodmer et al. 1987 Nature 328:614.
Fearen et al 1990 Science 247:49.
Baker et al. 1989 Science 244:217.

*Primary Examiner*—Robert J. Hill, Jr.
*Assistant Examiner*—K. Cochrane Carlson
*Attorney, Agent, or Firm*—Banner, Birch, McKie & Beckett

[57] ABSTRACT

A human gene termed APC is disclosed. Methods and kits are provided for assessing mutations of the APC gene in human tissues and body samples. APC mutations are found in familial adenomatous polyposis patients as well as in sporadic colorectal cancer patients. APC is expressed in most normal tissues. These results suggest that APC is a tumor suppressor.

10 Claims, 48 Drawing Sheets

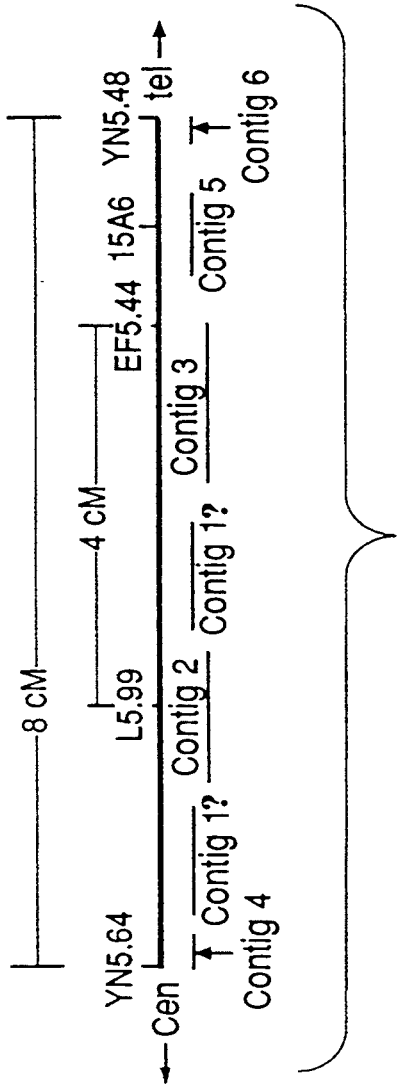
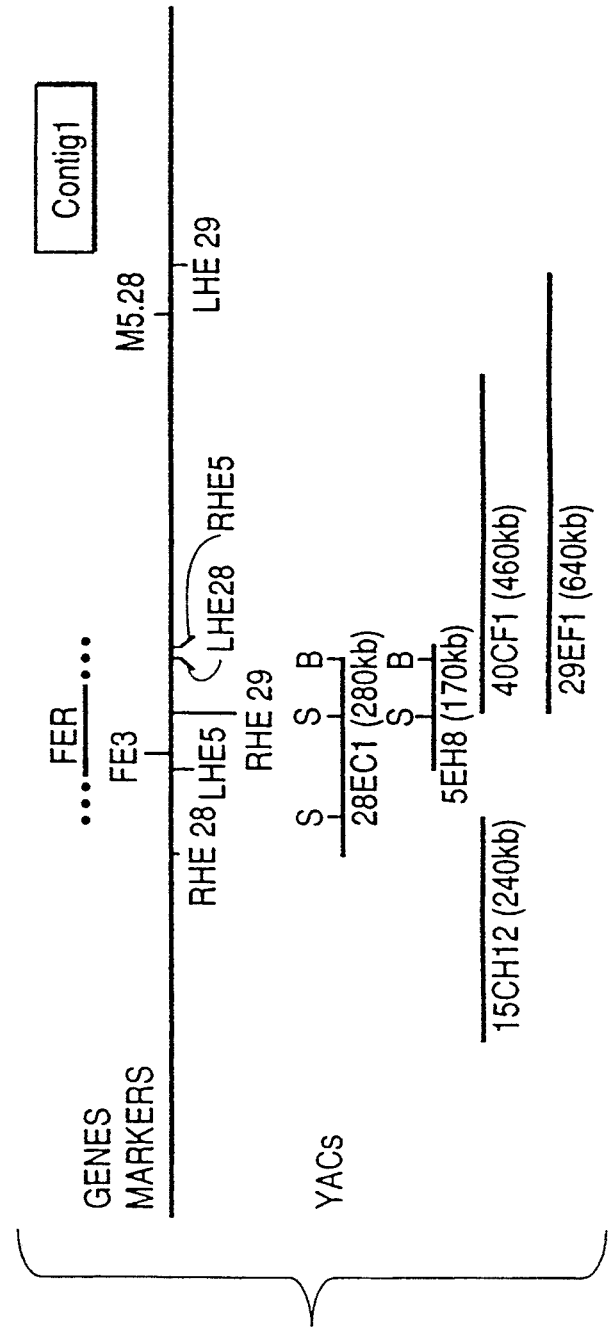
FIG. 1A
FIG. 1B-1

FIG. 2A

TB1 AMINO ACID SEQUENCE

| | | | | | |
|---|---|---|---|---|---|
| VAPVVVGSGR | APRHPAPAAM | HPRRPDGFDG | LGYRGGARDE | QGFGGAFPAR | SFSTGSDLGH | 60
| HVTPPDIPG | SRNLHWGEKS | PPYGVPTTST | PYEGPTEEPF | SSGGGGSVQG | QSSEQLNRFA | 120
| GFGIGLASLF | TENVLAHPCI | VLRRQCQVNY | HAQHYHLTPF | TVINIMYSFN | KTQGPRALWK | 180
| GMGSTFIVQG | VTLGAEGIIS | EFTPLPREVL | HKWSPKQIGE | HLLLKSLTYV | VAMPFYSASL | 240
| IETVQSEIIR | DNTGILECVK | EGIGRVIGMG | VPHSKRLLPL | LSLIFPTVLH | GVLHYIISSV | 300
| IQKFVLLILK | RKTYNSHLAE | STSPVQSMLD | AYFPELIANF | AASLCSDVIL | YPLETVLHRL | 360
| HIQGIRTIID | NTDLGYEVLP | INIQYEGMRD | CINTIRQEEG | VFGFYKGFGA | VIIQYTLHAA | 420
| VLQITKIIYS | TLLQ | | | | | 434

FIG. 2B

TB2 Amino Acid Sequence

```
ELRRFDRFLH EKNCHTDLLA KLEAKTGVNR SFIALGVIGL VALYLVFGYG ASLLCNLIGF   60
GYPAYISIKA IESPNKEDDT QWLTYWVYG VFSIAEFFSD IFLSWFPFYY ILKCGFLLWC  120
MAPSPSNGAE LLYKRIIRPF FLKHESQMDS VVKDLKDKAK ETADAITKEA KKATVNLLGE  180
EKKST                                                             185
```

FIG. 3A

```
MAAASYDQLL KQVEALKMEN SNLRQELEDN SNHLTKLETE ASNMKEVLKQ LQGSIEDEAM    60
ASSGQIDLLE RLKELNLDSS NFPGVKLRSK MSLRSYGSRE GSVSSRSGEC SPVPMGSFPR   120
RGFVNGSRES TGYLEELEKE RSLLLADLDK EEKEKDWYA  QLQNLTKRID SLLTENFSLQ   180
TDMTRRQLEY EARQIRVAME EQLGTCQDME KRAQRRIARI QQIEKDILRI RQLLQSQATE   240
AERSSQNKHE TGSHDAERQN EGQGVGEINM ATSGNGQGST TRMDHETASV LSSSSTHSAP   300
RRLTSHLGTK VEMVYSLLSM LGTHDKDDMS RTLLAMSSSQ DSCISMRQSG CLPLLIQLLH   360
GNDKDSVLLG NSRGSKEARA RASAALHNII HSQPDDKRGR REIRVLHLLE QIRAYCETCW   420
EWQEAHEPGM DQDKNPMPAP VEHQICPAVC VLMKLSFDEE HRHAMNELGG LQAIAELLQV   480
DCEMYGLTND HYSITLRRYA GMALTNLTFG DVANKATLCS MKGCMRALVA QLKSESEDLQ   540
QVIASVLRNL SWRADVNSKK TLREVGSVKA LMECALEVKK ESTLKSVLSA LWNLSAHCTE   600
NKADICAVDG ALAFLVGTLT YRSQTNTLAI IESGGGILRN VSSLIATNED HRQILRENNC   660
LQTLLQHLKS HSLTIVSNAC GTLWNLSARN PKDQEALWDM GAVSMLKNLI HSKHKMIAMG   720
SAAALRNLMA NRPAKYKDAN IMSPGSSLPS LHVRKQKALE AELDAQHLSE TFDNIDNLSP   780
KASHRSKQRH KQSLYGDYVF DTNRHDDNRS DNFNTGNMTV LSPYLNTTVL PSSSSSRGSL   840
DSSRSEKDRS LERERGIGLG NYHPATENPG TSSKRGLQIS TTAAQIAKVM EEVSAIHTSQ   900
EDRSSGSTTE LHCVTDERNA LRRSSAAHTH SNTYNFTKSE NSNRTCSMPY AKLEYKRSSN   960
DSLNSVSSSD GYGKRGQMKP SIESYSEDDE SKFCSYGQYP ADLAHKIHSA NHMDDNDGEL  1020
DTPINYSLKY SDEQLNSGRQ SPSQNERWAR PKHIIEDEIK QSEQRQSRNQ STTYPVYTES  1080
TDDKHLKFQP HFGQOECVSP YRSRGANGSE TNRVGSNHGI HVDQPIDYSL EDDYEDDKPT  1140
NYSERYSEEE QHEEEERPTN YSIKYNEEKR HPSSAQSRSG KYATDIPSSQ KQSFSFSKSS  1200
SGQSSKTEHM SSSSENTSTP SSNAKRQNQL TTQDPDSANT NQNVSQSLCQ SSINQETIQT  1260
YCVEDTPICF SRCSSLSSLS SAEDEIGCNQ HPSSAQSRSG QPQKAATCKV SSINQETIQT  1320
EVPAVSQHPR TKSSRLQGSS LSSESARHKA VEFSSGAKSP LQIAEIKEKI GTRSAEDPVS  1380
LMFSRCTSVS SLDSFESRSI ASSVQSEPCS GMVSGIISPS SKSGAQTPKS PPEHYVQETP  1440
```

FIG. 3B

```
LMFSRCTSVS SLDSFESRSI ASSVQSEPCS GMVSGIISPS DLPDSPGQTM PPSRSKTPPP 1440
PPQTAQTKRE VPKNKAPTAE KRESGPKQAA VNAAVQRVQV LPDADTLLHF ATESTPDGFS 1500
CSSSLSALSL DEPFIQKDVE LRIMPPVQEN DNGNETESEQ PKESNENQEK EAEKTIDSEK 1560
DLLDDSDDDD IEILEECIIS AMPTKSSRKA KKPAQTASKL PPPVARKPSQ LPVYKLLPSQ 1620
NRLQPQKHVS FTPGDDMPRV YCVEGTPINF STATSLSDLT IESPPNELAA GEGVRGGAQS 1680
GEFEKRDTIP TEGRSTDEAQ GGKTSSVTIP ELDDNKAEEG DILAECINSA MPKGKSHKPF 1740
RVKKIMDQVQ QASASSSAPN KNQLDGKKKK PTSPVKPIPQ NTEYRTRVRK NADSKNNLNA 1800
ERVFSDNKDS KKQNLKNNSK DFNDKLPNNE DRVRGSFAFD SPHHYTPIEG TPYCFSRNDS 1860
LSSLDFDDDD VDLSREKAEL RKAKENKESE AKVTSHTELT SNQQSANKTQ AIAKQPINRG 1920
QPKPILQKQS TFPQSSKDIP DRGAATDEKL QNFAIENTPV CFSHNSSLSS LSDIDQENNN 1980
KENEPIKETE PPDSQGEPSK PQASGYAPKS FHVEDTPVCF SRNSSLSSLS IDSEDDLLQE 2040
CISSAMPKKK KPSRLKGDNE KHSPRNMGGI LGEDLTLDLK DIQRPDSEHG LSPDSENFDW 2100
KAIQEGANSI VSSLHQAAAA ACLSRQASSD SDSILSLKSG ISLGSPFHLT PDQEEKPFTS 2160
NKGPRILKPG EKSTLETKKI ESESKGIKGG KKVYKSLITG KVRSNSEISG QMKQPLQANM 2220
PSISRGRTMI HIPGVRNSSS STSPVSKKGP PLKTPASKSP SEGQTATTSP RGAKPSVKSE 2280
LSPVARQTSQ IGGSSKAPSR SGSRDSTPSR PAQQPLSRPI QSPGRNSISP GRNGISPPNK 2340
LSQLPRTSSP STASTKSSGS GKMSYTSPGR QMSQQNLTKQ TGLSKNASSI PRSESASKGL 2400
NQMNNGNGAN KKVELSRMSS TKSSGSESDR SERPVLVRQS TFIKEAPSPT LRRKLEESAS 2460
FESLSPSSRP ASPTRSQAQT PVLSPSLPDM SLSTHSSVQA GGWRKLPPNL SPTIEYNDGR 2520
PAKRHDIARS HSESPSRLPI NRSGTWKREH SKHSSSLPRV STWRRTGSSS SILSASSESS 2580
EKAKSEDEKH VNSISGTKQS KENQVSAKGT WRKIKENEFS PTNSTSQTVS SGATNGAESK 2640
TLIYQMAPAV SKTEDVWVRI EDCPINNPRS GRSPTGNTPP VIDSVSEKAN PNIKDSKDNQ 2700
AKQNVGNGSV PMRTVGLENR LNSFIQVDAP DQKGTEIKPG QNNPVPVSET NESSIVERTP 2760
FSSSSSSKHS SPSGTVAARV TPFNYNPSPR KSSADSTSAR PSQIPTPVNN NTKKRDSKTD 2820
STESSGTQSP KRHSGSYLVT SV                                         2842
```

FIG. 4A

```
APC   203  LGTCQDMEKRAQRRIARIQQIEKDILRIRQL  233
               | ::  ||  ||||||:|   |      |
RAL2  576  LTGAKGLQLRALRRIARIEQGGTAISPTSPL  606
```

FIG. 4B

```
APC       453  MKLSFDEEHRHAMNELGGLQAIAELLQVD  481
                  |  :  ||||||  ::|||||   :  :
M3 MAChR  249  LYWRIYKETEKRTKELAGLQASGTEAETE  277
                ||  :  ::  ||:||   ||||||
MCC       220  LYPNLAEERSRWEKELAGLREENESLTAM  248
                  ::  ||:||   ||   |  |
APC       453  MKLSFDEEHRHAMNELGGLQAIAELLQVD  481
```

FIG. 6A

```
                                                            28                                                          55
GCA GTC GCC GCT CCA GTC TAT CCG GCA CTA GGA ACA GCC CCG GGN GGC GAG ACG
Ala Val Ala Ala Pro Val Tyr Pro Ala Leu Gly Thr Ala Pro Gly Gly Glu Thr
                                                            82                                                          109
GTC CCC GCC ATG TCT GCG GCC ATG GCG AGG GAG TTC GAC CGG TTC CTG CAC GAG
Val Pro Ala MET Ser Ala Ala MET Ala Arg Glu Phe Asp Arg Phe Leu His Glu
                                                            136                                                         163
AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn
                                                            190                                                         217
AGG AGC TTC ATC GCT CTT GGT GTC CTG GGA CTG GTG TAC CTG GCC CTG GTG TTC
Arg Ser Phe Ile Ala Leu Gly Val Leu Gly Leu Val Tyr Leu Ala Leu Val Phe
                                                            244                                                         271
GGT TAT GGA GCC TCT CTC CTC TGC AAC CTG ATA GGA TTT GGC TAC CCA GCC TAC
Gly Tyr Gly Ala Ser Leu Leu Cys Asn Leu Ile Gly Phe Gly Tyr Pro Ala Tyr
                                                            298                                                         325
ATC TCA ATT AAA GCT ATA GAG AGT CCC AAC AAA GAA GAT GAT ACC CAG TGG CTG
Ile Ser Ile Lys Ala Ile Glu Ser Pro Asn Lys Glu Asp Asp Thr Gln Trp Leu
                                                            352                                                         379
ACC TAC TGG GTA GTG TAT GGT GTG TTC AGC ATT GCT GAA TTC TTC TCT GAT ATC
Thr Tyr Trp Val Val Tyr Gly Val Phe Ser Ile Ala Glu Phe Phe Ser Asp Ile
                                                            406                                                         433
TTC CTG TCA TGG TTC CCC TTC TAC TAC ATG CTG AAG TGT GGC TTC CTG TTG TGG
Phe Leu Ser Trp Phe Pro Phe Tyr Tyr MET Leu Lys Cys Gly Phe Leu Leu Trp
                                                            460                                                         487
TGC ATG GCC CCG AGC CCT TCT AAT GGG GCT GAA CTC TAC AAG CGC ATC ATC
Cys MET Ala Pro Ser Pro Ser Asn Gly Ala Glu Leu Tyr Lys Arg Ile Ile
                                                            514                                                         541
CGT CCT TTC TTC CTG AAG CAC GAG TCC CAG ATG GAC AGT GTG GTC AAG GAC CTT
Arg Pro Phe Phe Leu Lys His Glu Ser Gln MET Asp Ser Val Val Lys Asp Leu
```

FIG. 6B

```
                                        568                                    595
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                                            622
ACC GTG AAT TTA CTG GGT GAA GAA AAG AGC ACC TAA ACC AGA
Thr Val Asn Leu Leu Gly Glu Glu Lys Ser Thr
                    640             650             660             670             680             690             700
CTAAACCAGA CTGGATGGAA ACTTCCTGCC CTCTCTGTAC CTTCCTACTG GAGCTTGATG TTATATTAGG
    710             720             730             740             750             760             770
GACTGTGGTA TAATTATTTT AATAATGTTG CCTTGGAAAC ATTTTGAGA TATTAAAGAT TGGAATGTGT
    780             790             800             810             820             830             840
TGTAAGTTTC TTTACTGTACT TTTACTGTCT ATATATATAG GGAGCACTTT AAACTTAATG CAGTGGGCAG
    850             860             870             880             890             900             910
TGTCCACGTT TTTGGAAAAT GTATTTTGCC TCTGGGTAGG AAAAGATGTA TGTTGCTATC CTGCAGGAAA
    920             930             940             950             960             970             980
TATAAACTTA AAATAAAATT ATATACCCCA CAGGCTGTGT ACTTTACTGG GCTCTCCCTG CACGSATTTT
    990            1000            1010            1020            1030            1040            1050
CTCTGTAGTT ACATTTAGGR TAATCTTTAT GGTTCTACTT CCTRTAATGT ACAATTTTAT ATAATTCNGR
   1060            1070            1080            1090            1100            1110            1120
AATGTTTTTA ATGTATTTGT GCACATGTAC ATATGGAAAT GTTACTGTCT GACTACANCA TGCATCATGC
   1130            1140            1150            1160            1170            1180            1190
TCATGGGGAG GGAGCAGGGG AAGGTTGTAT GTGTCATTTA TAACTTCTGT ACAGTAAGAC CACCTGCCAA
   1200            1210            1220            1230            1240            1250            1260
AAGCTGGAGG AACCATTGTG CTGGTGTGGT CTACTAAATA ATACTTTAGG AAATACGTGA TTAAATATGCA
   1270            1280            1290            1300            1310            1320            1330
AGTGAACAAA GTGAGAAATG AAATCGAATG GAGATTGGCC TGGTTGTTTC CGTAGTATAT GGCATATGAA
   1340            1350            1360            1370            1380            1390            1400
```

FIG. 6C

```
TACCAGGATA GCTTTATAAA GCAGTTAGTT AGTTAGTTAC TCACTCTAGT GATAAATCGG GAAATTTACA
          1410       1420       1430       1440       1450       1460       1470
CACACACACA CACACACACA CACACACACA CACACACACA CACACACACA GAGTACCCTG TAACTCTCAA
          1480       1490       1500       1510       1520       1530       1540
TTCCCTGAAA AACTAGTAAT ACTGTCTTAT CTGCTATAAA CTTTACATAT TTGTCTATTG TCAAGATGCT
          1550       1560       1570       1580       1590       1600       1610
ACANTGGAMN CCATTTCTGG TTTTATCTTC ANAGSGGAGA NACATGTTGA TTTAGTCTTC TTTCCCAATC
          1620       1630       1640       1650       1660       1670       1680
TTCTTTTTA AMCCAGTTTN AGGMNCTTCT GRAGATTTGY CCACCCTCGA TTACATGTAT GTTCTYGTTT
          1690       1700       1710       1720       1730       1740       1750
GTATCATKAG CAACAACATG CTAATGRCGA CACCTAGCTC TRAGMGCAAT TCTGGGAGAN TGARAGGNWG
          1760       1770       1780       1790       1800       1810       1820
TATARAGTMN CCCATAATCT GCTTGGCAAT AGTTAAGTCA ATCTATCTTC AGTTTTCTC TGGCCTTTAA
          1830       1840       1850       1860       1870       1880       1890
GGTCAAACAC AAGAGGCTTC CCTAGTTTAC AAGTCAGAGT CACTTGTAGT CCATTTAAAT GCCCTCATCC
          1900       1910       1920       1930       1940       1950       1960
GTATTCTTTG TGTTGATAAG CTGCACAKGA CTACATAGTA AGTACAGANC AGTAAAGTTA ANNCGGATGT
          1970       1980       1990       2000       2010       2020       2030
CTCCATTGAT CTGCCAANTC GNTATAGAGA GCAATTTGTC TGGACTAGAA AATCTGAGTT TTACACCATA
          2040       2050       2060       2070       2080       2090       2100
CTGTTAAGAG TCCTTTTGAA TTAAACTAGA CTAAAACAAG TGTATAACTA AACTAACAAG ATTAAATATC
          2110       2120       2130       2140       2150       2160       2170
CAGCCAGTAC AGTATTTTT AAGGCAAATA AAGATGATTA GCTCACCTTG AGNTAACAAT CAGGTAAGAT
          2180       2190       2200       2210       2220       2230       2240
CATNACAATG TCTCATGATG TNAANAATAT TAAAGATATC AATACTAAGT GACAGTATCA CNNCTAATAT
```

FIG. 6D

```
       2250       2260       2270       2280       2290       2300       2310
AATATGGATC AGAGCATTTA TTTGGGGAG GAAAACAGTG GTGATTACCG GCATTTTATT AAACTTAAAA
       2320       2330       2340       2350       2360       2370       2380
CTTTGTAGAA AGCAAACAAA ATTGTTCTTG GGAGAAAATC AACTTTTAGA TTAAAAAAAT TTTAAGTAWC
       2390       2400       2410       2420       2430       2440       2450
TAGGAGTATT TAAATCCTTT TCCCATAAAT AAAAGTACAG TTTTCTTGGT GGCAGAATGA AAATCAGCAA
       2460       2470       2480       2490       2500       2510       2520
CNTCTAGCAT ATAGACTATA TAATCAGATT GACAGCATAT AGAATATATT ATCAGACAAG ATGAGGAGGT
       2530       2540       2550       2560       2570       2580       2590
ACAAAAGTTA CTATTGCTCA TAATGACTTA CAGGCTAAAA NTAGNTNTAA AATACTATAT TAAATTCTGA
       2600       2610       2620       2630       2640       2650       2660
ATGCAATTTT TTTTTGTTCC CTTGAGACCA AAATTTAAGT TAACTGTTGC TGGCAGTCTA AGTGTAAATG
       2670       2680       2690       2700       2710       2720       2730
TTAACAGCAG GAGAAGTTAA GAATTGAGCA GTTCTGTTGC ATGATTTCCC AAATGAAATA CTGCCTTGGC
       2740       2750       2760       2770       2780       2790       2800
TAGAGTTTGA AAAACTAATT GAGCCTGTGC CTGGCTAGAA AACAAGCGTT TATTTGAATG TGAATAGTGT
       2810       2820       2830       2840       2850       2860       2870
TTCAAAGGTA TGTAGTTACA GAATTCCTAC CAAACAGCTT AAATTCTTCA AGAAAGAATT CCTGCAGCAG
       2880       2890       2900       2910       2920       2930       2940
TTATTCCCTT ACCTGAAGGC TTCAATCATT TGGATCAACA ACTGCTACTC TCGGGAAGAC TCCTCTACTC
       2950       2960       2970       2980       2990       3000       3010
ACAGCTGAAG AAAATGAGCA CACCCTTCAC ACTGTTATCA CCTATCCTGA AGATGTGATA CACTGAATGG
       3020       3030       3040       3050       3060       3070       3080
AAATAAATAG ATGTAAATAA AATTGAGWTC TCATTTAAAA AAAACCATGT GCCCAATGGG AAAATGACCT
       3090       3100       3110       3120       3130       3140       3150
CATGTTGTGG TTTAAACAGC AACTGCACCC ACTAGCACAG CCCATTGAGC TANCCTATAT ATACATCTCT
       3160
GTCAGTGCCC CTC
```

FIG. 7A

```
GGA CTC GGA AAT GAG GTC CAA GGG TAG CCA AGG ATG GCT GCA TCA TAT GAT      54
Gly Leu Gly Asn Glu Val Gln Gly  .  Pro Arg MET Ala Ala Ser Tyr Asp

CAG TTG TTA AAG CAA GTT GAG GCA CTG AAG ATG GAG AAC TCA AAT CTT CGA CAA  108
Gln Leu Leu Lys Gln Val Glu Ala Leu Lys MET Glu Asn Ser Asn Leu Arg Gln

GAG CTA GAA GAT AAT TCC AAT CAT CTT ACA AAA CTG GAA ACT GAG GCA TCT AAT  162
Glu Leu Glu Asp Asn Ser Asn His Leu Thr Lys Leu Glu Thr Glu Ala Ser Asn

ATG AAG GAA GTA CTT AAA CAA CTA GAA AGT ATT GAA GAT GAA GCT ATG GCT      216
MET Lys Glu Val Leu Lys Gln Leu Glu Ser Ile Glu Asp Glu Ala MET Ala

TCT TCT GGA CAG ATT GAT TTA GAG CGT CTT AAA GAG CTT AAC TTA GAT AGC      270
Ser Ser Gly Gln Ile Asp Leu Glu Arg Leu Lys Glu Leu Asn Leu Asp Ser

AGT AAT TTC CCT GGA GTA AAA CTG CGG TCA AAA ATG TCC CTC CGT TCT TAT GGA  324
Ser Asn Phe Pro Gly Val Lys Leu Arg Ser Lys MET Ser Leu Arg Ser Tyr Gly
```

FIG. 7B

```
AGT AAT TTC CCT GGA GTA AAA CTG CGG TCA AAA ATG TCC CTC CGT TCT TAT GGA
Ser Asn Phe Pro Gly Val Lys Leu Arg Ser Lys MET Ser Leu Arg Ser Tyr Gly
                    297                                              324

AGC CGG GAA GGA TCT GTA TCA AGC CGT TCT GGA GAG TGC AGT CCT GTT CCT ATG
Ser Arg Glu Gly Ser Val Ser Ser Arg Ser Gly Glu Cys Ser Pro Val Pro MET
                    351                                              378

GGT TCA TTT CCA AGA AGA GGG TTT GTA AAT GGA AGA AGT ACT GGA TAT
Gly Ser Phe Pro Arg Arg Gly Phe Val Asn Gly Ser Arg Glu Ser Thr Gly Tyr
                    405                                              432

TTA GAA GAA CTT GAG AAA GAG AGG TCA TTG CTT CTT GCT GAT CTT GAC AAA GAA
Leu Glu Glu Leu Glu Lys Glu Arg Ser Leu Leu Leu Ala Asp Leu Asp Lys Glu
                    459                                              486

GAA AAG GAA AAA GAC TGG TAT TAC TAC GCT CAA CTT CAG AAT CTC ACT AAA AGA ATA
Glu Lys Glu Lys Asp Trp Tyr Tyr Tyr Ala Gln Leu Gln Asn Leu Thr Lys Arg Ile
                    513                                              540

```
GAT AGT CTT CCT TTA ACT GAA AAT TTT TCC TTA CAA ACA GAT TTG ACC AGA AGG
Asp Ser Leu Pro Leu Thr Glu Asn Phe Ser Leu Gln Thr Asp Leu Thr Arg Arg
                                                                        648
CAA TTG GAA TAT GAA GCA AGG CAA ATC AGA GTT GCG ATG GAA GAA CAA CTA GGT
Gln Leu Glu Tyr Glu Ala Arg Gln Ile Arg Val Ala MET Glu Glu Gln Leu Gly
                                                                        702
ACC TGC CAG GAT ATG GAA AAA CGA GCA CAG CGA AGA ATA GCC AGA ATT CAG CAA
Thr Cys Gln Asp MET Glu Lys Arg Ala Gln Arg Arg Ile Ala Arg Ile Gln Gln
                                                                        756
ATC GAA AAG GAC ATA CTT CGT ATA CGA CAG CTT TTA CAG TCC CAA GCA ACA GAA
Ile Glu Lys Asp Ile Leu Arg Ile Arg Gln Leu Leu Gln Ser Gln Ala Thr Glu
                                                                        810
GCA GAG AGG TCA TCT CAG AAC AAG CAT GAA ACC GGC TCA CAT GAT GCT GAG CGG
Ala Glu Arg Ser Ser Gln Asn Lys His Glu Thr Gly Ser His Asp Ala Glu Arg
                                                                        864
CAG AAT GAA GGT CAA GGA GTG GGA GAA ATC AAC ATG GCA ACT TCT GGT AAT GGT
Gln Asn Glu Gly Gln Gly Val Gly Glu Ile Asn MET Ala Thr Ser Gly Asn Gly
```

FIG. 7D

```
                                                                                    918
CAG GGT TCA ACT ACA CGA ATG GAC CAT GAA ACA GCC AGT GTT TTG AGT TCT AGT
Gln Gly Ser Thr Thr Arg MET Asp His Glu Thr Ala Ser Val Leu Ser Ser Ser

972
AGC ACA CAC TCT GCA CCT CGA AGG CTG ACA AGT CAT CTG GGA ACC AAG GTG GAA
Ser Thr His Ser Ala Pro Arg Arg Leu Thr Ser His Leu Gly Thr Lys Val Glu

1026
ATG GTG TAT TCA TTG TTG TCA ATG TCT GGT ACT CAT GAT AAG GAT GAT ATG TCG
MET Val Tyr Ser Leu Leu Ser MET Ser Gly Thr His Asp Lys Asp Asp MET Ser

1080
CGA ACT TTG CTA GCT ATG TCT AGC TCC CAA GAC AGC TGT ATA TCC ATG CGA CAG
Arg Thr Leu Leu Ala MET Ser Ser Ser Gln Asp Ser Cys Ile Ser MET Arg Gln

1134
TCT GGA TGT CTT CCT CTC CTC ATC CAG CTT TTA CAT GGC AAT GAC AAA GAC TCT
Ser Gly Cys Leu Pro Leu Leu Ile Gln Leu Leu His Gly Asn Asp Lys Asp Ser

1188
GTA TTG TTG GGA AAT TCC CGG GGC AGT AAA GAG GCT CGG GCC AGG GCC AGT GCA
```

FIG. 7E

```
Val Leu Leu Gly Asn Ser Arg Gly Ser Lys Glu Ala Arg Ala Arg Ser Ala
                                                                    1242
GCA CTC CAC AAC ATC ATT CAC TCA CAG CCT GAT GAC AAG AGA GGC AGG CGT GAA
Ala Leu His Asn Ile Ile His Ser Gln Pro Asp Asp Lys Arg Gly Arg Arg Glu
                          1215                                      1296
ATC CGA GTC CTT CAT CTT TTG GAA CAG ATA CGC GCT TAC TGT GAA ACC TGT TGG
Ile Arg Val Leu His Leu Leu Glu Gln Ile Arg Ala Tyr Cys Glu Thr Cys Trp
          1269                                                      1350
GAG TGG CAG GAA GCT CAT GAA CCA GGC ATG GAC CAG GAC AAA AAT CCA ATG CCA
Glu Trp Gln Glu Ala His Glu Pro Gly MET Asp Gln Asp Lys Asn Pro MET Pro
              1323                                                  1404
GCT CCT GTT GAA CAT CAG ATC TGT CCT GCT GTG TGT GTT CTA ATG AAA CTT TCA
Ala Pro Val Glu His Gln Ile Cys Pro Ala Val Cys Val Leu MET Lys Leu Ser
                  1377                                              1458
TTT GAT GAA GAG CAT AGA CAT GCA ATG AAT GAA CTA GGG GGA CTA CAG GCC ATT
Phe Asp Glu Glu His Arg His Ala MET Asn Glu Leu Gly Gly Leu Gln Ala Ile
                      1431
```

FIG. 7F

```
                                                                          1512
GCA GAA TTA TTG CAA GTG GAC TGT GAA ATG TAT GGG CTT ACT AAT GAC CAC TAC
Ala Glu Leu Leu Gln Val Asp Cys Glu MET Tyr Gly Leu Thr Asn Asp His Tyr

1566
AGT ATT ACA CTA AGA CGA TAT GCT GGA ATG GCT TTG ACA AAC TTG ACT TTT GGA
Ser Ile Thr Leu Arg Arg Tyr Ala Gly MET Ala Leu Thr Asn Leu Thr Phe Gly

1620
GAT GTA GCC AAC AAG GCT ACG CTA TGC TCT ATG AAA GGC TGC ATG AGA GCA CTT
Asp Val Ala Asn Lys Ala Thr Leu Cys Ser MET Lys Gly Cys MET Arg Ala Leu

1674
GTG GCC CAA CTA AAA TCT GAA AGT GAA GAC TTA CAG CAG GTT ATT GCA AGT GTT
Val Ala Gln Leu Lys Ser Glu Ser Glu Asp Leu Gln Gln Val Ile Ala Ser Val

1728
TTG AGG AAT TTG TCT TGG CGA GCA GAT GTA AAT AGT AAA AAG ACG TTG CGA GAA
Leu Arg Asn Leu Ser Trp Arg Ala Asp Val Asn Ser Lys Lys Thr Leu Arg Glu

1782
GTT GGA AGT GTG AAA GCA TTG ATG GAA TGT GCT TTA GAA GTT AAA AAG GAA TCA
Val Gly Ser Val Lys Ala Leu MET Glu Cys Ala Leu Glu Val Lys Lys Glu Ser
```

FIG. 7G

```
                                                                              1836
ACC CTC AAA AGC GTA TTG AGT GCC TTA TGG AAT TTG TCA GCA CAT TGC ACT GAG
Thr Leu Lys Ser Val Leu Ser Ala Leu Trp Asn Leu Ser Ala His Cys Thr Glu

1890
AAT AAA GCT GAT ATA TGT GCT GTA GAT GGT GCA CTT GCA TTT TTG GTT GGC ACT
Asn Lys Ala Asp Ile Cys Ala Val Asp Gly Ala Leu Ala Phe Leu Val Gly Thr

1944
CTT ACT TAC CGG AGC CAG ACA AAC ACT TTA GCC ATT ATT GAA AGT GGA GGT GGG
Leu Thr Tyr Arg Ser Gln Thr Asn Thr Leu Ala Ile Ile Glu Ser Gly Gly Gly

1998
ATA TTA CGG AAT GTG TCC AGC TTG ATA GCT ACA AAT GAG GAC CAC AGG CAA ATC
Ile Leu Arg Asn Val Ser Ser Leu Ile Ala Thr Asn Glu Asp His Arg Gln Ile

2052
CTA AGA GAG AAC AAC TGT CTA TTA CAA CAC TTA AAA TCT CAT AGT
Leu Arg Glu Asn Asn Cys Leu Leu Gln His Leu Lys Ser His Ser

2106
TTG ACA ATA GTC AGT AAT GCA TGT GGA ACT TTG TGG AAT CTC TCA GCA AGA AAT
Leu Thr Ile Val Ser Asn Ala Cys Gly Thr Leu Trp Asn Leu Ser Ala Arg Asn
```

FIG. 7H

```
                                                                    2160
CCT AAA GAC CAG GAA GCA TTA TGG GAC ATG GGG GCA GTT AGC ATG CTC AAG AAC
Pro Lys Asp Gln Glu Ala Leu Trp Asp MET Gly Ala Val Ser MET Leu Lys Asn

2214
CTC ATT CAT TCA AAG CAC AAA ATG ATT GCT ATG GGA AGT GCT GCA TTA AGG
Leu Ile His Ser Lys His Lys MET Ile Ala MET Gly Ser Ala Ala Leu Arg

2268
AAT CTC ATG GCA AAT AGG CCT GCG AAG TAC AAG GAT GCC AAT ATT ATG TCT CCT
Asn Leu MET Ala Asn Arg Pro Ala Lys Tyr Lys Asp Ala Asn Ile MET Ser Pro

2322
GGC TCA AGC TTG CCA TCT CTT CAT GTT AGG AAA CAA AAA GCC CTA GAA GCA GAA
Gly Ser Ser Leu Pro Ser Leu His Val Arg Lys Gln Lys Ala Leu Glu Ala Glu

2376
TTA GAT GCT CAG CAC TTA TCA GAA ACT TTT GAC AAT ATA GAC AAT TTA AGT CCC
Leu Asp Ala Gln His Leu Ser Glu Thr Phe Asp Asn Ile Asp Asn Leu Ser Pro
```

FIG. 71

```
                                                              2430
AAG GCA TCT CAT CGT AGT AAG CAG AGA CAC AAG CAA AGT CTC TAT GGT GAT TAT
Lys Ala Ser His Arg Ser Lys Gln Arg His Lys Gln Ser Leu Tyr Gly Asp Tyr
                                                              2484
GTT TTT GAC ACC AAT CGA CAT GAT AAT AGG TCA GAC AAT TTT AAT ACT GGC
Val Phe Asp Thr Asn Arg His Asp Asn Arg Ser Asp Asn Phe Asn Thr Gly
                                                              2538
AAC ATG ACT GTC CTT TCA CCA TAT TTG AAT ACT ACA GTG TTA CCC AGC TCC TCT
Asn MET Thr Val Leu Ser Pro Tyr Leu Asn Thr Thr Val Leu Pro Ser Ser Ser
                                                              2592
TCA TCA AGA GGA AGC TTA GAT AGT TCT CGT TCT GAA AAA GAT AGA AGT TTG GAG
Ser Ser Arg Gly Ser Leu Asp Ser Ser Arg Ser Glu Lys Asp Arg Ser Leu Glu
                                                              2646
AGA GAA CGC GGA ATT GGT CTA GGC AAC TAC CAT CCA GCA ACA GAA AAT CCA GGA
Arg Glu Arg Gly Ile Gly Leu Gly Asn Tyr His Pro Ala Thr Glu Asn Pro Gly
                                                              2700
ACT TCT TCA AAG CGA GGT TTG CAG ATC TCC ACC ACT GCA GCC CAG ATT GCC AAA
Thr Ser Ser Lys Arg Gly Leu Gln Ile Ser Thr Thr Ala Ala Gln Ile Ala Lys
```

FIG. 7J

```
                                                                    2754
GTC ATG GAA GAA GTG TCA GCC ATT CAT ACC TCT CAG GAA GAC AGA AGT TCT GGG
Val MET Glu Glu Val Ser Ala Ile His Thr Ser Gln Glu Asp Arg Ser Ser Gly

2808
TCT ACC ACT GAA TTA CAT TGT GTG ACA GAT GAG AGA AAT GCA CTT AGA AGA AGC
Ser Thr Thr Glu Leu His Cys Val Thr Asp Glu Arg Asn Ala Leu Arg Arg Ser

2862
TCT GCT GCC CAT ACA CAT TCA AAC ACT TAC AAT TTC ACT AAG TCG GAA AAT TCA
Ser Ala Ala His Thr His Ser Asn Thr Tyr Asn Phe Thr Lys Ser Glu Asn Ser

2916
AAT AGG ACA TGT TCT ATG CCT TAT GCC AAA TTA GAA TAC AAG AGA TCT TCA AAT
Asn Arg Thr Cys Ser MET Pro Tyr Ala Lys Leu Glu Tyr Lys Arg Ser Ser Asn

2970
GAT AGT AGT AGT GTC AGT AGT AAT GAT GGT AAA AGA GGT TAT GGT AAG ATG
Asp Ser Leu Asn Ser Val Ser Ser Asn Asp Gly Tyr Gly Lys Arg Gly Gln MET
```

FIG. 7K

```
                                                                              3024
AAA CCC TCG ATT GAA TCC TAT TCT GAA GAT GAT GAA AGT AAG TTT TGC AGT TAT
Lys Pro Ser Ile Glu Ser Tyr Ser Glu Asp Asp Glu Ser Lys Phe Cys Ser Tyr

3078
GGT CAA TAC CCA GCC GAC CTA GCC CAT AAA ATA CAT AGT GCA AAT CAT ATG GAT
Gly Gln Tyr Pro Ala Asp Leu Ala His Lys Ile His Ser Ala Asn His MET Asp

3132
GAT AAT GAT GGA GAA CTA GAT ACA CCA ATA AAT TAT AGT CTT AAA TAT TCA GAT
Asp Asn Asp Gly Glu Leu Asp Thr Pro Ile Asn Tyr Ser Leu Lys Tyr Ser Asp

3186
GAG CAG TTG AAC TCT GGA AGG CAA AGT CCT TCA CAG AAT GAA AGA TGG GCA AGA
Glu Gln Leu Asn Ser Gly Arg Gln Ser Pro Ser Gln Asn Glu Arg Trp Ala Arg

3240
CCC AAA CAC ATA ATA GAA GAT ATA AAA CAA AGT GAG CAA AGA CAA TCA AGG
Pro Lys His Ile Ile Glu Asp Ile Lys Gln Ser Glu Gln Arg Gln Ser Arg

3294
AAT CAA AGT ACA ACT TAT CCT GTT TAT ACT GAG AGC ACT GAT GAT AAA CAC CTC
Asn Gln Ser Thr Thr Tyr Pro Val Tyr Thr Glu Ser Thr Asp Asp Lys His Leu
```

FIG. 7L

```
AAG TTC CAA CCA CAT TTT GGA CAG CAG GAA TGT GTT TCT CCA TAC AGG TCA CGG
Lys Phe Gln Pro His Phe Gly Gln Gln Glu Cys Val Ser Pro Tyr Arg Ser Arg
    3321                                                              3348

GGA GCC AAT GGT TCA GAA ACA AAT CGA GTG GGT TCT AAT CAT GGA ATT AAT CAA
Gly Ala Asn Gly Ser Glu Thr Asn Arg Val Gly Ser Asn His Gly Ile Asn Gln
    3375                                                              3402

AAT GTA AGC CAG TCT TTG TGT CAA GAA GAT GAC TAT GAA GAT GAT AAG CCT ACC
Asn Val Ser Gln Ser Leu Cys Gln Glu Asp Asp Tyr Glu Asp Asp Lys Pro Thr
    3429                                                              3456

AAT TAT AGT GAA CGT TAC TCT GAA CGT TAC TCT GAA GAA CAG CAT GAA GAA CCA GAA GAG AGA CCA
Asn Tyr Ser Glu Arg Tyr Ser Glu Glu Gln His Glu Glu Glu Glu Arg Pro
    3483                                                              3510

ACA AAT TAT AGC ATA AAA TAT GAA GAG AAA CGT CAT GTG GAT CAG CCT ATT
Thr Asn Tyr Ser Ile Lys Tyr Asn Glu Glu Lys Arg His Val Asp Gln Pro Ile
    3537                                                              3564

```
GAT TAT AGT TTA AAA TAT GCC ACA GAT ATT CCT TCA TCA CAG AAA CAG TCA TTT
Asp Tyr Ser Leu Lys Tyr Ala Thr Asp Ile Pro Ser Ser Gln Lys Gln Ser Phe
                                                                      3672
TCA TTC TCA AAG AGT TCA TCT GGA CAA AGC AGT AAA ACC GAA CAT ATG TCT TCA
Ser Phe Ser Lys Ser Ser Ser Gly Gln Ser Ser Lys Thr Glu His MET Ser Ser
                                                                      3726
AGC AGT GAG AAT ACG TCC ACA CCT TCA TCT AAT GCC AAG AGG CAG AAT CAG CTC
Ser Ser Glu Asn Thr Ser Thr Pro Ser Ser Asn Ala Lys Arg Gln Asn Gln Leu
                                                                      3780
CAT CCA AGT TCT GCA CAG AGT GGT AGT AGA AGT GGT CAG CCT CAA AAG GCT GCC ACT TGC
His Pro Ser Ser Ala Gln Ser Gly Ser Arg Ser Gly Gln Pro Gln Lys Ala Ala Thr Cys
                                                                      3834
AAA GTT TCT TCT ATT AAC CAA GAA ACA ATA CAG ACT TAT TGT GTA GAA GAT ACT
Lys Val Ser Ser Ile Asn Gln Glu Thr Ile Gln Thr Tyr Cys Val Glu Asp Thr
                                                                      3888
CCA ATA TGT TTT TCA AGA TGT TCA TTA TCA TCT TTG TCA TCT GCT GAA GAT
Pro Ile Cys Phe Ser Arg Cys Ser Leu Ser Ser Leu Ser Ser Ala Glu Asp
```

FIG. 7N

```
                                                          3915                                                                                    3942
GAA ATA GGA TGT AAT CAG ACG ACA CAG GAA GCA GAT TCT GCT AAT ACC CTG CAA
Glu Ile Gly Cys Asn Gln Thr Thr Gln Glu Ala Asp Ser Ala Asn Thr Leu Gln 3969                                                                                    3996
ATA GCA GAA ATA AAA GGA AAG ATT GGA ACT AGG TCA GCT GAA GAT CCT GTG AGC
Ile Ala Glu Ile Lys Gly Lys Ile Gly Thr Arg Ser Ala Glu Asp Pro Val Ser 4023                                                                                    4050
GAA GTT CCA GCA GTG TCA CAG CAC CCT AGA ACC AAA TCC AGC AGA CTG CAG GGT
Glu Val Pro Ala Val Ser Gln His Pro Arg Thr Lys Ser Ser Arg Leu Gln Gly 4077                                                                                    4104
TCT AGT TTA TCT TCA GAA TCA GCC AGG CAC AAA GCT GTT GAA TTT CCT TCA GGA
Ser Ser Leu Ser Ser Glu Ser Ala Arg His Lys Ala Val Glu Phe Pro Ser Gly 4131                                                                                    4158
GCG AAA TCT CCC TCC AAA AGT GGT GCT CAG ACA CCC AAA AGT CCA CCT GAA CAC
Ala Lys Ser Pro Ser Lys Ser Gly Ala Gln Thr Pro Lys Ser Pro Pro Glu His 4185                                                                                    4212
TAT GTT CAG GAG ACC CCA CTC ATG TTT AGC AGA TGT ACT TCT GTC AGT TCA CTT
Tyr Val Gln Glu Thr Pro Leu Met Phe Ser Arg Cys Thr Ser Val Ser Ser Leu
```

FIG. 70

```
                                                                                              4266
Tyr Val Gln Glu Thr Pro Leu MET Phe Ser Arg Cys Thr Ser Val Ser Ser Leu 4239                                                    4320
GAT AGT TTT GAG AGT CGT TCG ATT GCC   AGC TCC GTT CAG AGT CAA CCA TGC AGT
Asp Ser Phe Glu Ser Arg Ser Ile Ala   Ser Ser Val Gln Ser Gln Pro Cys Ser 4293                                                    4374
GGA ATG GTA AGT GGC ATT ATA AGC CCC   AGT GAT CTT CCA GAT AGC CCT GGA CAA
Gly MET Val Ser Gly Ile Ile Ser Pro   Ser Asp Leu Pro Asp Ser Pro Gly Gln 4347                                                    4428
ACC ATG CCA CCA AGC AGA AGT AAA ACA   CCT CCA CCT CAA ACA GCT CAA ACA GCT CAA
Thr MET Pro Pro Ser Arg Ser Lys Thr   Pro Pro Pro Gln Thr Ala Gln Thr Ala Gln 4401                                                    4428
ACC AAG CGA GAA GTA CCT AAA AAT GCA   CCT ACT GCT GAA AAG AGA GAG AGT CAA
Thr Lys Arg Glu Val Pro Lys Asn Ala   Pro Thr Ala Glu Lys Arg Glu Ser Gln 4455                                                    4482
GGA CCT AAG CAA GCT GCA GTA AAT GCT   GCA GTT CAG AGG GTC CAG GTT CTT CCA
Gly Pro Lys Gln Ala Ala Val Asn Ala   Ala Val Gln Arg Val Gln Val Leu Pro
```

FIG. 7P

```
                                                           4536
GAT GCT GAT ACT TTA CAT TTT GCC ACA GAA AGT ACT CCA GAT GGA TTT TCT
Asp Ala Asp Thr Leu Leu His Phe Ala Thr Glu Ser Thr Pro Asp Gly Phe Ser
         4509                                                      4590
TGT TCA TCC AGC CTG AGT GCT CTG GAT GAG CCA TTT ATA CAG AAA GAT
Cys Ser Ser Ser Leu Ser Ala Leu Ser Leu Asp Glu Pro Phe Ile Gln Lys Asp
         4563                                                      4644
GTG GAA TTA AGA ATA ATG CCT CCA GTT CAG GAA AAT GAC AAT GGG AAT GAA ACA
Val Glu Leu Arg Ile MET Pro Pro Val Gln Glu Asn Asp Asn Gly Asn Glu Thr
         4617                                                      4698
GAA TCA GAG CAG CCT AAA GAA AAT TCA AAT GAA AAC CAA GAG AAA GAG GCA GAA AAA
Glu Ser Glu Gln Pro Lys Glu Asn Ser Asn Glu Asn Gln Glu Lys Glu Ala Glu Lys
         4671                                                      4752
ACT ATT GAT TCT GAA AAG GAC CTA TTA GAT GAT TCA GAT GAT GAT ATT GAA
Thr Ile Asp Ser Glu Lys Asp Leu Leu Asp Asp Ser Asp Asp Asp Ile Glu
         4725                                                      4806
ATA CTA GAA GAA TGT ATT ATT TCT GCC ATG CCA ACA AAG TCA TCA CGT AAA GGC
Ile Leu Glu Glu Cys Ile Ile Ser Ala MET Pro Thr Lys Ser Ser Arg Lys Gly
         4779
```

FIG. 7Q

```
                                                                              4860
AAA AAG CCA GCC CAG ACT GCT TCA AAA TTA CCT CCA CCT GTG GCA AGG AAA CCA
Lys Lys Pro Ala Gln Thr Ala Ser Lys Leu Pro Pro Pro Val Ala Arg Lys Pro

4914
AGT CAG CTG CCT GTG TAC AAA CTT CTA CCA TCA CAA AAC AGG TTG CAA CCC CAA
Ser Gln Leu Pro Val Tyr Lys Leu Leu Pro Ser Gln Asn Arg Leu Gln Pro Gln

4968
AAG CAT GTT AGT TTT ACA CCG GGG GAT GAT ATG CCA CGG GTG TAT TGT GTT GAA
Lys His Val Ser Phe Thr Pro Gly Asp Asp MET Pro Arg Val Tyr Cys Val Glu

5022
GGG ACA CCT ATA AAC TTT TCC ACA TCT CTA AGT GAT CTA ACA ATC GAA
Gly Thr Pro Ile Asn Phe Ser Thr Ala Thr Ser Leu Ser Asp Leu Thr Ile Glu

5076
TCC CCT CCA AAT GAG TTA GCT GCT GGA GAA GGA GTT AGA GGA GCA CAG TCA
Ser Pro Pro Asn Glu Leu Ala Ala Gly Glu Gly Val Arg Gly Ala Gln Ser

5130
GGT GAA TTT GAA AAA CGA GAT ACC ATT CCT ACA GAA GGC AGA AGT ACA GAT GAG
Gly Glu Phe Glu Lys Arg Asp Thr Ile Pro Thr Glu Gly Arg Ser Thr Asp Glu
```

FIG. 7R

```
       5157                                              5184
GCT CAA GGA GGA AAA ACC TCA TCT GTA ACC ATA CCT GAA TTG GAT GAC AAT AAA
Ala Gln Gly Gly Lys Thr Ser Ser Val Thr Ile Pro Glu Leu Asp Asp Asn Lys 5211                                              5238
GCA GAG GAA GGT GAT ATT CTT GCA GAA TGC ATT AAT TCT GCT ATG CCC AAA GGG
Ala Glu Glu Gly Asp Ile Leu Ala Glu Cys Ile Asn Ser Ala MET Pro Lys Gly 5265                                              5292
AAA AGT CAC AAG CCT TTC CGT GTG AAA ATA ATG GAC CAG GTC CAG CAA GCA
Lys Ser His Lys Pro Phe Arg Val Lys Ile MET Asp Gln Val Gln Gln Ala 5319                                              5346
TCT GCG TCG TCT TCT GCA CCC AAC AAA AAT CAG TTA GAT GGT AAG AAA AAG
Ser Ala Ser Ser Ser Ala Pro Asn Lys Asn Gln Leu Asp Gly Lys Lys Lys 5373                                              5400
CCA ACT TCA CCA GTA AAA CCT ATA CCA CAA AAT ACT GAA TAT AGG ACA CGT GTA
Pro Thr Ser Pro Val Lys Pro Ile Pro Gln Asn Thr Glu Tyr Arg Thr Arg Val
```

FIG. 7S

```
                                                                   5454
AGA AAA AAT GCA GAC TCA AAA AAT AAT TTA AAT GCT GAG AGA GTT TTC TCA GAC
Arg Lys Asn Ala Asp Ser Lys Asn Asn Leu Asn Ala Glu Arg Val Phe Ser Asp 5481                                                    5508
AAC AAA GAT TCA AAG AAA CAG AAT TTG AAA AAT AAT TCC AAG GAC TTC AAT GAT
Asn Lys Asp Ser Lys Lys Gln Asn Leu Lys Asn Asn Ser Lys Asp Phe Asn Asp 5535                       5562
AAG CTC CCA AAT AAT GAA GAT AGA GGA AGT GTC AGA GGA AGT TTT GCT TTT GAT TCA CCT
Lys Leu Pro Asn Asn Glu Asp Arg Val Arg Gly Ser Phe Ala Phe Asp Ser Pro 5589                                 5616
CAT CAT TAC ACG CCT ATT GAA GGA ACT CCT TAC TGT TTT TCA CGA AAT GAT TCT
His His Tyr Thr Pro Ile Glu Gly Thr Pro Tyr Cys Phe Ser Arg Asn Asp Ser 5643                                                    5670
TTG AGT TCT CTA GAT GAT TTT GAT GAT GAT GTT GAC CTT TCC AGG GAA AAG GCT
Leu Ser Ser Leu Asp Asp Phe Asp Asp Asp Val Asp Leu Ser Arg Glu Lys Ala 5697                                 5724
GAA TTA AGA AAG GCA AAA GAA AAT AAG GAA TCA GAG GCT AAA GTT ACC AGC CAC
Glu Leu Arg Lys Ala Lys Glu Asn Lys Glu Ser Glu Ala Lys Val Thr Ser His
```

FIG. 77

```
      5751                                                          5778
ACA GAA CTA ACC TCC AAC CAA TCA GCT AAT AAG ACA CAA GCT ATT GCA AAG
Thr Glu Leu Thr Ser Asn Gln Ser Ala Asn Lys Thr Gln Ala Ile Ala Lys 5805                                                          5832
CAG CCA ATA AAT CGA GGT CAG CCT AAA CCC ATA CTT CAG AAA CAA TCC ACT TTT
Gln Pro Ile Asn Arg Gly Gln Pro Lys Pro Ile Leu Gln Lys Gln Ser Thr Phe 5859                                                          5886
CCC CAG TCA TCC AAA GAC ATA CCA GAC AGA GGG GCA GCA ACT GAT GAA AAG TTA
Pro Gln Ser Ser Lys Asp Ile Pro Asp Arg Gly Ala Ala Thr Asp Glu Lys Leu 5913                                                          5940
CAG AAT TTT GCT ATT GAA AAT ACT CCA GTT TGC TTT TCT CAT AAT TCC TCT CTG
Gln Asn Phe Ala Ile Glu Asn Thr Pro Val Cys Phe Ser His Asn Ser Ser Leu 5967                                                          5994
AGT TCT CTC AGT GAC ATT GAC CAA GAA AAC AAC AAT AAA GAA AAT GAA CCT ATC
Ser Ser Leu Ser Asp Ile Asp Gln Glu Asn Asn Asn Lys Glu Asn Glu Pro Ile
```

FIG. 7U

```
                                                                      6048
      6021
AAA GAG ACT GAG CCC CCT GAC TCA CAG GGA GAA CCA AGT AAA CCT CAA GCA TCA
Lys Glu Thr Glu Pro Pro Asp Ser Gln Gly Glu Pro Ser Lys Pro Gln Ala Ser 6102
      6075
GGC TAT GCT CCT AAA TCA TTT CAT GTT GAA GAT ACC CCA GTT TGT TTC TCA AGA
Gly Tyr Ala Pro Lys Ser Phe His Val Glu Asp Thr Pro Val Cys Phe Ser Arg 6156
      6129
AAC AGT TCT CTC AGT TCT CTT AGT ATT GAC TCT GAA GAT GAC CTG TTG CAG GAA
Asn Ser Ser Leu Ser Ser Leu Ser Ile Asp Ser Glu Asp Asp Leu Leu Gln Glu 6210
      6183
TGT ATA AGC TCC GCA ATG CCA AAA AAG AAA CCT TCA AGA CTC AAG GGT GAT
Cys Ile Ser Ser Ala MET Pro Lys Lys Lys Pro Ser Arg Leu Lys Gly Asp 6264
      6237
AAT GAA AAA CAT AGT CCC AGA AAT ATG GGT GGC ATA TTA GGT GAA GAT CTG ACA
Asn Glu Lys His Ser Pro Arg Asn MET Gly Gly Ile Leu Gly Glu Asp Leu Thr 6318
      6291
CTT GAT TTG AAA GAT ATA CAG AGA CCA GAT TCA GAA CAT GGT CTA TCC CCT GAT
Leu Asp Leu Lys Asp Ile Gln Arg Pro Asp Ser Glu His Gly Leu Ser Pro Asp
```

FIG. 7V

```
                                          6345                                          6372
TCA GAA AAT TTT GAT TGG AAA GCT ATT CAG GAA GGT GCA AAT TCC ATA GTA AGT
Ser Glu Asn Phe Asp Trp Lys Ala Ile Gln Glu Gly Ala Asn Ser Ile Val Ser 6399                                          6426
AGT TTA CAT CAA GCT GCT GCA TGT TTA TCT AGA CAA GCT TCG TCT GAT
Ser Leu His Gln Ala Ala Ala Cys Leu Ser Arg Gln Ala Ser Ser Asp 6453                                          6480
TCA GAT TCC ATC CTT TCC CTG AAA TCA GGA ATC TCT CTG GGA TCA CCA TTT CAT
Ser Asp Ser Ile Leu Ser Leu Lys Ser Gly Ile Ser Leu Gly Ser Pro Phe His 6507                                          6534
CTT ACA CCT GAT CAA GAA GAA AAA CCC TTT ACA AGT AAT AAA GGC CCA CGA ATT
Leu Thr Pro Asp Gln Glu Glu Lys Pro Phe Thr Ser Asn Lys Gly Pro Arg Ile 6561                                          6588
CTA AAA CCA GGG GAG AAA AGT ACA TTG GAA ACT AAA AAG ATA GAA TCT GAA AGT
Leu Lys Pro Gly Glu Lys Ser Thr Leu Glu Thr Lys Lys Ile Glu Ser Glu Ser 6615                                          6642
```

FIG. 7W

```
AAA GGA ATC AAA GGA AAA GGT TAT AAA AGT TTG ATT ACT GGA AAA GTT
Lys Gly Ile Lys Gly Lys Val Tyr Lys Ser Leu Ile Thr Gly Lys Val
                                                              6696
CGA TCT AAT TCA GAA ATT TCA GGC CAA ATG AAA CAG CCC CTT CAA GCA AAC ATG
Arg Ser Asn Ser Glu Ile Ser Gly Gln MET Lys Gln Pro Leu Gln Ala Asn MET
                                6669                                    6750
CCT TCA ATC TCT CGA GGC AGG ACA ATG ATT CAT ATT CCA GGA GTT CGA AAT AGC
Pro Ser Ile Ser Arg Gly Arg Thr MET Ile His Ile Pro Gly Val Arg Asn Ser
                                6723                                    6804
TCC TCA AGT ACA AGT CCT GTT TCT AAA AAA GGC CCA CCC CTT AAG ACT CCA GCC
Ser Ser Ser Thr Ser Pro Val Ser Lys Lys Gly Pro Pro Leu Lys Thr Pro Ala
                                6777                                    6858
TCC AAA AGC CCT AGT GAA GGT CAA ACA GCC ACC ACT TCT CCT AGA GGA GCC AAG
Ser Lys Ser Pro Ser Glu Gly Gln Thr Ala Thr Thr Ser Pro Arg Gly Ala Lys
                                6831                                    6912
CCA TCT GTG AAA TCA GAA TTA AGC CCT GTT GCC AGG CAG ACA TCC CAA ATA GGT
Pro Ser Val Lys Ser Glu Leu Ser Pro Val Ala Arg Gln Thr Ser Gln Ile Gly
                                6885
```

FIG. 7X

```
     GGG TCA AGT AAA GCA CCT TCT AGA TCA GGA TCT AGA GAT TCG ACC CCT TCA AGA
     Gly Ser Ser Lys Ala Pro Ser Arg Ser Gly Ser Arg Asp Ser Thr Pro Ser Arg
6939                                                                        6966

CCT GCC CAG CAA CCA TTA AGT AGA CCT ATA CAG TCT CCT GGC CGA AAC TCA ATT
     Pro Ala Gln Gln Pro Leu Ser Arg Pro Ile Gln Ser Pro Gly Arg Asn Ser Ile
6993                                                                        7020

TCC CCT GGT AGA AAT GGA ATA AGT CCT CCT AAC AAA TTA TCT CAA CTT CCA AGG
     Ser Pro Gly Arg Asn Gly Ile Ser Pro Pro Asn Lys Leu Ser Gln Leu Pro Arg
7047                                                                        7074

ACA TCA TCC CCT AGT ACT AAG TCC TCA GGT TCT GGA AAA ATG TCA
     Thr Ser Ser Pro Ser Thr Ala Ser Thr Lys Ser Ser Gly Ser Gly Lys MET Ser
7101                                                                        7128

TAT ACA TCT CCA GGT AGA CAG ATG AGC CAA CAG AAC CTT ACC AAA CAA ACA GGT
     Tyr Thr Ser Pro Gly Arg Gln MET Ser Gln Gln Asn Leu Thr Lys Gln Thr Gly
7155                                                                        7182

TTA TCC AAG AAT GCC AGT AGT ATT CCA AGA AGT GAG TCT GCC TCC AAA GGA CTA
7209                                                                        7236
```

FIG. 7Y

```
        Leu Ser Lys Asn Ala Ser Ser Ile Pro Arg Ser Glu Ser Ala Ser Lys Gly Leu
                                                                                    7290
7263
AAT CAG ATG AAT AAT GGT AAT GGA GCC AAT AAA AAG GTA GAA CTT TCT AGA ATG
Asn Gln MET Asn Asn Gly Asn Gly Ala Asn Lys Lys Val Glu Leu Ser Arg MET
                                                                                    7344
7317
TCT TCA ACT AAA TCA AGT GGA AGT GAA TCT GAT AGA TCA GAA AGA CCT GTA TTA
Ser Ser Thr Lys Ser Ser Gly Ser Glu Ser Asp Arg Ser Glu Arg Pro Val Leu
                                                                                    7398
7371
GTA CGC CAG TCA ACT TTC ATC AAA GAA GCT CCA AGC CCA ACC TTA AGA AGA AAA
Val Arg Gln Ser Thr Phe Ile Lys Glu Ala Pro Ser Pro Thr Leu Arg Arg Lys
                                                                                    7452
7425
TTG GAG GAA TCT GCT TCA TTT GAA TCT CTT TCT CCA TCA TCT AGA CCA GCT TCT
Leu Glu Glu Ser Ala Ser Phe Glu Ser Leu Ser Pro Ser Ser Arg Pro Ala Ser
                                                                                    7506
7479
CCC ACT AGG TCC CAG GCA CAA ACT CCA GTT TTA AGT CCT TCC CTT CCT GAT ATG
Pro Thr Arg Ser Gln Ala Gln Thr Pro Val Leu Ser Pro Ser Leu Pro Asp MET
```

FIG. 7Z

```
          7533
TCT CTA TCC ACA CAT TCG TCT GTT CAG GCT GGT GGA TGG CGA AAA CTC CCA CCT    7560
Ser Leu Ser Thr His Ser Ser Val Gln Ala Gly Gly Trp Arg Lys Leu Pro Pro

7587
AAT CTC AGT CCC ACT ATA GAG TAT AAT GAT GGA AGA CCA GCA AAG CGC CAT GAT    7614
Asn Leu Ser Pro Thr Ile Glu Tyr Asn Asp Gly Arg Pro Ala Lys Arg His Asp

7641
ATT GCA CGG TCT CAT TCT GAA AGT CCT TCT AGA CTT CCA ATC AAT AGG TCA GGA    7668
Ile Ala Arg Ser His Ser Glu Ser Pro Ser Arg Leu Pro Ile Asn Arg Ser Gly

7695
ACC TGG AAA CGT GAG CAC AGC AAA CAT TCA TCC CTT CCT CGA GTA AGC ACT        7722
Thr Trp Lys Arg Glu His Ser Lys His Ser Ser Leu Pro Arg Val Ser Thr

7749
TGG AGA AGA ACT GGA AGT TCA TCT TCA ATT CTT TCT GCT TCA GAA TCC AGT        7776
Trp Arg Arg Thr Gly Ser Ser Ser Ile Leu Ser Ala Ser Glu Ser Ser

7803
GAA AAA GCA AAA AGT GAG GAT GAA AAA CAT GTG AAC TCT ATT TCA GGA ACC AAA    7830
Glu Lys Ala Lys Ser Glu Asp Glu Lys His Val Asn Ser Ile Ser Gly Thr Lys
```

FIG. 7AA

```
                                                                    7884
CAA AGT AAA GAA AAC CAA GTA TCC GCA AAA GGA ACA TGG AGA AAA ATA AAA GAA
Gln Ser Lys Glu Asn Gln Val Ser Ala Lys Gly Thr Trp Arg Lys Ile Lys Glu

7938
AAT GAA TTT TCT CCC ACA AAT AGT ACT TCT CAG ACC GTT TCC TCA GGT GCT ACA
Asn Glu Phe Ser Pro Thr Asn Ser Thr Ser Gln Thr Val Ser Ser Gly Ala Thr
        7965                                                        7992
AAT GGT GCT GAA TCA AAG ACT CTA ATT TAT CAA ATG GCA CCT GCT GTT TCT AAA
Asn Gly Ala Glu Ser Lys Thr Leu Ile Tyr Gln MET Ala Pro Ala Val Ser Lys
        8019                                                        8046
ACA GAG GAT GTT TGG GTG AGA ATT GAG GAC TGT CCC ATT AAC AAT CCT AGA TCT
Thr Glu Asp Val Trp Val Arg Ile Glu Asp Cys Pro Ile Asn Asn Pro Arg Ser
        8073                                                        8100
GGA AGA TCT CCC ACA GGT AAT ACT CCC CCG GTG ATT GAC AGT GTT TCA GAA AAG
Gly Arg Ser Pro Thr Gly Asn Thr Pro Pro Val Ile Asp Ser Val Ser Glu Lys
        8127                                                        8154
GCA AAT CCA AAC ATT AAA GAT TCA AAA GAT AAT CAG GCA AAA CAA AAT GTG GGT
Ala Asn Pro Asn Ile Lys Asp Ser Lys Asp Asn Gln Ala Lys Gln Asn Val Gly
```

FIG. 7BB

```
                                                                              8208
AAT GGC AGT GTT CCC ATG CGT ACC GTG GGT TTG GAA AAT CGC CTG ACC TCC TTT
Asn Gly Ser Val Pro MET Arg Thr Val Gly Leu Glu Asn Arg Leu Thr Ser Phe
        8181
                                                                              8262
ATT CAG GTG GAT GCC CCT GAC CAA GGA ACT GAG ATA AAA CCA GGA CAA AAT
Ile Gln Val Asp Ala Pro Asp Gln Gly Thr Glu Ile Lys Pro Gly Gln Asn
        8235
                                                                              8316
AAT CCT GTC CCT GTA TCA GAG ACT AAT GAA AGT CCT ATA GTG GAA CGT ACC CCA
Asn Pro Val Pro Val Ser Glu Thr Asn Glu Ser Pro Ile Val Glu Arg Thr Pro
        8289
                                                                              8370
TTC AGT TCT AGC AGC TCA AGC AAA CAC AGT TCA CCT AGT GGG ACT GTT GCT GCC
Phe Ser Ser Ser Ser Ser Ser Lys His Ser Ser Pro Ser Gly Thr Val Ala Ala
        8343
                                                                              8424
AGA GTG ACT CCT TTT AAT TAC AAC CCA AGC CCT AGG AAA AGC AGC GCA GAT AGC
Arg Val Thr Pro Phe Asn Tyr Asn Pro Ser Pro Arg Lys Ser Ser Ala Asp Ser
        8397
```

FIG. 7CC

```
                                                           8478
ACT TCA GCT CGG CCA TCT CAG ATC CCA ACT CCA GTG AAT AAC ACA AAG AAG
Thr Ser Ala Arg Pro Ser Gln Ile Pro Thr Pro Val Asn Asn Thr Lys Lys

8532
CGA GAT TCC AAA ACT GAC AGC ACA GAA TCC AGT GGA ACC CAA AGT CCT AAG CGC
Arg Asp Ser Lys Thr Asp Ser Thr Glu Ser Ser Gly Thr Gln Ser Pro Lys Arg

8559
CAT TCT GGG TCT TAC CTT GTG ACA TCT GTT TAA .
His Ser Gly Ser Tyr Leu Val Thr Ser Val 8570       8580       8590       8600       8610
AAGAG AGGAAGAATG AAACTAAGAA AATTCTATGT TAATTACAAC 8620       8630       8640       8650       8660       8670       8680
TGCTATATAG ACATTTGTT TCAAATGAAA CTTTAAAAGA CTGAAAAATT TTGTAAATAG GTTTGATTCT 8690       8700       8710       8720       8730       8740       8750
TGTTAGAGGG TTTTTGTTCT GGAAGCCATA TTTGATAGTA TACTTTGTCT TCACTGGTCT TATTTTGGGA 8760       8770       8780       8790       8800       8810       8820
GGCACTCTTG ATGGTTAGGS AAAAAATAGK AAAGCCAAGT ATGTTTGTAC AGTATGTTTT ACATGTATTT 8830       8840       8850       8860       8870       8880       8890
AAAGTAGCAT CCCATCCCAA CTTCCYTTAA TTATTGCTTG TCYTAAAATA ATGAACACTA CAGATAGGAA
```

FIG. 7DD

```
      8900            8910            8920            8930            8940            8950            8960
ATATGATATA      TTGCTGTTAT      CAATCATTTC      TAGATTATAA      ACTGACTAAA      CTTACATCAG      GGGAAAATTG 8970            8980            8990            9000            9010            9020            9030
GTATTTATGC      AAAAAAAAAA      TGTTTTTGTC      CTTGTGAGTC      CATCTAACAT      CATAATTAAT      CATGTGGCTG 9040            9050            9060            9070            9080            9090            9100
TGAAATTCAC      AGTAATATGG      TTCCCGATGA      ACAAGTTTAC      CCAGCCTGCT      TTGCTTNACT      GCATGAATGA 9110            9120            9130            9140            9150            9160            9170
AACTGATGGT      TCAATTTCAG      AAGTAATGAT      TAACAGTTAT      GTGGTCACAT      GATGTGCATA      GAGATAGCTA 9180            9190            9200            9210            9220            9230            9240
CAGTGTAATA      ATTTACACTA      TTTTGTGCTC      CAAACAAAAC      AAAAATCTGT      GTAACTGTAA      AACATTGAAT 9250            9260            9270            9280            9290            9300            9310
GAAACTATTT      TACCTGAACT      AGATTTTATC      TGAAAGTAGG      TAGAATTTTT      GCTATGCTGT      AATTTGTTGT 9320            9330            9340            9350            9360            9370            9380
ATATTCTGGT      ATTTGAGGTG      AGATGGCTGC      TCTTTKATTA      ATGAGACATG      AATTGTGTCT      CAACAGAAAC 9390            9400            9410            9420            9430            9440            9450
TAAATGAACA      TTTCAGAATA      AATTATTGCT      GTATGTAAAC      TGTTACTGAA      ATTGGTATTT      GTTTGAAGGG 9460            9470            9480            9490            9500            9510            9520
TSTTGTTTCA      CATTTGTATT      AATTAATTGT      TTAAAATGCC      TCTTTTAAAA      GCTTATATAA      ATTTTTTNCT
```

FIG. 7EE

```
      9530       9540       9550       9560       9570       9580       9590
TCAGCTTCTA TGCATTAAGA GTAAAATTCC TCTTACTGTA ATAAAAACAR TTGAAGAAGA CTGTTGCCAC 9600       9610       9620       9630       9640       9650       9660
TTAACCATTC CATGCGGTTGG CACTTATCTA TTCCTGAAAT TTCTTTTATG TGATTAGCTC ATCTTGATTT 9670       9680       9690       9700       9710       9720       9730
TWAAYATTTT TCCACTTAAA CTTTTTTTTC TTACTCCACT GGAGCTCAGT AAAAGTAAAT TCATGTAATA 9740       9750       9760       9770       9780       9790       9800
GCAATGCAAG CAGCCTAGCA CAGACTAAGC ATTGAGCATA ATAGGCCCAC ATAATTTCCT CTTTCTTAAT 9810       9820       9830       9840       9850       9860       9870
AWTATAGAAT TCTGTACTTG AAATTRATTC TTAGACATTG CAGTCTCTTC GAGGCTTTAC AGTGTAAACT 9880       9890       9900       9910       9920       9930       9940
GTCTTGCCCC TTCATCTTCT TGTTGCAACT GGGTCTGACA TGAACACTTT TTATCACCCT GTATGTTAGG 9950       9960       9970       9980       9990      10000      10010
GCAAGATCTC AGCAGTGAAG TATAATCAGC ACTTTGCCAT GCTCANRAAA TTCAAATCAC ATGGAACTTT
```

FIG. 7FF

```
           10020          10030          10040          10050          10060          10070          10080
      AGAGGTAGAT     TTAATACGAT     TAAGATATTC     AGAAGTATAT     TTTAGAATCC     CTGCCTGTTA     AGGAAACTTT
           10090          10100          10110          10120          10130          10140          10150
      ATTTGTGGTA     GGTACACAGTTC   TGGGGTACAT     GTTAAGTGTC     CCCTTATACA     GTGGAGGGAA     GTCTTCCTTC
           10160          10170          10180          10190          10200          10210          10220
      CTGAAGGRAA     ATAAACTGAC     ACTTATTAAC     TAAGATAATT     TACTTAAATAT    ATCTYCCCTG     ATTTGTTTTA
           10230          10240          10250          10260          10270          10280          10290
      AAAGATCAGA     GGGTGACTGA     TGATACATGC     ATACATATTT     GTTGAATAAA     TGAAAATTTA     TTTTTAGTGA
           10300          10310          10320          10330          10340          10350          10360
      TAAGANTCAT     ACACTCTGTA     TTTGGGGAGR     GAAAACCTTT     TTAAGCATGG     TGGGGCACTC     AGATAGGNGT
           10370          10380
      NAATACACCT     ACCTGGTGGT     CAT
```

APC GENE AND NUCLEIC ACID PROBES DERIVED THEREFROM

The U.S. Government has a paid-up license in this invention and the right in limited circumstances to require the patent owner to license others on reasonable terms as provided for by the terms of grants awarded by the National Institutes of Health.

TECHNICAL AREA OF THE INVENTION

The invention relates to the area of cancer diagnostics and therapeutics. More particularly, the invention relates to detection of the germline and somatie alterations of wild-type APC genes. In addition, it relates to therapeutic intervention to restore the function of APC (adnomatous polyposis coli) gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the eases of retinoblastoma and colorectal tumors. The implicated suppressor genes in those tumors, RB (retinoblastoma), p53 (protein having a molecular weight of 53 kDa), Dcc (deleted in colorectal cancer) and MCC (mutated in colorectal cancer) were found to be deleted or altered in many eases of the tumors studied. (Hansen and Cavenee, Cancer Research, Vol.. 47, pp. 5518–5527 (1987): Baker et al., Science, Vol.. 244, p. 217 (1989); Fearon et al., Science, Vol. 247, p. 49 (1990); Kinzler et al. Science Vol. 251. p. 1366 (1991).)

In order to fully understand the pathogenesis of tumors, it will be necessary to identify the other suppressor genes that play a role in the tumorigenesis process. Prominent among these is the one(s) presumptively located at 5q21. Cytogenetie (Herrera et al., *Am J. Med. Genet.*, Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmoid tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research. Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in both sporadic and familial tumors.

Although the MCC gene has been identified on 5q21 as a candidate suppressor gene, it does not appear to be altered in F AP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lost said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object or the invention to provide a preparation of the human APC protein.

It is another object of the invention to provide a method of screening for genetic predisposition to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products frown the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provided for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene coding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in FIG. 3 or 7.

In yet another embodiment of the invention a method is provided for screening for genetic predisposition to cancer, including familial adenomatous polyposis (FAP) and Gardner's Syndrome (GS), in a human. The method comprises: detecting among kindred persons the presence of a DNA polymorphism which is linked to a mutant APC allele in an individual having a genetic predisposition to cancer, said kindred being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenic animals are provided. The animals carry a mutant APC allele from a second animal species or have been genetically engineered to contain an insertion mutation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colorectal cancers, Gardner's Syndrome, as well as the less severe familial polyposis discusses above.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

Figures 1, 1B, 2:
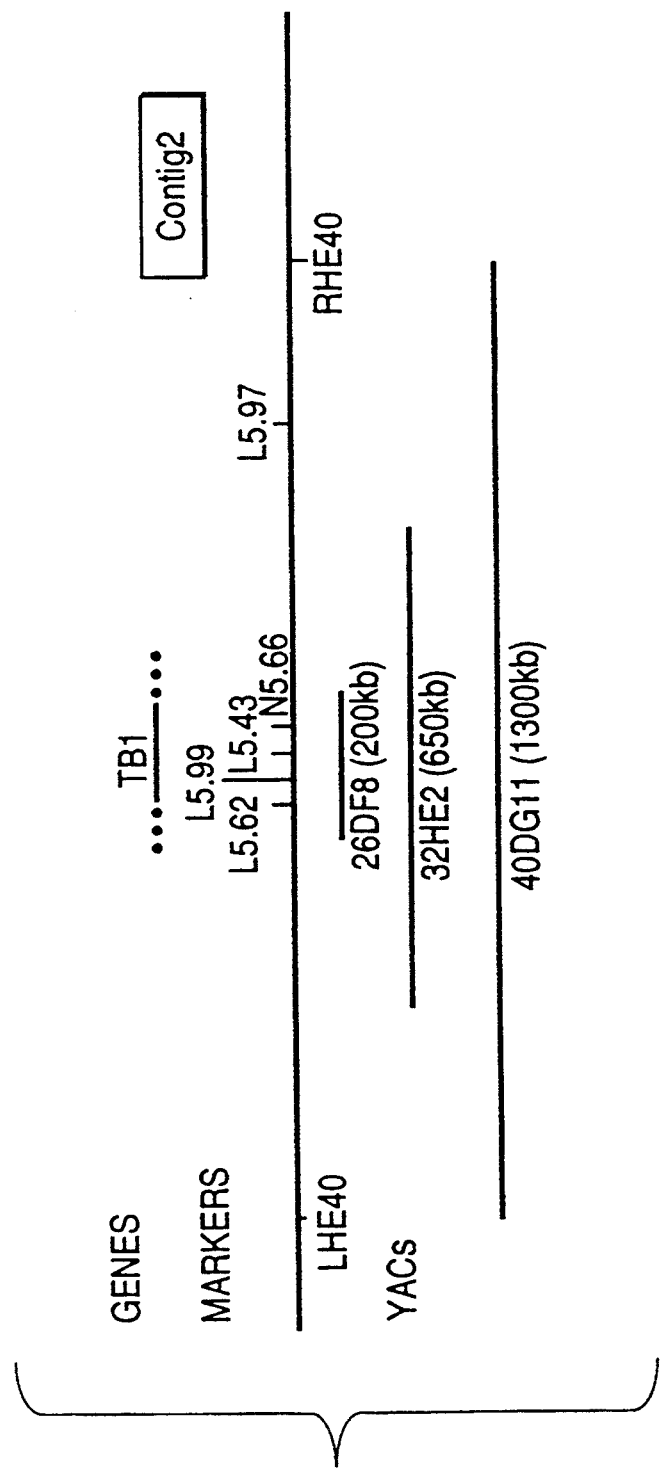
FIG. 1B shows a detailed map of the three central contigs. The position of the six identified genes from within the FAP region is shown; the 5' and 3' ends of the transcripts from these genes have in general not yet been isolated, as indicated by the string of dots surrounding the bars denoting the genes positions. Selected restriction endonuclease recognition sites are indicated. B, BssH2; S, SstII; M, MluI; N, NruI.
FIG. 2 shows the sequence of TB1 and TB2 genes. The cDNA sequence of the TB1 gene was determined from the analysis of 11 cDNA clones derived from normal colon and liver, as described in the text. A total of 2314 bp were contained within the overlapping cDNA clones, defining an ORF of 424 amino acids beginning at nucleotide 1. Only the predicted amino acids from the ORF are shown. The carboxy-terminal end of the ORF has apparently been identified, but the 5' end of the TB1 transcript has not yet been precisely determined.
Figures 1, 1B, 2, 3:
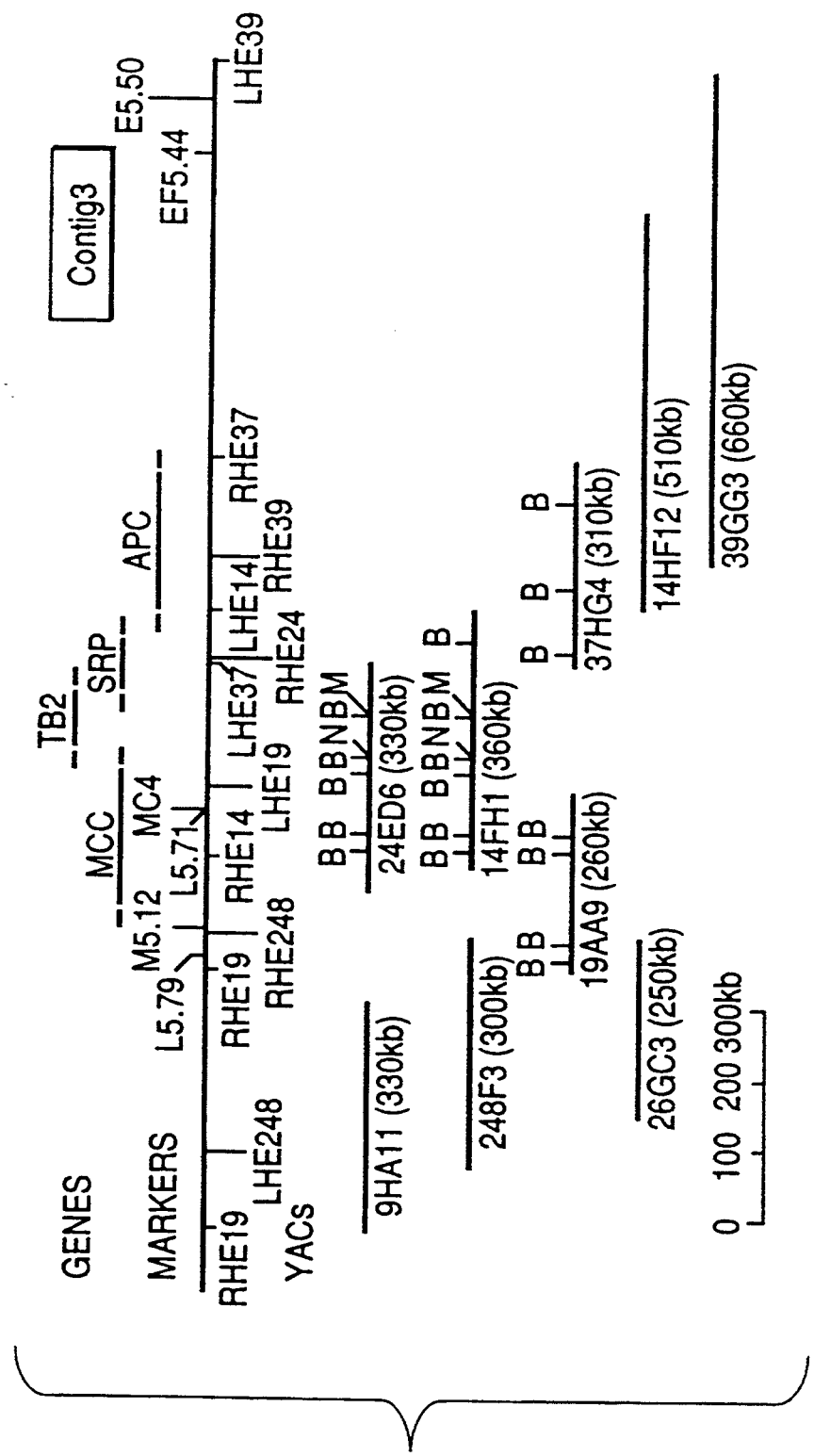

FIG. 3 shows the sequence of the APC gene product. The cDNA sequence was determined through the analysis of 87 cDNA clones derived from normal colon, liver, and brain. A total of 8973 bp were contained within overlapping cDNA clones, defining an ORF of 2842 amino acids. In frame stop codons surrounded this ORF, as described in the text, suggesting that the entire APC gene product was represented in the ORF illustrated. Only the predicted amino acids are shown.

FIG. 4 shows the local similarity between human APC and ral2 of yeast. Local similarity among the APC and MCC genes and the m3 muscarinic acetylcholine receptor is shown. The region of the mAChR shown corresponds to that responsible for coupling the receptor to G proteins. The connecting lines indicate identities; dots indicate related amino acids residues.

Figure 5:
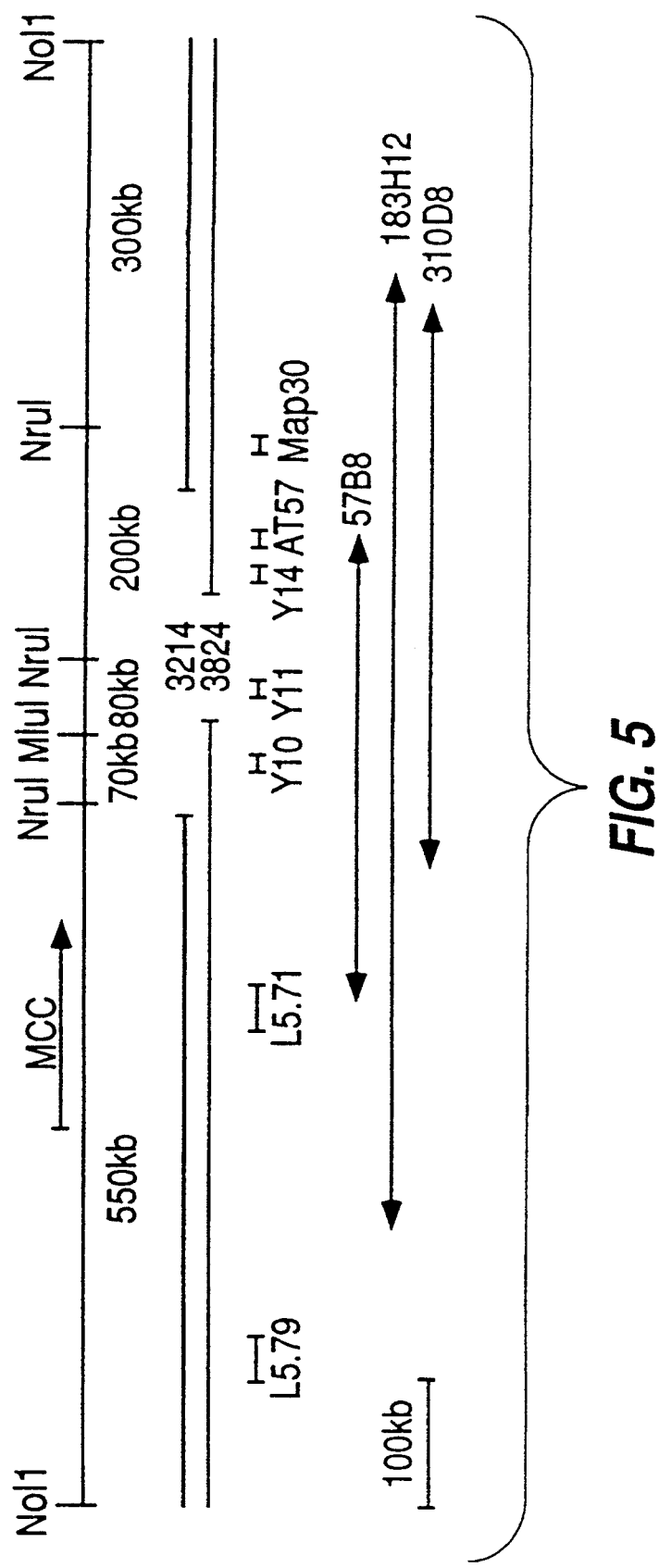

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are indicated above the map.

FIG. 6 shows the DNA sequence and predicted amino acid sequence of DP1 (TB2). The nucleotide numbering begins at the most 5' nucleotide isolated. A proposed initiation methionine (base 77) is indicated in bold type. The entire coding sequence is presented.

FIG. 7 shows the cDNA and predicted amino acid sequence of DP2.5 (APC), The nucleotide numbering begins at the proposed initiation methionine. The nucleotides and amino acids of the alternatively spliced exon (exon 9; nucleotide positions 934–1236) are presented in lower case letters. At the 3' end, a poly(A) addition signal occurs at 9530, and one cDNA clone has a poly(A) at 9563. Other cDNA clones extend beyond 9563, however, and their consensus sequence is included here.

Figure 8A:
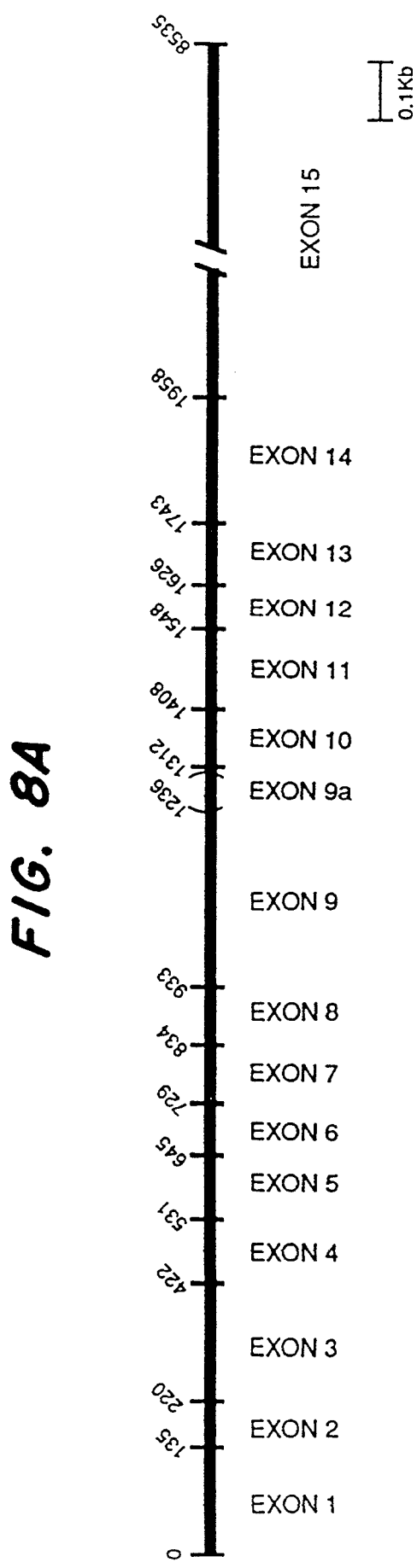
Figures 1, 8B:
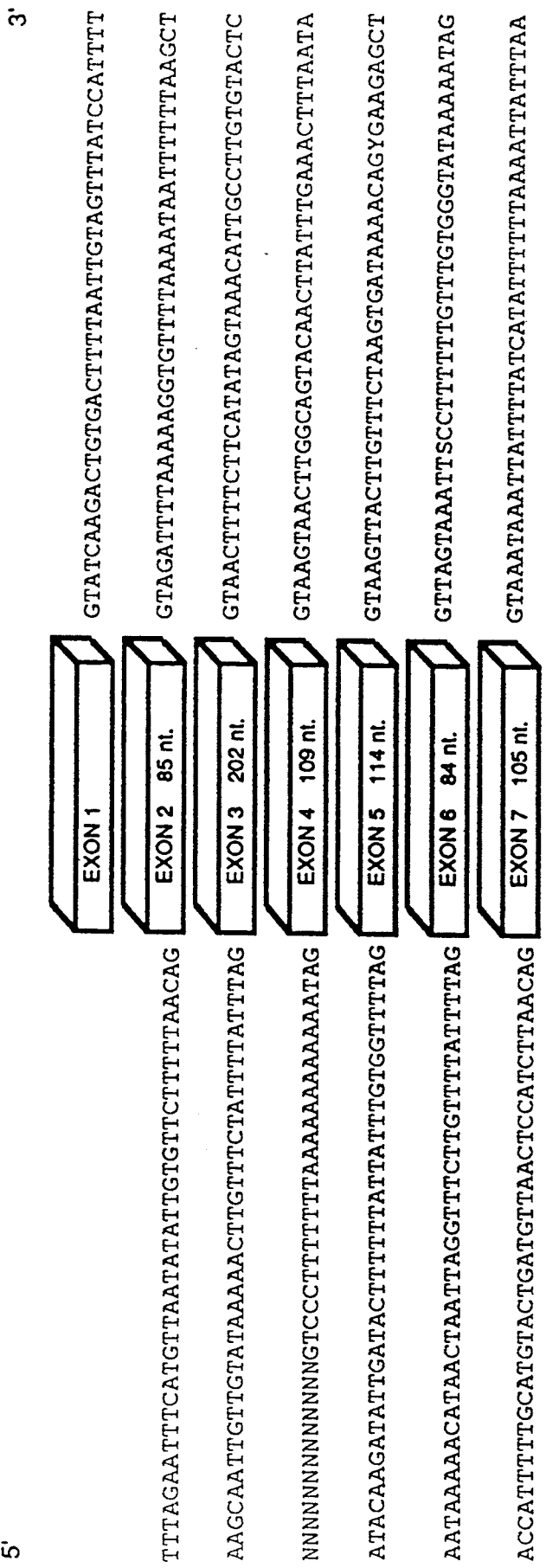
FIG. 1A shows an overview of yeast artificial chromosome (YAC) contigs (contiguous stretches of sequence). Genetic distances between selected RFLP markers from within the contigs are shown in centiMorgans.
Figures 2, 8B:
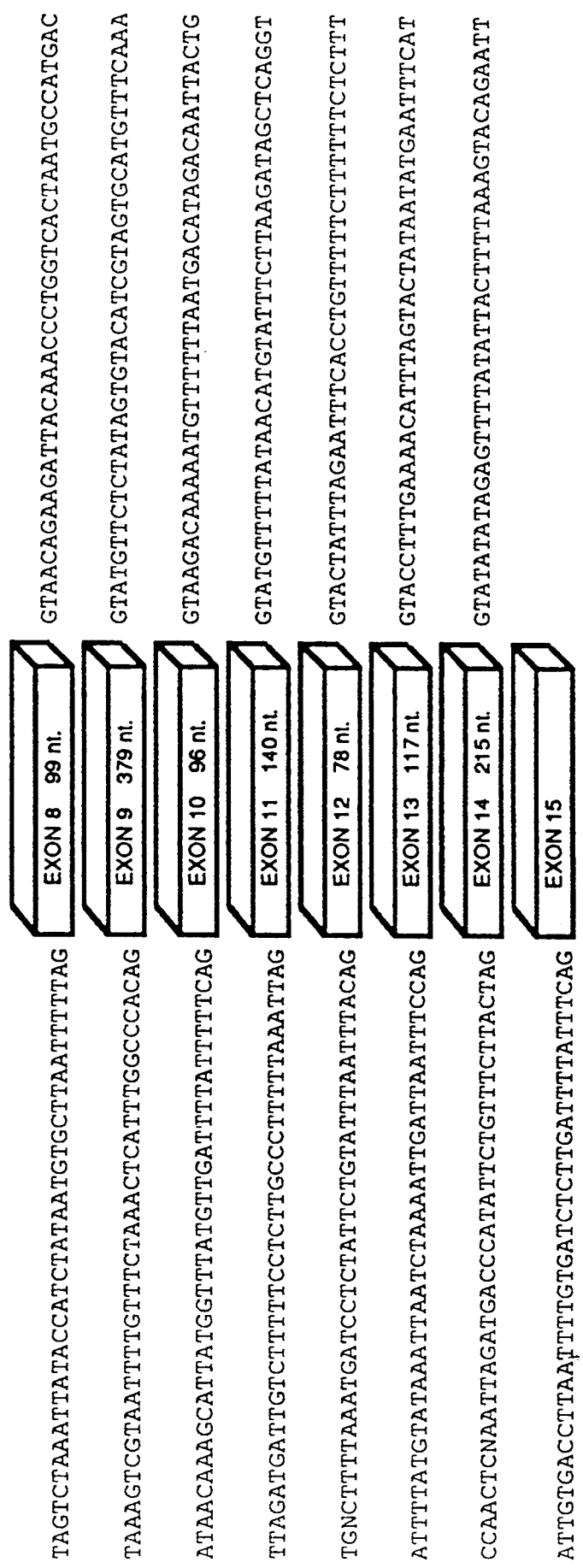

FIG. 8 shows the arrangement of exons in DP2.5 (APC), (A) Exon 9 corresponds to nucleotides 933–1312; exon 9a corresponds m nucleotides 1236–1312. The stop codon in the cDNA is at nucleotide 8535. (B) Partial intronic sequence surrounding each exon is shown.

DETAILED DESCRIPTION

It is a discovery of the present invention that mutational events associated with tumorigenesis occur in a previously unknown gene on chromosome 5q named here the APC (Adenomamus Polyposis Coli) gene. Although it was previously known that deletion of alleles on chromosome 5q were common in certain types of cancers, it was not known that a target gene of these deletions was the APC gene. Further it was not known that other types of mutational events in the APC gene are also associated with cancers, The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations—including deletions. The alteration may be due to either rearrangements such as insertions, inversions, and deletions, or to point mutations, Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatieally mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. No. 4,683,203; and U.S. Pat. No. 4,683,195. Specific primers which can be used in order to amplify the gene will be discussed in more detail below. The ligase chain reaction, which is known in the art, can also be used to amplify APC sequences. See Wu et al., *Genomics*, Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ALUMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindred persons of an affected individual for the presence of the APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Alteration of wild-type genes can also be detected on the basis of the alteration of a wild-type expression product of the gene. Such expression products include both the APC mRNA as well as the APC protein product. The sequences of these products are shown in FIGS. 3 and 7. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismateh detection can be used to detect point mutations in the gene or its mRNA product. While these techniques are less sensitive than sequencing, they are simpler to perform on a large number of tumor samples. An example of a mismateh cleavage technique is the RNase protection method, which is described in detail in Winter et al., Proc. Natl. Acad.

Sci. USA, Vol. 82, p. 7575, 1985 and Meyers et al., Science, Vol. 230, p. 1242, 1985. In the practice of the present invention the method involves the use of a labeled riboprobe which is complementary to the human wild-type AIsC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismateh is detected by RNase A, it cleaves at the site of the mismateh. Thus, when the annealed RNA preparation is separated on an electrophoretie gel matrix, if a mismateh has been detected and cleaved by RNase A, an RNA product will be seen which is smaller than the full-length duplex RNA for the riboprobe and the mRNA or DNA. The riboprobe need not be the full length of the ArC mRNA or gene but can be a segment of either. If the riboprobe comprises only a segment of the ArC mRNA or gene it will be desirable to use a number of these probes to screen the whole mRNA sequence for mismatehes.

In similar fashion, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretie mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the ArC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the APC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the rumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gone.

Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC genes or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene on chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonueleotide synthesizing machines which are commercially available. Given the sequence of the APC open reading frame shown in FIG. 7, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the APC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nucleic acid probes is used to compose a kit for detecting alteration of wild-type APC genes. The kit allows for hybridization to the entire APC gene. The probes may overlap with each other or be contiguous.

If a riboprobe is used to detect mismatches with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, colorimetic, or fluorometric material, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the APC gene. These are useful to detect similar mutations in other patients on the basis of hybridization rather than mismatches. These are discussed above and referred to as allele-specific probes. As mentioned above, the APC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes. Provided with the APC coding sequence shown in FIG. 7 (SEQ ID NO:1), design of particular probes is well within the skill of the ordinary artisan.

According to the present invention a method is also provided of supplying wild-type APC function to a cell which carries mutant APC alleles. Supplying such function should suppress neoplastic growth of the recipient cells. The wild-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes both for recombination and for extrachromosomal maintenance are known in the art and any suitable vector may be used. Methods for introducing DNA into cells such as electropotation, calcium phosphate co-precipitation and viral transduction are known in the art and the choice of method is within the competence of the routineer. Cells transformed with the wild-type APC gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed phenotype of the cell will be determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant APC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in FIG. 3 or 7 (SEQ ID NO:7 or 1). These two sequences differ slightly and appear to be indicate the existence of two different forms of the APC protein. Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or in vitro.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells, or amniotic fluid for mutations of the APC gene. Alteration of a wild-type APC allele, whether for example, by point mutation or by deletion, can be detected by any of the means discussed above.

Molecules of cDNA according to the present invention are intron-free, APC gene coding molecules. They can be made by reverse transcriptase using the APC mRNA as a template. These molecules can be propagated in vectors and cell lines as is known in the art. Such molecules have the sequence shown in SEQ ID NO: 7. The cDNA can also be made using the techniques of synthetic chemistry given the sequence disclosed herein.

A short region of homology has been identified between APC and the human m3 muscarinic acetylcholine receptor (mAChR). This chornology was largely confined to 29 residues in which 6 out of 7 amino acids (EL(GorA)GLQA) were identical (See FIG. 4). Initially, it was not known whether this homology was significant, because many other proteins had higher levels of global homology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mAChR at the analogous protein position. These 21 residues overlap the 19 amino acid homology between APC and m3 mAChR.

This connection between APC and the G protein activating region of mAChR is intriguing in light of previous investigations relating G proteins to cancer. For example, the RAS oneogenes, which are often mutated in colorectal cancers (Vogelstein, et al., N. Engl. J. Med., Vol. 319, p. 525 (1988); Bos et al., Nature Vol. 327, p. 293 (1987)), are members of the G protein family (Bourne, et al., Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, Vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindae. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg., 157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in normal colon cells and in colorectal, lung, and bladder tumors.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Three contigs encompassing approximately 4 Mb were contained within the central portion of this region. The YAC's constituting these contigs, together with the markers used for their isolation and orientations, are shown in FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in mierotiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleie Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACs. The termini of the 28EC1 YAC were sequenced to derive markers RHE28 and LHE28, respectively. The sequences of these two markers were then used to isolate YAC clones 15CH12 (from RHE28) and 40CF1 and 29EF1 (from LHE28). These five YAC's formed a config encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC 39GG3 allowed connection of the initial contig 3 clones through YAC 37HG4 (FIG. 1B).

Multipoint linkage analysis with the various markers used to define the contigs, combined with PFGE analysis, showed that contigs 1 and 2 were centromecic to contig 3. These contigs were used as tools to orient and/or identify genes which might be responsible for FAP. Six genes were found to lie within this cluster of YAC's, as follows:

Contig #1: FER - The FER gene was discovered through its homology to the vital oncogene ABL (Hao et al., supra). It has an intrinsic tyrosine kinase activity, and in situ hybridization with an FER probe showed that the gene was located at 5q11-23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human gertomit DNA. Thus, the YAC mapping results were consistent with the FER linkage data and PFGE analyses.

Contig 2:TB1 - TB1 was identified through a cross-hybridization approach. Exons of genes are often evolutionarily conserved while introns and intergenie regions are much less conserved. Thus, if a human probe cross-hybridizes strongly to the DNA from non-primate species, there is a reasonable chance that it contains exon sequences. Subclones of the cosraids shown in FIG. 1 were used to semen Southern blots containing rodent DNA samples. A subclone of cosmid N5.66 (p 5.66-4) was shown to strongly hybridize to rodent DNA, and this clone was used to semen cDNA libraries derived from normal adult colon and fetal liver. The ends of the initial eDNA clones obtained in this screen were then used to extend the eDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids. The product of this gene was not globally homologous to any other sequence in the current database but showed two significant local similarities to a family of ADP, ATP carrier/translocator proteins and mitochondrial brown fat uncoupling proteins which are widely distributed from yeast to mammals. These conserved regions of TB1 (underlined in FIG. 2A) may define a predictive motif for this sequence family. In addition, TB1 appeared to contain a signal peptide (or mitochondrial targeting sequence) as well as at least 7 transmembrane domains.

Conrig 3: MCC, TB2, SRP and APC - The MCC gene was also discovered through a cross-hybridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the coding region of MCC was approximately 50 kb proximal to the centromeric end of a 200 kb deletion found in an FAP patient. MCC cDNA probes detected a 10 kb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a cDNA library from normal colon. One of the cDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (FIG. 2B). The gene detected by YS39 was named TB2. Searches of nucleotide and protein databases revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. The gene corresponding to this transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14FH1. However, the 3' end of the APC gene was found in 14FH1 as well as 37HG4. Analogously, the 5' end of the MCC coding region was found in YAC clones 19AA9 and 26GC3 but not 24ED6 or 14FH1, while the 3' end displayed the opposite pattern. Thus, MCC and APC transcription units pointed in opposite directions, with the direction of transcription going from centromeric to telomeric in the case of MCC, and telomeric to centromeric in the case of APC. PFGE analysis of YAC DNA digested with various restriction endonucleases showed that TB2 and SRP were between MCC and APC, and that the 3' ends of the coding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain 2,842 amino acids (FIG. 3). The results of database searching with the APC gene product were quite complex due to the presence of large segments with locally biased amino acid compositions. In spite of this, APC could be roughly divided into two domains. The N-terminal 25% of the protein had a high content of leueine residues (12%) and showed local sequence similarities to myosins, various intermediate filament proteins (e.g., desrain, vimentin, neurofilaments) and Drosophila armadillo/human plakoglobin. The latter protein is a component of adhesive junctions (desmosomes) joining epithelial cells (Franke et al., Proc. Natl. Acad. Sci. U.S.A., Vol. 86, p. 4027 (1989); Perlet et al., Cell, Vol. 63, p. 1167 (1990)) The C-terminal 75% of APC (residues 731- 2832) is 17% serine by composition with setinc residues more or less uniformly distributed. This large domain also contains local concentrations of charged (mostly acidic) and proline residues. There was no indication of potential signal peptides, transmembrane regions, or nuclear targeting signals in APC, suggesting a cytoplasmic localization.

To detect short similarities to APC, a database search was performed using the PAM-40 matrix (Altsehul. J. Mol. Bio., Vol. 219, p. 555 (1991). Potentially interesting matches to several proteins were found. The most suggestive of these involved the ral2 gene product of yeast, which is implicated in the regulation of ras activity (Fukul et al., Mol. Cell. Biol., Vol. 9, p. 5617 (1989)). Little is known about how ral2 might interact with ras but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both are implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "spacer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of APC. The potential for both APC and MCC to form coiled coils is interesting in that such structures often mediate homo- and hetero-oligomerization.

Finally, it had previously been noted that MCC shared a short similarity with the region of the m3 muscarinic acetylcholine receptor (mAChR) known to regulate specificity of G-protein coupling. The APC gene also contained a local similarity to the region of the m3 mAChR that overlapped with the MCC similarity (FIG. 4B). Although the similarities to ral2 (FIG. 4A) and m3 mAChR (FIG. 4B) were not statistically significant, they were intriguing in light of previous observations relating G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER, TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-AGAAGGATCCCTTGT-GCAGTGTGGA-3' and 5'-GACAGGATCCT-GAAGCTGAGTTTG-3'. The underlined nucleotides were altered from the true FER sequence to create BamHI sites. The cell lines used were JW and Dill, both derived from colorectal cancers of FAP patients. (C. Paraskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequenced in their entirety. The PCR products were cloned in the BamHI site of Bluescript SK (Stratagene) and pools of at least 50 clones were sequenced en masse using T7 polymerase, as described in Nigro et al., Nature 342,705 (1989).

Only a single conservative amino acid change (GTG->CTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' and 5'-GGAATAATTAGGTCTCCAA-3'. PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and APC in FAP and sporadic rolorectal tumors. Each of these genes is linked and encompassed by conrig 3 (see FIG. 1).

Several lines of evidence suggested that this conrig was of particular interest. First, at least three of the four genes in this conrig were within the deleted region identified in two FAP patients. (See Example 5 infra.) Second, allelic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with sporadic CRC. Only two examples of somatic changes were observed in over 200 tumors studied: a rearrangement/deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of conrig 3 genes in patients with FAP. We chose to examine MCC and APC, rather than TB2 or SRP, because of the somatic mutations in MCC and APC noted above. To facilitate the identification of subtle alterations, the genomic sequences of MCC and APC exons were determined (see Table I). These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions. approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the APC gene. The three exons examined included those containing nt 822-930, 931-1309, and the first 300 nt of the most distal exon (nt 1956-2256). PCR and RNase protection analysis were performed as described in Kinzler et al. supra, using the primers underlined in Table I. The primers for nt 1956-2256 were 5'-GCAAATC-CTAAGAGAGAACAA-3' and 5'-GATG-GCAAGCTTGAGCCAG-3'.

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nueleic Acids Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demonstrated the same abnormal RNase protection pattern indicated that both had a C to T transition at codon 301 that resulted in a change from arginine (CGA) to a stop codon (TGA). This change was not present in 200 individuals without FAP. As this point mutation resulted in the predicted loss of the recognition site for the enzyme Taq I, appropriate PCR products could be digested with Taq I to detect the mutation. This allowed us to determine that the stop codon co-segregated with disease phenotype in members of the family of P24. The inheritance of this change in affected members of the pedigree provides additional evidence for the importance of the mutation.

Cloning and sequencing of the PCR product from FAP patient P93 indicated a C to G transversion at codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9. In addition to these germline mutations, we identified several somatic mutations of MCC and APC in sporadic CRC's. Seventeen MCC exons were examined in 90 sporadic colorectal cancers by RNase protection analysis. In each case where an abnormal RNase protection pattern was observed, the corresponding PCR products were cloned and sequenced. This led to the identification of six point mutations (two described previously) (Kinzler et al., supra), each of which was not found in the germline of these patients (Table IIB). Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822-930, 931-1309, and 1406-1545 (Table I). A total of three mutations were identified, each of which proved to be somatic. Tumor T27 contained a somatic mutation of C GA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codon (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Biochem. Biophys. Res. Comm. 130, 118 (1985). PCR was performed using the primers 5'-GTTCCAGCAGTGT-CACAG-3' and 5'-GGGAGATTTCGCTCCTGA-3'. APCR product containing codon 1338 was amplified from the archival DNA and used to show that the stop codon represented a somatic mutation present in the original primary tumor and in cell lines derived from the primary and metastatic tumor sites, but not from normal tissue of the patient.

The ten point mutations in the MCC and APC genes so far discovered in sporadic CRCs are summarized in Table IIB. Analysis of the number of mutant and wild-type PCR clones obtained from each of these tumors showed that in eight of the ten cases, the wild-type sequence was present in approximately equal proportions to the mutant. This was confirmed by RFLP analysis using flanking markers from chromosome 5q which demonstrated that only two of the ten tumors (T135 and T201) exhibited an allelic deletion on chromosome 5q. These results are consistent with previous observations showing that 20-40% of sporadic colorectal tumors had allelic deletions of chromosome 5q. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that had been mapped into a region near the APC locus to identify small deletions or rearrangements. Two of these cosmids, L5.71 and L5.79, hybridized with a 1200 kb NotI fragment in DNAs from most or the FAP patients screened.

The DNA of one FAP patient, 3214, showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb NotI fragment that was transmitted to her two unaffected offspring. These observations indicated that the mutant polyposis allele is on the same chromosome as the 940 kb NotI fragment. A simple interpretation is that APC patients 3214 and 4711 each carry a 260 kb deletion within the APC locus.

If a deletion were present, then other enzymes might also expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, MluI fragments in patients 3214 and 4711 also showed an increase in size consistent with the deletion of an MluI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 3214 showed only a 940 kb NotI fragment, she had not inherited the 1200 kb fragment present in the unaffected father's DNA. This observation suggests that he must be heterozygous for, and have transmitted, either a deletion of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were both found to lie on a 550 kb NotI-NruI fragment and, therefore, on the same side or an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHW141, which contains about 40% of chromosome 5, was digested with NotI and electrophoresed under pulsed-field gel (PFG) conditions; EcoRI fragments from the 1200 kb region of this gel were cloned into a phage vector. Probe Map30 was isolated from this library. In normal individuals probe Map30 hybridizes to the 1200 kb NotI fragment and to a 200 kb NruI fragment. This latter hybridization places Map30 disrat, with respect to the locations of L5.71 and L5.79, to the NruI site of the 550 kb NotI-NruI fragment.

Because Map30 hybridized to the abnormal, 1300 kb NruI fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and MluI did not reveal abnormal bands, indicating that if a deletion were present, its boundaries must lie distal to the NruI and MluI sites of the fragments identified by L5.79. Consistent with this expectation, hybridization of Map30 to DNA from patient 3824 identified a 760 kb MluI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb MluI fragment identified by Map30 is distinct from the 830 kb MluI fragment identified previously by L5.79 was demonstrated by hybridization of Map30 and L5.79 to a NotI-MluI double digest of DNA from the hybrid cell (HHW1159) containing the nondeleted chromosome 5 homolog of patient 3214. As previously indicated, this hybrid is interpreted as missing one of the NotI sites that define the 1200 kb fragment. A 620 kb NotI-MluI fragment was seen with probe L5.79, and an 860 kb fragment was seen witch Map30. Therefore, the 830 kb MluI fragment recognized by probe L5.79 must contain a NotI site in HHW1159 DNA; because the 860 kb MluI fragment remains intact, it does not carry this NotI site and must be distinct from the 830 kb MluI fragment.

EXAMPLE 5

This example demonstrates the isolation of human sequences which span the region deleted in the two unrelated FAP patients characterized in Example 4.

A strong prediction of the hypothesis that patients 3214 and 3824 carry deletions is that some sequences present on normal chromosome 5 homologs would be missing from the hypothesized deletion homologs. Therefore, to develop gertomit probes that might confirm the deletions, as well as to identify genes from the region, YAC clones from a conrig seeded by cosmid L5.79 were localized from a library containing seven haploid human genome equivalents (Albertsen et al., Proc. Natl. Acad. Sci. U.S.A., Vol. 87, pp. 4256–4260 (1990))with respect to the hypothesized deletions. Three clones, YACs 57B8, 310D8, and 183H12, were found to overlap the deleted region.

Importantly, one end of YAC 57B8 (clone AT57) was found to lie within the patient 3214 deletion. Inverse polymerase chain reaction (PCR) defined the end sequences of the insert of YAC 57B8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHW1159) carrying the normal chromosome 5 homolog. This result supported the interpretation that the abnormal restriction fragments found in the DNA of patient 3214 result from a deletion.

Additional support for the hypothesis of deletion in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoR1 fragments from YAC 183H12, Y10 and Y14, were localized within the patient 3214 deletion by their failure to hybridizie to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-MluI fragment seen with probe L5.79 in normal DNA, indicating its location as L5.79-proximal to the deleted MluI site and placing it between the MluI site and the L5.79-proximal NruI site. The MluI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 kb NotI-MluI fragment, placing it L5.79-distal to the MluI site, but proximal to the second NruI site. Hybridization to the same (860 kb) MluI fragment as Map30 confirmed the localization of probe Y11 L5.79-distal to the MluI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and deleted in patient 3214, with respect to L5.79 and Map30, is L5.79-Y10-Y11-Y14-Map30.

The 100 kb deletion of patient 3824 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the MluI digest, probe Y14 hybridized to the 860 kb and 760 kb fragments of patient 3824 DNA, but probe Y11 hybridized only to the 860 kb fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations. therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (Kinzler et al., supra). It was therefore of interest to map this gene with respect to the deletions in FAP patients. Hybridization of MCC probes with an overlapping series of YAC clones extending in either direction from L5.71 showed that the 3' end of MCC must be oriented toward the region of the two FAP deletions.

Therefore, two 3' cDNA clones from MCC were mapped with respect to the deletions: clone 1CI (bp 2378-4181) and clone 7 (bp 2890-3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the cDNA clones consists of a single 2.5 kb exon. These two clones were hybridized to DNAs from the YACs spanning the FAP region. Clone 7 fails to hybridize to YAC 310D8, although it does hybridize to YACs 183H12 and 5738; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone contig is likely to be located more than 45 kb from the deletion of patient 3214 and, therefore, more than 100 kb from the deletion of patient 3824.

EXAMPLE 7

This example identifies three genes within the deleted region of chromosome 5 in the two unrelated FAP patients characterized in Example 4.

Genomic clones were used to semen cDNA libraries in three separate experiments. One screening was done with a phage clone derived from YAC 310D8 known to span the 260 kb deletion of patient 3214. A large-insert phage library was constructed from this YAC; screening with Y11 identified λ205, which mapped within both deletions. When clone λ205 was used to probe a random-, plus oligo(dT)-, primed fetal brain cDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above.

cDNA walks yielded a cDNA conrig of 3.0-3.5 kb, and included two clones containing terminal poly(A) sequences. This size corresponds to the 3.5 kb band seen by Northern analysis. Sequencing of the first 3163 bp of the cDNA conrig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the $NH_2$-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle. SRP19 (Lingelbach et al., supra). Hybridization experiments mapped YS-11 within both deletions. The sequence of this clone, however, was found to be complex. Although 454 bp of the 1032 bp sequence of YS-11 were identical to the GenBank entry for the SRP19 gene. another 578 bp appended 5' to the SRP19 sequence was found to consist of previously unreported sequence containing no extended open reading frames. This suggested that YS-11 was either a chimeric clone containing two independent inserts or a clone of an incompletely processed or aberrant message. If YS-11 were a conventional chimeric clone, the independent segments would not be expected to map to the same physical region. The segments resulting from anomalous processing of a continuous transcript, however, would map to a single chromosomai region.

Inverse PCR with primers specific to the two ends of YS-11, the SRP19 end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomic sequence was also seen after these 78 bp, suggesting the presence of a splice junction, and supporting the view that YS-11 represents an irregular message.

Starting with V5, successive 5' and 3' walks were performed; the resulting cDNA contig consisted of more than 100 clones, which defined a new transcript, DP2. Clones walking in the 5' direction crossed the 3824 deletion breakpoint farthest from L5.71; since its 3' end is closer to this cosmid than its 5' end, the transcriptional orientation of DP2 is opposite to that of MCC and DP1.

The third screening approach relied on hybridization with a 120 kb MluI fragment from YAC 57B8. This fragment hybridizes with probe Y11 and completely spans the 100 kb deletion in patient 3824. the fragment was purified on two preparative PFGs, labeled, and used to screen a fetal brain cDNA library. A number of cDNA clones previously identified in the development of the DP1 and DP2 configs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 7.

The consensus cDNA sequence of DP2.5 suggests that the entire coding sequence of DP2.5 has been obtained and is 8532 bp long. The most 5' ATG codon occurs two codons from an in-frame stop and conforms to the Kozak initiation consensus (Kozak, Nucl. Acids. Res., Vol. 12, p. 857-872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to that identified as APC above.

An alternatively spliced exon at nucleotide 934 of the DP2.5 transcript is of potential interest. it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP2.5.

To obtain DNA sequence adjacent to the exons of the genes DP1, DP2.5, and SRP19, sequencing substrate was obtained by inverse PCR amplification of DNAs from two YACs, 310D8 and 183H12, that span the deletions. Ligation at low concentration cyclized the restriction enzyme-digested YAC DNAs. Oligonucleotides with sequencing tails, designed in inverse orientation at intervals along the cDNAs, primed PCR amplification from the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table III. With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences. The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250-400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766-70 (1989) and Genomies, Vol. 5, pp. 874-879 (1989) as applied to DP1, SRP19 and DP2.5.

SSCP analysis identifies most single- or multiple-base changes in DNA fragments up to 400 bases in length. Sequence alterations are detected as shifts in eleetrophoretie mobility of single-stranded DNA on nondenaturing aerylamide gels; the two complementary strands of a DNA segment usually resolve as two SSCP conformers of distinct mobilities. However, if the sample is from an individual heterozygous for a base-pair variant within the amplified segment, often three or more bands are seen. In some eases, even the sample from a homozygous individual will show multiple bands. Base-pair-change variants are identified by differences in pattern among the DNAs of the sample set.

Exons of the candidate genes were amplified by PCR from the DNAs of 61 related FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15 of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobillties. The normal conformers from the host individuals were sequenced also. Bands were cut from the dried acrylamide gels, and the DNA was eluted. PCR amplification of these DNAs provided template for sequencing.

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain a deletion of two adjacent nucleotides, at positions 730 and 731 in the cDNA sequence (FIG. 7). The normal sequence at this splice junction is CAGGGTCA (intronic sequence underlined), with the intron-exon boundary between the two repetitions of AG. The mutant allele in this patient has the sequence CAGGTCA. Although this exchange is at the 5' splice site, comparison with known consensus sequences of splice junctions would suggest that a functional splice junction is maintained. If this new splice junction were functional, the mutation would introduce a frameshift that creates a stop codon 15 nueleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient 3746 is heterozygous for a 2 bp deletion.

The unique conformer found in exon 8 of patient 3460 was found to carry a C-T transition, at position 904 in the cDNA sequence of DP2.5 (shown in FIG. 7), which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleotide (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an acrylamide-urea denaturing along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position 1500, changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the patient's parents displayed the normal pattern of conformers for exon 7, as did DNA from the patients's wife and one of his offspring. The two other children, however, displayed the same new conformers as their affected father. Testing of the patient and his parents with highly polymorphic VNTR (variable number of tandem repeat) markers showed a 99.98% likelihood that they are his biological parents.

These observations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene: first, in exon 11, at position 1458, a substitution of T to C creating an RsaI restriction site but no amino acid change; and second, in exon 15, at positions 5037 and 5271, substitutions of A to G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated.

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomic template. Two forms of exon 9 were found in DP2.5: one is the complete exon; and the other, labeled exon 9A, is the result of a splice into the interior of the exon that deletes bases 934 to 1236 in the mRNA and removes 101 amino acids from the predicted protein (see FIG. 7).

EXAMPLE 13

This example demonstrates the mapping of the FAP deletions with respect to the APC exons.

Somatic cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomic DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatic cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be assessed. All tissue types tested (brain, lung, aorta, spleen, heart, kidney, liver, stomach, placenta, and eolonie mueosa) and cultured cell lines (lymphoblasts, HL60, and ehorioeareinoma) expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistent with the size of the sequenced cDNA.

EXAMPLE 15

This example discusses structural features of the APC protein predicted from the sequence.

The cDNA consensus sequence of APC predicts that the longer, more abundant form of the message codes for a 2842 or 28444 amino acid peptide with a mass of 311.8 kd. This predicted APC peptide was compared with the current data bases of protein and DNA sequences using both Intelligenetics and GCG software packages. No genes with a high degree of amino acid sequence similarity were found. Although many short (approximately 20 amino acid) regions of sequence similarity were uncovered, none was sufficiently strong to reveal which, if any, might represent functional hornology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132 (1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem, Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table 4). The intervening sequences between the seven repeat regions contained 114, 116, 151, 205, 107, and 58 amino acids, respectively. Finally, residues 2200–24000 contain a 200 amino acid basic domain.

---

SEQUENCE LISTING ( 1 ) GENERAL INFORMATION:

( i i i ) NUMBER OF SEQUENCES: 94

( 2 ) INFORMATION FOR SEQ ID NO:1:

( i ) SEQUENCE CHARACTERISTICS:
        ( A ) LENGTH: 9606 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP2.5(APC)

( i x ) FEATURE:
        ( A ) NAME/KEY: CDS
        ( B ) LOCATION: 34..8562

( x i ) SEQUENCE DESCRIPTION: SEQ ID NO:1:

```
GGACTCGGAA ATGAGGTCCA AGGGTAGCCA AGG ATG GCT GCA GCT TCA TAT GAT         54
                                    Met Ala Ala Ala Ser Tyr Asp
                                     1               5

CAG TTG TTA AAG CAA GTT GAG GCA CTG AAG ATG GAG AAC TCA AAT CTT         102
Gln Leu Leu Lys Gln Val Glu Ala Leu Lys Met Glu Asn Ser Asn Leu
         10                  15                  20

CGA CAA GAG CTA GAA GAT AAT TCC AAT CAT CTT ACA AAA CTG GAA ACT         150
Arg Gln Glu Leu Glu Asp Asn Ser Asn His Leu Thr Lys Leu Glu Thr
     25                  30                  35

GAG GCA TCT AAT ATG AAG GAA GTA CTT AAA CAA CTA CAA GGA AGT ATT         198
Glu Ala Ser Asn Met Lys Glu Val Leu Lys Gln Leu Gln Gly Ser Ile
 40                  45                  50                  55
```

| | | | | | | | | | | | | | | | | |
|---|---|---|---|---|---|---|---|---|---|---|---|---|---|---|---|---|
| GAA | GAT | GAA | GCT | ATG | GCT | TCT | TCT | GGA | CAG | ATT | GAT | TTA | TTA | GAG | CGT | 246 |
| Glu | Asp | Glu | Ala | Met | Ala | Ser | Ser | Gly | Gln | Ile | Asp | Leu | Leu | Glu | Arg | |
| | | | 60 | | | | | 65 | | | | | 70 | | | |
| CTT | AAA | GAG | CTT | AAC | TTA | GAT | AGC | AGT | AAT | TTC | CCT | GGA | GTA | AAA | CTG | 294 |
| Leu | Lys | Glu | Leu | Asn | Leu | Asp | Ser | Ser | Asn | Phe | Pro | Gly | Val | Lys | Leu | |
| | | | 75 | | | | | 80 | | | | | 85 | | | |
| CGG | TCA | AAA | ATG | TCC | CTC | CGT | TCT | TAT | GGA | AGC | CGG | GAA | GGA | TCT | GTA | 342 |
| Arg | Ser | Lys | Met | Ser | Leu | Arg | Ser | Tyr | Gly | Ser | Arg | Glu | Gly | Ser | Val | |
| | | 90 | | | | | 95 | | | | | 100 | | | | |
| TCA | AGC | CGT | TCT | GGA | GAG | TGC | AGT | CCT | GTT | CCT | ATG | GGT | TCA | TTT | CCA | 390 |
| Ser | Ser | Arg | Ser | Gly | Glu | Cys | Ser | Pro | Val | Pro | Met | Gly | Ser | Phe | Pro | |
| | | 105 | | | | | 110 | | | | | 115 | | | | |
| AGA | AGA | GGG | TTT | GTA | AAT | GGA | AGC | AGA | GAA | AGT | ACT | GGA | TAT | TTA | GAA | 438 |
| Arg | Arg | Gly | Phe | Val | Asn | Gly | Ser | Arg | Glu | Ser | Thr | Gly | Tyr | Leu | Glu | |
| 120 | | | | | 125 | | | | | 130 | | | | | 135 | |
| GAA | CTT | GAG | AAA | GAG | AGG | TCA | TTG | CTT | CTT | GCT | GAT | CTT | GAC | AAA | GAA | 486 |
| Glu | Leu | Glu | Lys | Glu | Arg | Ser | Leu | Leu | Leu | Ala | Asp | Leu | Asp | Lys | Glu | |
| | | | | 140 | | | | | 145 | | | | | 150 | | |
| GAA | AAG | GAA | AAA | GAC | TGG | TAT | TAC | GCT | CAA | CTT | CAG | AAT | CTC | ACT | AAA | 534 |
| Glu | Lys | Glu | Lys | Asp | Trp | Tyr | Tyr | Ala | Gln | Leu | Gln | Asn | Leu | Thr | Lys | |
| | | | 155 | | | | | 160 | | | | | 165 | | | |
| AGA | ATA | GAT | AGT | CTT | CCT | TTA | ACT | GAA | AAT | TTT | TCC | TTA | CAA | ACA | GAT | 582 |
| Arg | Ile | Asp | Ser | Leu | Pro | Leu | Thr | Glu | Asn | Phe | Ser | Leu | Gln | Thr | Asp | |
| | | 170 | | | | | 175 | | | | | 180 | | | | |
| TTG | ACC | AGA | AGG | CAA | TTG | GAA | TAT | GAA | GCA | AGG | CAA | ATC | AGA | GTT | GCG | 630 |
| Leu | Thr | Arg | Arg | Gln | Leu | Glu | Tyr | Glu | Ala | Arg | Gln | Ile | Arg | Val | Ala | |
| | 185 | | | | | 190 | | | | | 195 | | | | | |
| ATG | GAA | GAA | CAA | CTA | GGT | ACC | TGC | CAG | GAT | ATG | GAA | AAA | CGA | GCA | CAG | 678 |
| Met | Glu | Glu | Gln | Leu | Gly | Thr | Cys | Gln | Asp | Met | Glu | Lys | Arg | Ala | Gln | |
| 200 | | | | | 205 | | | | | 210 | | | | | 215 | |
| CGA | AGA | ATA | GCC | AGA | ATT | CAG | CAA | ATC | GAA | AAG | GAC | ATA | CTT | CGT | ATA | 726 |
| Arg | Arg | Ile | Ala | Arg | Ile | Gln | Gln | Ile | Glu | Lys | Asp | Ile | Leu | Arg | Ile | |
| | | | | 220 | | | | | 225 | | | | | 230 | | |
| CGA | CAG | CTT | TTA | CAG | TCC | CAA | GCA | ACA | GAA | GCA | GAG | AGG | TCA | TCT | CAG | 774 |
| Arg | Gln | Leu | Leu | Gln | Ser | Gln | Ala | Thr | Glu | Ala | Glu | Arg | Ser | Ser | Gln | |
| | | | 235 | | | | | 240 | | | | | 245 | | | |
| AAC | AAG | CAT | GAA | ACC | GGC | TCA | CAT | GAT | GCT | GAG | CGG | CAG | AAT | GAA | GGT | 822 |
| Asn | Lys | His | Glu | Thr | Gly | Ser | His | Asp | Ala | Glu | Arg | Gln | Asn | Glu | Gly | |
| | | 250 | | | | | 255 | | | | | 260 | | | | |
| CAA | GGA | GTG | GGA | GAA | ATC | AAC | ATG | GCA | ACT | TCT | GGT | AAT | GGT | CAG | GGT | 870 |
| Gln | Gly | Val | Gly | Glu | Ile | Asn | Met | Ala | Thr | Ser | Gly | Asn | Gly | Gln | Gly | |
| | 265 | | | | | 270 | | | | | 275 | | | | | |
| TCA | ACT | ACA | CGA | ATG | GAC | CAT | GAA | ACA | GCC | AGT | GTT | TTG | AGT | TCT | AGT | 918 |
| Ser | Thr | Thr | Arg | Met | Asp | His | Glu | Thr | Ala | Ser | Val | Leu | Ser | Ser | Ser | |
| 280 | | | | | 285 | | | | | 290 | | | | | 295 | |
| AGC | ACA | CAC | TCT | GCA | CCT | CGA | AGG | CTG | ACA | AGT | CAT | CTG | GGA | ACC | AAG | 966 |
| Ser | Thr | His | Ser | Ala | Pro | Arg | Arg | Leu | Thr | Ser | His | Leu | Gly | Thr | Lys | |
| | | | | 300 | | | | | 305 | | | | | 310 | | |
| GTG | GAA | ATG | GTG | TAT | TCA | TTG | TTG | TCA | ATG | CTT | GGT | ACT | CAT | GAT | AAG | 1014 |
| Val | Glu | Met | Val | Tyr | Ser | Leu | Leu | Ser | Met | Leu | Gly | Thr | His | Asp | Lys | |
| | | | 315 | | | | | 320 | | | | | 325 | | | |
| GAT | GAT | ATG | TCG | CGA | ACT | TTG | CTA | GCT | ATG | TCT | AGC | TCC | CAA | GAC | AGC | 1062 |
| Asp | Asp | Met | Ser | Arg | Thr | Leu | Leu | Ala | Met | Ser | Ser | Ser | Gln | Asp | Ser | |
| | | 330 | | | | | 335 | | | | | 340 | | | | |
| TGT | ATA | TCC | ATG | CGA | CAG | TCT | GGA | TGT | CTT | CCT | CTC | CTC | ATC | CAG | CTT | 1110 |
| Cys | Ile | Ser | Met | Arg | Gln | Ser | Gly | Cys | Leu | Pro | Leu | Leu | Ile | Gln | Leu | |
| | | 345 | | | | | 350 | | | | | 355 | | | | |
| TTA | CAT | GGC | AAT | GAC | AAA | GAC | TCT | GTA | TTG | TTG | GGA | AAT | TCC | CGG | GGC | 1158 |
| Leu | His | Gly | Asn | Asp | Lys | Asp | Ser | Val | Leu | Leu | Gly | Asn | Ser | Arg | Gly | |
| 360 | | | | | 365 | | | | | 370 | | | | | 375 | |
| AGT | AAA | GAG | GCT | CGG | GCC | AGG | GCC | AGT | GCA | GCA | CTC | CAC | AAC | ATC | ATT | 1206 |

|  |  |  |  |  |  |  |  |  |  |  |  |  |  |  |  |
|---|---|---|---|---|---|---|---|---|---|---|---|---|---|---|---|
| Ser | Lys | Glu | Ala | Arg 380 | Ala | Arg | Ala | Ser 385 | Ala | Ala | Leu | His | Asn | Ile 390 | Ile |

| CAC | TCA | CAG | CCT | GAT | GAC | AAG | AGA | GGC | AGG | CGT | GAA | ATC | CGA | GTC | CTT | 1254 |
|---|---|---|---|---|---|---|---|---|---|---|---|---|---|---|---|---|
| His | Ser | Gln | Pro 395 | Asp | Asp | Lys | Arg | Gly 400 | Arg | Arg | Glu | Ile | Arg 405 | Val | Leu |  |

| CAT | CTT | TTG | GAA | CAG | ATA | CGC | GCT | TAC | TGT | GAA | ACC | TGT | TGG | GAG | TGG | 1302 |
|---|---|---|---|---|---|---|---|---|---|---|---|---|---|---|---|---|
| His | Leu | Leu 410 | Glu | Gln | Ile | Arg | Ala | Tyr 415 | Cys | Glu | Thr | Cys | Trp 420 | Glu | Trp |  |

| CAG | GAA | GCT | CAT | GAA | CCA | GGC | ATG | GAC | CAG | GAC | AAA | AAT | CCA | ATG | CCA | 1350 |
|---|---|---|---|---|---|---|---|---|---|---|---|---|---|---|---|---|
| Gln | Glu | Ala | His 425 | Glu | Pro | Gly | Met | Asp 430 | Gln | Asp | Lys | Asn | Pro 435 | Met | Pro |  |

| GCT | CCT | GTT | GAA | CAT | CAG | ATC | TGT | CCT | GCT | GTG | TGT | GTT | CTA | ATG | AAA | 1398 |
|---|---|---|---|---|---|---|---|---|---|---|---|---|---|---|---|---|
| Ala 440 | Pro | Val | Glu | His | Gln 445 | Ile | Cys | Pro | Ala | Val 450 | Cys | Val | Leu | Met | Lys 455 |  |

| CTT | TCA | TTT | GAT | GAA | GAG | CAT | AGA | CAT | GCA | ATG | AAT | GAA | CTA | GGG | GGA | 1446 |
|---|---|---|---|---|---|---|---|---|---|---|---|---|---|---|---|---|
| Leu | Ser | Phe | Asp | Glu 460 | Glu | His | Arg | His | Ala 465 | Met | Asn | Glu | Leu | Gly 470 | Gly |  |

| CTA | CAG | GCC | ATT | GCA | GAA | TTA | TTG | CAA | GTG | GAC | TGT | GAA | ATG | TAT | GGG | 1494 |
|---|---|---|---|---|---|---|---|---|---|---|---|---|---|---|---|---|
| Leu | Gln | Ala | Ile 475 | Ala | Glu | Leu | Leu | Gln 480 | Val | Asp | Cys | Glu | Met 485 | Tyr | Gly |  |

| CTT | ACT | AAT | GAC | CAC | TAC | AGT | ATT | ACA | CTA | AGA | CGA | TAT | GCT | GGA | ATG | 1542 |
|---|---|---|---|---|---|---|---|---|---|---|---|---|---|---|---|---|
| Leu | Thr | Asn 490 | Asp | His | Tyr | Ser | Ile 495 | Thr | Leu | Arg | Arg | Tyr 500 | Ala | Gly | Met |  |

| GCT | TTG | ACA | AAC | TTG | ACT | TTT | GGA | GAT | GTA | GCC | AAC | AAG | GCT | ACG | CTA | 1590 |
|---|---|---|---|---|---|---|---|---|---|---|---|---|---|---|---|---|
| Ala | Leu 505 | Thr | Asn | Leu | Thr | Phe 510 | Gly | Asp | Val | Ala | Asn 515 | Lys | Ala | Thr | Leu |  |

| TGC | TCT | ATG | AAA | GGC | TGC | ATG | AGA | GCA | CTT | GTG | GCC | CAA | CTA | AAA | TCT | 1638 |
|---|---|---|---|---|---|---|---|---|---|---|---|---|---|---|---|---|
| Cys 520 | Ser | Met | Lys | Gly | Cys 525 | Met | Arg | Ala | Leu | Val 530 | Ala | Gln | Leu | Lys | Ser 535 |  |

| GAA | AGT | GAA | GAC | TTA | CAG | CAG | GTT | ATT | GCA | AGT | GTT | TTG | AGG | AAT | TTG | 1686 |
|---|---|---|---|---|---|---|---|---|---|---|---|---|---|---|---|---|
| Glu | Ser | Glu | Asp | Leu 540 | Gln | Gln | Val | Ile | Ala 545 | Ser | Val | Leu | Arg | Asn 550 | Leu |  |

| TCT | TGG | CGA | GCA | GAT | GTA | AAT | AGT | AAA | AAG | ACG | TTG | CGA | GAA | GTT | GGA | 1734 |
|---|---|---|---|---|---|---|---|---|---|---|---|---|---|---|---|---|
| Ser | Trp | Arg | Ala 555 | Asp | Val | Asn | Ser | Lys 560 | Lys | Thr | Leu | Arg | Glu 565 | Val | Gly |  |

| AGT | GTG | AAA | GCA | TTG | ATG | GAA | TGT | GCT | TTA | GAA | GTT | AAA | AAG | GAA | TCA | 1782 |
|---|---|---|---|---|---|---|---|---|---|---|---|---|---|---|---|---|
| Ser | Val | Lys 570 | Ala | Leu | Met | Glu | Cys 575 | Ala | Leu | Glu | Val | Lys 580 | Lys | Glu | Ser |  |

| ACC | CTC | AAA | AGC | GTA | TTG | AGT | GCC | TTA | TGG | AAT | TTG | TCA | GCA | CAT | TGC | 1830 |
|---|---|---|---|---|---|---|---|---|---|---|---|---|---|---|---|---|
| Thr | Leu 585 | Lys | Ser | Val | Leu | Ser 590 | Ala | Leu | Trp | Asn | Leu 595 | Ser | Ala | His | Cys |  |

| ACT | GAG | AAT | AAA | GCT | GAT | ATA | TGT | GCT | GTA | GAT | GGT | GCA | CTT | GCA | TTT | 1878 |
|---|---|---|---|---|---|---|---|---|---|---|---|---|---|---|---|---|
| Thr 600 | Glu | Asn | Lys | Ala | Asp 605 | Ile | Cys | Ala | Val | Asp 610 | Gly | Ala | Leu | Ala | Phe 615 |  |

| TTG | GTT | GGC | ACT | CTT | ACT | TAC | CGG | AGC | CAG | ACA | AAC | ACT | TTA | GCC | ATT | 1926 |
|---|---|---|---|---|---|---|---|---|---|---|---|---|---|---|---|---|
| Leu | Val | Gly | Thr | Leu 620 | Thr | Tyr | Arg | Ser | Gln 625 | Thr | Asn | Thr | Leu | Ala 630 | Ile |  |

| ATT | GAA | AGT | GGA | GGT | GGG | ATA | TTA | CGG | AAT | GTG | TCC | AGC | TTG | ATA | GCT | 1974 |
|---|---|---|---|---|---|---|---|---|---|---|---|---|---|---|---|---|
| Ile | Glu | Ser | Gly 635 | Gly | Gly | Ile | Leu | Arg 640 | Asn | Val | Ser | Ser | Leu 645 | Ile | Ala |  |

| ACA | AAT | GAG | GAC | CAC | AGG | CAA | ATC | CTA | AGA | GAG | AAC | AAC | TGT | CTA | CAA | 2022 |
|---|---|---|---|---|---|---|---|---|---|---|---|---|---|---|---|---|
| Thr | Asn | Glu 650 | Asp | His | Arg | Gln | Ile 655 | Leu | Arg | Glu | Asn | Asn 660 | Cys | Leu | Gln |  |

| ACT | TTA | TTA | CAA | CAC | TTA | AAA | TCT | CAT | AGT | TTG | ACA | ATA | GTC | AGT | AAT | 2070 |
|---|---|---|---|---|---|---|---|---|---|---|---|---|---|---|---|---|
| Thr | Leu 665 | Leu | Gln | His | Leu | Lys 670 | Ser | His | Ser | Leu | Thr 675 | Ile | Val | Ser | Asn |  |

| GCA | TGT | GGA | ACT | TTG | TGG | AAT | CTC | TCA | GCA | AGA | AAT | CCT | AAA | GAC | CAG | 2118 |
|---|---|---|---|---|---|---|---|---|---|---|---|---|---|---|---|---|
| Ala 680 | Cys | Gly | Thr | Leu | Trp 685 | Asn | Leu | Ser | Ala | Arg 690 | Asn | Pro | Lys | Asp | Gln 695 |  |

| GAA | GCA | TTA | TGG | GAC | ATG | GGG | GCA | GTT | AGC | ATG | CTC | AAG | AAC | CTC | ATT | 2166 |
|---|---|---|---|---|---|---|---|---|---|---|---|---|---|---|---|---|
| Glu | Ala | Leu | Trp | Asp 700 | Met | Gly | Ala | Val | Ser 705 | Met | Leu | Lys | Asn | Leu 710 | Ile |  |

| | | | | | | | | | | | | | | | | |
|---|---|---|---|---|---|---|---|---|---|---|---|---|---|---|---|---|
| CAT | TCA | AAG | CAC | AAA | ATG | ATT | GCT | ATG | GGA | AGT | GCT | GCA | GCT | TTA | AGG | 2214 |
| His | Ser | Lys | His | Lys | Met | Ile | Ala | Met | Gly | Ser | Ala | Ala | Ala | Leu | Arg | |
| | | | 715 | | | | | 720 | | | | | 725 | | | |
| AAT | CTC | ATG | GCA | AAT | AGG | CCT | GCG | AAG | TAC | AAG | GAT | GCC | AAT | ATT | ATG | 2262 |
| Asn | Leu | Met | Ala | Asn | Arg | Pro | Ala | Lys | Tyr | Lys | Asp | Ala | Asn | Ile | Met | |
| | | 730 | | | | | 735 | | | | | 740 | | | | |
| TCT | CCT | GGC | TCA | AGC | TTG | CCA | TCT | CTT | CAT | GTT | AGG | AAA | CAA | AAA | GCC | 2310 |
| Ser | Pro | Gly | Ser | Ser | Leu | Pro | Ser | Leu | His | Val | Arg | Lys | Gln | Lys | Ala | |
| | 745 | | | | | 750 | | | | | 755 | | | | | |
| CTA | GAA | GCA | GAA | TTA | GAT | GCT | CAG | CAC | TTA | TCA | GAA | ACT | TTT | GAC | AAT | 2358 |
| Leu | Glu | Ala | Glu | Leu | Asp | Ala | Gln | His | Leu | Ser | Glu | Thr | Phe | Asp | Asn | |
| 760 | | | | | 765 | | | | | 770 | | | | | 775 | |
| ATA | GAC | AAT | TTA | AGT | CCC | AAG | GCA | TCT | CAT | CGT | AGT | AAG | CAG | AGA | CAC | 2406 |
| Ile | Asp | Asn | Leu | Ser | Pro | Lys | Ala | Ser | His | Arg | Ser | Lys | Gln | Arg | His | |
| | | | | 780 | | | | | 785 | | | | | 790 | | |
| AAG | CAA | AGT | CTC | TAT | GGT | GAT | TAT | GTT | TTT | GAC | ACC | AAT | CGA | CAT | GAT | 2454 |
| Lys | Gln | Ser | Leu | Tyr | Gly | Asp | Tyr | Val | Phe | Asp | Thr | Asn | Arg | His | Asp | |
| | | | 795 | | | | | 800 | | | | | 805 | | | |
| GAT | AAT | AGG | TCA | GAC | AAT | TTT | AAT | ACT | GGC | AAC | ATG | ACT | GTC | CTT | TCA | 2502 |
| Asp | Asn | Arg | Ser | Asp | Asn | Phe | Asn | Thr | Gly | Asn | Met | Thr | Val | Leu | Ser | |
| | | 810 | | | | | 815 | | | | | 820 | | | | |
| CCA | TAT | TTG | AAT | ACT | ACA | GTG | TTA | CCC | AGC | TCC | TCT | TCA | TCA | AGA | GGA | 2550 |
| Pro | Tyr | Leu | Asn | Thr | Thr | Val | Leu | Pro | Ser | Ser | Ser | Ser | Ser | Arg | Gly | |
| | 825 | | | | | 830 | | | | | 835 | | | | | |
| AGC | TTA | GAT | AGT | TCT | CGT | TCT | GAA | AAA | GAT | AGA | AGT | TTG | GAG | AGA | GAA | 2598 |
| Ser | Leu | Asp | Ser | Ser | Arg | Ser | Glu | Lys | Asp | Arg | Ser | Leu | Glu | Arg | Glu | |
| 840 | | | | | 845 | | | | | 850 | | | | | 855 | |
| CGC | GGA | ATT | GGT | CTA | GGC | AAC | TAC | CAT | CCA | GCA | ACA | GAA | AAT | CCA | GGA | 2646 |
| Arg | Gly | Ile | Gly | Leu | Gly | Asn | Tyr | His | Pro | Ala | Thr | Glu | Asn | Pro | Gly | |
| | | | | 860 | | | | | 865 | | | | | 870 | | |
| ACT | TCT | TCA | AAG | CGA | GGT | TTG | CAG | ATC | TCC | ACC | ACT | GCA | GCC | CAG | ATT | 2694 |
| Thr | Ser | Ser | Lys | Arg | Gly | Leu | Gln | Ile | Ser | Thr | Thr | Ala | Ala | Gln | Ile | |
| | | | 875 | | | | | 880 | | | | | 885 | | | |
| GCC | AAA | GTC | ATG | GAA | GAA | GTG | TCA | GCC | ATT | CAT | ACC | TCT | CAG | GAA | GAC | 2742 |
| Ala | Lys | Val | Met | Glu | Glu | Val | Ser | Ala | Ile | His | Thr | Ser | Gln | Glu | Asp | |
| | | 890 | | | | | 895 | | | | | 900 | | | | |
| AGA | AGT | TCT | GGG | TCT | ACC | ACT | GAA | TTA | CAT | TGT | GTG | ACA | GAT | GAG | AGA | 2790 |
| Arg | Ser | Ser | Gly | Ser | Thr | Thr | Glu | Leu | His | Cys | Val | Thr | Asp | Glu | Arg | |
| | 905 | | | | | 910 | | | | | 915 | | | | | |
| AAT | GCA | CTT | AGA | AGA | AGC | TCT | GCT | GCC | CAT | ACA | CAT | TCA | AAC | ACT | TAC | 2838 |
| Asn | Ala | Leu | Arg | Arg | Ser | Ser | Ala | Ala | His | Thr | His | Ser | Asn | Thr | Tyr | |
| 920 | | | | | 925 | | | | | 930 | | | | | 935 | |
| AAT | TTC | ACT | AAG | TCG | GAA | AAT | TCA | AAT | AGG | ACA | TGT | TCT | ATG | CCT | TAT | 2886 |
| Asn | Phe | Thr | Lys | Ser | Glu | Asn | Ser | Asn | Arg | Thr | Cys | Ser | Met | Pro | Tyr | |
| | | | | 940 | | | | | 945 | | | | | 950 | | |
| GCC | AAA | TTA | GAA | TAC | AAG | AGA | TCT | TCA | AAT | GAT | AGT | TTA | AAT | AGT | GTC | 2934 |
| Ala | Lys | Leu | Glu | Tyr | Lys | Arg | Ser | Ser | Asn | Asp | Ser | Leu | Asn | Ser | Val | |
| | | | 955 | | | | | 960 | | | | | 965 | | | |
| AGT | AGT | AAT | GAT | GGT | TAT | GGT | AAA | AGA | GGT | CAA | ATG | AAA | CCC | TCG | ATT | 2982 |
| Ser | Ser | Asn | Asp | Gly | Tyr | Gly | Lys | Arg | Gly | Gln | Met | Lys | Pro | Ser | Ile | |
| | | 970 | | | | | 975 | | | | | 980 | | | | |
| GAA | TCC | TAT | TCT | GAA | GAT | GAT | GAA | AGT | AAG | TTT | TGC | AGT | TAT | GGT | CAA | 3030 |
| Glu | Ser | Tyr | Ser | Glu | Asp | Asp | Glu | Ser | Lys | Phe | Cys | Ser | Tyr | Gly | Gln | |
| | 985 | | | | | 990 | | | | | 995 | | | | | |
| TAC | CCA | GCC | GAC | CTA | GCC | CAT | AAA | ATA | CAT | AGT | GCA | AAT | CAT | ATG | GAT | 3078 |
| Tyr | Pro | Ala | Asp | Leu | Ala | His | Lys | Ile | His | Ser | Ala | Asn | His | Met | Asp | |
| 1000 | | | | | 1005 | | | | | 1010 | | | | | 1015 | |
| GAT | AAT | GAT | GGA | GAA | CTA | GAT | ACA | CCA | ATA | AAT | TAT | AGT | CTT | AAA | TAT | 3126 |
| Asp | Asn | Asp | Gly | Glu | Leu | Asp | Thr | Pro | Ile | Asn | Tyr | Ser | Leu | Lys | Tyr | |
| | | | | 1020 | | | | | 1025 | | | | | 1030 | | |
| TCA | GAT | GAG | CAG | TTG | AAC | TCT | GGA | AGG | CAA | AGT | CCT | TCA | CAG | AAT | GAA | 3174 |

|     |     |     |     |     |     |     |     |     |     |     |     |     |     |     |     |     |
|---|---|---|---|---|---|---|---|---|---|---|---|---|---|---|---|---|
| Ser | Asp | Glu | Gln | Leu | Asn | Ser | Gly | Arg | Gln | Ser | Pro | Ser | Gln | Asn | Glu | |
|     |     |     |     | 1035 |    |     |     |     | 1040 |    |     |     |     | 1045 |    | |

| AGA | TGG | GCA | AGA | CCC | AAA | CAC | ATA | ATA | GAA | GAT | GAA | ATA | AAA | CAA | AGT | 3222 |
|---|---|---|---|---|---|---|---|---|---|---|---|---|---|---|---|---|
| Arg | Trp | Ala | Arg | Pro | Lys | His | Ile | Ile | Glu | Asp | Glu | Ile | Lys | Gln | Ser | |
|     |     |     |     | 1050 |    |     |     | 1055 |   |     |     |     | 1060 |    |     | |

| GAG | CAA | AGA | CAA | TCA | AGG | AAT | CAA | AGT | ACA | ACT | TAT | CCT | GTT | TAT | ACT | 3270 |
|---|---|---|---|---|---|---|---|---|---|---|---|---|---|---|---|---|
| Glu | Gln | Arg | Gln | Ser | Arg | Asn | Gln | Ser | Thr | Thr | Tyr | Pro | Val | Tyr | Thr | |
|     |     |     |     | 1065 |    |     |     | 1070 |    |     |     |     | 1075 |    |     | |

| GAG | AGC | ACT | GAT | GAT | AAA | CAC | CTC | AAG | TTC | CAA | CCA | CAT | TTT | GGA | CAG | 3318 |
|---|---|---|---|---|---|---|---|---|---|---|---|---|---|---|---|---|
| Glu | Ser | Thr | Asp | Asp | Lys | His | Leu | Lys | Phe | Gln | Pro | His | Phe | Gly | Gln | |
| 1080 |   |     |     |     | 1085 |   |     |     |     | 1090 |   |     |     |     | 1095 | |

| CAG | GAA | TGT | GTT | TCT | CCA | TAC | AGG | TCA | CGG | GGA | GCC | AAT | GGT | TCA | GAA | 3366 |
|---|---|---|---|---|---|---|---|---|---|---|---|---|---|---|---|---|
| Gln | Glu | Cys | Val | Ser | Pro | Tyr | Arg | Ser | Arg | Gly | Ala | Asn | Gly | Ser | Glu | |
|     |     |     |     | 1100 |    |     |     | 1105 |   |     |     |     | 1110 |    |     | |

| ACA | AAT | CGA | GTG | GGT | TCT | AAT | CAT | GGA | ATT | AAT | CAA | AAT | GTA | AGC | CAG | 3414 |
|---|---|---|---|---|---|---|---|---|---|---|---|---|---|---|---|---|
| Thr | Asn | Arg | Val | Gly | Ser | Asn | His | Gly | Ile | Asn | Gln | Asn | Val | Ser | Gln | |
|     |     |     |     | 1115 |    |     |     | 1120 |    |     |     |     | 1125 |    |     | |

| TCT | TTG | TGT | CAA | GAA | GAT | GAC | TAT | GAA | GAT | GAT | AAG | CCT | ACC | AAT | TAT | 3462 |
|---|---|---|---|---|---|---|---|---|---|---|---|---|---|---|---|---|
| Ser | Leu | Cys | Gln | Glu | Asp | Asp | Tyr | Glu | Asp | Asp | Lys | Pro | Thr | Asn | Tyr | |
|     |     |     |     | 1130 |    |     |     | 1135 |   |     |     |     | 1140 |    |     | |

| AGT | GAA | CGT | TAC | TCT | GAA | GAA | GAA | CAG | CAT | GAA | GAA | GAA | GAG | AGA | CCA | 3510 |
|---|---|---|---|---|---|---|---|---|---|---|---|---|---|---|---|---|
| Ser | Glu | Arg | Tyr | Ser | Glu | Glu | Glu | Gln | His | Glu | Glu | Glu | Glu | Arg | Pro | |
|     |     |     |     | 1145 |    |     |     | 1150 |   |     |     |     | 1155 |    |     | |

| ACA | AAT | TAT | AGC | ATA | AAA | TAT | AAT | GAA | GAG | AAA | CGT | CAT | GTG | GAT | CAG | 3558 |
|---|---|---|---|---|---|---|---|---|---|---|---|---|---|---|---|---|
| Thr | Asn | Tyr | Ser | Ile | Lys | Tyr | Asn | Glu | Glu | Lys | Arg | His | Val | Asp | Gln | |
| 1160 |   |     |     |     | 1165 |   |     |     |     | 1170 |   |     |     |     | 1175 | |

| CCT | ATT | GAT | TAT | AGT | TTA | AAA | TAT | GCC | ACA | GAT | ATT | CCT | TCA | TCA | CAG | 3606 |
|---|---|---|---|---|---|---|---|---|---|---|---|---|---|---|---|---|
| Pro | Ile | Asp | Tyr | Ser | Leu | Lys | Tyr | Ala | Thr | Asp | Ile | Pro | Ser | Ser | Gln | |
|     |     |     |     | 1180 |    |     |     | 1185 |   |     |     |     | 1190 |    |     | |

| AAA | CAG | TCA | TTT | TCA | TTC | TCA | AAG | AGT | TCA | TCT | GGA | CAA | AGC | AGT | AAA | 3654 |
|---|---|---|---|---|---|---|---|---|---|---|---|---|---|---|---|---|
| Lys | Gln | Ser | Phe | Ser | Phe | Ser | Lys | Ser | Ser | Ser | Gly | Gln | Ser | Ser | Lys | |
|     |     |     |     | 1195 |    |     |     | 1200 |   |     |     |     | 1205 |    |     | |

| ACC | GAA | CAT | ATG | TCT | TCA | AGC | AGT | GAG | AAT | ACG | TCC | ACA | CCT | TCA | TCT | 3702 |
|---|---|---|---|---|---|---|---|---|---|---|---|---|---|---|---|---|
| Thr | Glu | His | Met | Ser | Ser | Ser | Ser | Glu | Asn | Thr | Ser | Thr | Pro | Ser | Ser | |
|     |     |     | 1210 |    |     |     |     | 1215 |   |     |     |     | 1220 |    |     | |

| AAT | GCC | AAG | AGG | CAG | AAT | CAG | CTC | CAT | CCA | AGT | TCT | GCA | CAG | AGT | AGA | 3750 |
|---|---|---|---|---|---|---|---|---|---|---|---|---|---|---|---|---|
| Asn | Ala | Lys | Arg | Gln | Asn | Gln | Leu | His | Pro | Ser | Ser | Ala | Gln | Ser | Arg | |
|     |     |     |     | 1225 |    |     |     | 1230 |   |     |     |     | 1235 |    |     | |

| AGT | GGT | CAG | CCT | CAA | AAG | GCT | GCC | ACT | TGC | AAA | GTT | TCT | TCT | ATT | AAC | 3798 |
|---|---|---|---|---|---|---|---|---|---|---|---|---|---|---|---|---|
| Ser | Gly | Gln | Pro | Gln | Lys | Ala | Ala | Thr | Cys | Lys | Val | Ser | Ser | Ile | Asn | |
| 1240 |   |     |     |     | 1245 |   |     |     |     | 1250 |   |     |     |     | 1255 | |

| CAA | GAA | ACA | ATA | CAG | ACT | TAT | TGT | GTA | GAA | GAT | ACT | CCA | ATA | TGT | TTT | 3846 |
|---|---|---|---|---|---|---|---|---|---|---|---|---|---|---|---|---|
| Gln | Glu | Thr | Ile | Gln | Thr | Tyr | Cys | Val | Glu | Asp | Thr | Pro | Ile | Cys | Phe | |
|     |     |     |     | 1260 |    |     |     | 1265 |   |     |     |     | 1270 |    |     | |

| TCA | AGA | TGT | AGT | TCA | TTA | TCA | TCT | TTG | TCA | TCA | GCT | GAA | GAT | GAA | ATA | 3894 |
|---|---|---|---|---|---|---|---|---|---|---|---|---|---|---|---|---|
| Ser | Arg | Cys | Ser | Ser | Leu | Ser | Ser | Leu | Ser | Ser | Ala | Glu | Asp | Glu | Ile | |
|     |     |     |     | 1275 |    |     |     | 1280 |   |     |     |     | 1285 |    |     | |

| GGA | TGT | AAT | CAG | ACG | ACA | CAG | GAA | GCA | GAT | TCT | GCT | AAT | ACC | CTG | CAA | 3942 |
|---|---|---|---|---|---|---|---|---|---|---|---|---|---|---|---|---|
| Gly | Cys | Asn | Gln | Thr | Thr | Gln | Glu | Ala | Asp | Ser | Ala | Asn | Thr | Leu | Gln | |
|     |     |     |     | 1290 |    |     |     | 1295 |   |     |     |     | 1300 |    |     | |

| ATA | GCA | GAA | ATA | AAA | GGA | AAG | ATT | GGA | ACT | AGG | TCA | GCT | GAA | GAT | CCT | 3990 |
|---|---|---|---|---|---|---|---|---|---|---|---|---|---|---|---|---|
| Ile | Ala | Glu | Ile | Lys | Gly | Lys | Ile | Gly | Thr | Arg | Ser | Ala | Glu | Asp | Pro | |
| 1305 |   |     |     |     | 1310 |   |     |     |     | 1315 |   |     |     |     |     | |

| GTG | AGC | GAA | GTT | CCA | GCA | GTG | TCA | CAG | CAC | CCT | AGA | ACC | AAA | TCC | AGC | 4038 |
|---|---|---|---|---|---|---|---|---|---|---|---|---|---|---|---|---|
| Val | Ser | Glu | Val | Pro | Ala | Val | Ser | Gln | His | Pro | Arg | Thr | Lys | Ser | Ser | |
| 1320 |   |     |     |     | 1325 |   |     |     |     | 1330 |   |     |     |     | 1335 | |

| AGA | CTG | CAG | GGT | TCT | AGT | TTA | TCT | TCA | GAA | TCA | GCC | AGG | CAC | AAA | GCT | 4086 |
|---|---|---|---|---|---|---|---|---|---|---|---|---|---|---|---|---|
| Arg | Leu | Gln | Gly | Ser | Ser | Leu | Ser | Ser | Glu | Ser | Ala | Arg | His | Lys | Ala | |
|     |     |     |     | 1340 |    |     |     | 1345 |   |     |     |     | 1350 |    |     | |

| GTT | GAA | TTT | CCT | TCA | GGA | GCG | AAA | TCT | CCC | TCC | AAA | AGT | GGT | GCT | CAG | 4134 |
|---|---|---|---|---|---|---|---|---|---|---|---|---|---|---|---|---|
| Val | Glu | Phe | Pro | Ser | Gly | Ala | Lys | Ser | Pro | Ser | Lys | Ser | Gly | Ala | Gln | |
|     |     |     |     | 1355 |    |     |     | 1360 |   |     |     |     | 1365 |    |     | |

| | | | | | | | | | | | | | | | | |
|---|---|---|---|---|---|---|---|---|---|---|---|---|---|---|---|---|
| ACA | CCC | AAA | AGT | CCA | CCT | GAA | CAC | TAT | GTT | CAG | GAG | ACC | CCA | CTC | ATG | 4182 |
| Thr | Pro | Lys | Ser | Pro | Pro | Glu | His | Tyr | Val | Gln | Glu | Thr | Pro | Leu | Met | |
| | | 1370 | | | | | 1375 | | | | | 1380 | | | | |
| TTT | AGC | AGA | TGT | ACT | TCT | GTC | AGT | TCA | CTT | GAT | AGT | TTT | GAG | AGT | CGT | 4230 |
| Phe | Ser | Arg | Cys | Thr | Ser | Val | Ser | Ser | Leu | Asp | Ser | Phe | Glu | Ser | Arg | |
| | 1385 | | | | | 1390 | | | | | 1395 | | | | | |
| TCG | ATT | GCC | AGC | TCC | GTT | CAG | AGT | GAA | CCA | TGC | AGT | GGA | ATG | GTA | AGT | 4278 |
| Ser | Ile | Ala | Ser | Ser | Val | Gln | Ser | Glu | Pro | Cys | Ser | Gly | Met | Val | Ser | |
| 1400 | | | | | 1405 | | | | | 1410 | | | | | 1415 | |
| GGC | ATT | ATA | AGC | CCC | AGT | GAT | CTT | CCA | GAT | AGC | CCT | GGA | CAA | ACC | ATG | 4326 |
| Gly | Ile | Ile | Ser | Pro | Ser | Asp | Leu | Pro | Asp | Ser | Pro | Gly | Gln | Thr | Met | |
| | | | 1420 | | | | | 1425 | | | | | 1430 | | | |
| CCA | CCA | AGC | AGA | AGT | AAA | ACA | CCT | CCA | CCA | CCT | CCT | CAA | ACA | GCT | CAA | 4374 |
| Pro | Pro | Ser | Arg | Ser | Lys | Thr | Pro | Pro | Pro | Pro | Pro | Gln | Thr | Ala | Gln | |
| | | | | 1435 | | | | | 1440 | | | | | 1445 | | |
| ACC | AAG | CGA | GAA | GTA | CCT | AAA | AAT | AAA | GCA | CCT | ACT | GCT | GAA | AAG | AGA | 4422 |
| Thr | Lys | Arg | Glu | Val | Pro | Lys | Asn | Lys | Ala | Pro | Thr | Ala | Glu | Lys | Arg | |
| | | 1450 | | | | | 1455 | | | | | 1460 | | | | |
| GAG | AGT | GGA | CCT | AAG | CAA | GCT | GCA | GTA | AAT | GCT | GCA | GTT | CAG | AGG | GTC | 4470 |
| Glu | Ser | Gly | Pro | Lys | Gln | Ala | Ala | Val | Asn | Ala | Ala | Val | Gln | Arg | Val | |
| | 1465 | | | | | 1470 | | | | | 1475 | | | | | |
| CAG | GTT | CTT | CCA | GAT | GCT | GAT | ACT | TTA | TTA | CAT | TTT | GCC | ACA | GAA | AGT | 4518 |
| Gln | Val | Leu | Pro | Asp | Ala | Asp | Thr | Leu | Leu | His | Phe | Ala | Thr | Glu | Ser | |
| 1480 | | | | | 1485 | | | | | 1490 | | | | | 1495 | |
| ACT | CCA | GAT | GGA | TTT | TCT | TGT | TCA | TCC | AGC | CTG | AGT | GCT | CTG | AGC | CTC | 4566 |
| Thr | Pro | Asp | Gly | Phe | Ser | Cys | Ser | Ser | Ser | Leu | Ser | Ala | Leu | Ser | Leu | |
| | | | | 1500 | | | | | 1505 | | | | | 1510 | | |
| GAT | GAG | CCA | TTT | ATA | CAG | AAA | GAT | GTG | GAA | TTA | AGA | ATA | ATG | CCT | CCA | 4614 |
| Asp | Glu | Pro | Phe | Ile | Gln | Lys | Asp | Val | Glu | Leu | Arg | Ile | Met | Pro | Pro | |
| | | | | 1515 | | | | | 1520 | | | | | 1525 | | |
| GTT | CAG | GAA | AAT | GAC | AAT | GGG | AAT | GAA | ACA | GAA | TCA | GAG | CAG | CCT | AAA | 4662 |
| Val | Gln | Glu | Asn | Asp | Asn | Gly | Asn | Glu | Thr | Glu | Ser | Glu | Gln | Pro | Lys | |
| | | 1530 | | | | | 1535 | | | | | 1540 | | | | |
| GAA | TCA | AAT | GAA | AAC | CAA | GAG | AAA | GAG | GCA | GAA | AAA | ACT | ATT | GAT | TCT | 4710 |
| Glu | Ser | Asn | Glu | Asn | Gln | Glu | Lys | Glu | Ala | Glu | Lys | Thr | Ile | Asp | Ser | |
| | | 1545 | | | | | 1550 | | | | | 1555 | | | | |
| GAA | AAG | GAC | CTA | TTA | GAT | GAT | TCA | GAT | GAT | GAT | GAT | ATT | GAA | ATA | CTA | 4758 |
| Glu | Lys | Asp | Leu | Leu | Asp | Asp | Ser | Asp | Asp | Asp | Asp | Ile | Glu | Ile | Leu | |
| 1560 | | | | | 1565 | | | | | 1570 | | | | | 1575 | |
| GAA | GAA | TGT | ATT | ATT | TCT | GCC | ATG | CCA | ACA | AAG | TCA | TCA | CGT | AAA | GGC | 4806 |
| Glu | Glu | Cys | Ile | Ile | Ser | Ala | Met | Pro | Thr | Lys | Ser | Ser | Arg | Lys | Gly | |
| | | | | 1580 | | | | | 1585 | | | | | 1590 | | |
| AAA | AAG | CCA | GCC | CAG | ACT | GCT | TCA | AAA | TTA | CCT | CCA | CCT | GTG | GCA | AGG | 4854 |
| Lys | Lys | Pro | Ala | Gln | Thr | Ala | Ser | Lys | Leu | Pro | Pro | Pro | Val | Ala | Arg | |
| | | | 1595 | | | | | 1600 | | | | | 1605 | | | |
| AAA | CCA | AGT | CAG | CTG | CCT | GTG | TAC | AAA | CTT | CTA | CCA | TCA | CAA | AAC | AGG | 4902 |
| Lys | Pro | Ser | Gln | Leu | Pro | Val | Tyr | Lys | Leu | Leu | Pro | Ser | Gln | Asn | Arg | |
| | | | 1610 | | | | | 1615 | | | | | 1620 | | | |
| TTG | CAA | CCC | CAA | AAG | CAT | GTT | AGT | TTT | ACA | CCG | GGG | GAT | GAT | ATG | CCA | 4950 |
| Leu | Gln | Pro | Gln | Lys | His | Val | Ser | Phe | Thr | Pro | Gly | Asp | Asp | Met | Pro | |
| | 1625 | | | | | 1630 | | | | | 1635 | | | | | |
| CGG | GTG | TAT | TGT | GTT | GAA | GGG | ACA | CCT | ATA | AAC | TTT | TCC | ACA | GCT | ACA | 4998 |
| Arg | Val | Tyr | Cys | Val | Glu | Gly | Thr | Pro | Ile | Asn | Phe | Ser | Thr | Ala | Thr | |
| 1640 | | | | | 1645 | | | | | 1650 | | | | | 1655 | |
| TCT | CTA | AGT | GAT | CTA | ACA | ATC | GAA | TCC | CCT | CCA | AAT | GAG | TTA | GCT | GCT | 5046 |
| Ser | Leu | Ser | Asp | Leu | Thr | Ile | Glu | Ser | Pro | Pro | Asn | Glu | Leu | Ala | Ala | |
| | | | | 1660 | | | | | 1665 | | | | | 1670 | | |
| GGA | GAA | GGA | GTT | AGA | GGA | GGA | GCA | CAG | TCA | GGT | GAA | TTT | GAA | AAA | CGA | 5094 |
| Gly | Glu | Gly | Val | Arg | Gly | Gly | Ala | Gln | Ser | Gly | Glu | Phe | Glu | Lys | Arg | |
| | | | | 1675 | | | | | 1680 | | | | | 1685 | | |
| GAT | ACC | ATT | CCT | ACA | GAA | GGC | AGA | AGT | ACA | GAT | GAG | GCT | CAA | GGA | GGA | 5142 |

-continued

| | | | | | | | | | | | | | | | | |
|---|---|---|---|---|---|---|---|---|---|---|---|---|---|---|---|---|
|Asp|Thr|Ile|Pro|Thr|Glu|Gly|Arg|Ser|Thr|Asp|Glu|Ala|Gln|Gly|Gly| |
| | |1690| | | |1695| | | |1700| | | | | | |

| AAA ACC TCA TCT GTA ACC ATA CCT GAA TTG GAT GAC AAT AAA GCA GAG | 5190 |
|---|---|
| Lys Thr Ser Ser Val Thr Ile Pro Glu Leu Asp Asp Asn Lys Ala Glu | |
| 1705 1710 1715 | |

| GAA GGT GAT ATT CTT GCA GAA TGC ATT AAT TCT GCT ATG CCC AAA GGG | 5238 |
|---|---|
| Glu Gly Asp Ile Leu Ala Glu Cys Ile Asn Ser Ala Met Pro Lys Gly | |
| 1720 1725 1730 1735 | |

| AAA AGT CAC AAG CCT TTC CGT GTG AAA AAG ATA ATG GAC CAG GTC CAG | 5286 |
|---|---|
| Lys Ser His Lys Pro Phe Arg Val Lys Lys Ile Met Asp Gln Val Gln | |
| 1740 1745 1750 | |

| CAA GCA TCT GCG TCG TCT TCT GCA CCC AAC AAA AAT CAG TTA GAT GGT | 5334 |
|---|---|
| Gln Ala Ser Ala Ser Ser Ser Ala Pro Asn Lys Asn Gln Leu Asp Gly | |
| 1755 1760 1765 | |

| AAG AAA AAG AAA CCA ACT TCA CCA GTA AAA CCT ATA CCA CAA AAT ACT | 5382 |
|---|---|
| Lys Lys Lys Lys Pro Thr Ser Pro Val Lys Pro Ile Pro Gln Asn Thr | |
| 1770 1775 1780 | |

| GAA TAT AGG ACA CGT GTA AGA AAA AAT GCA GAC TCA AAA AAT AAT TTA | 5430 |
|---|---|
| Glu Tyr Arg Thr Arg Val Arg Lys Asn Ala Asp Ser Lys Asn Asn Leu | |
| 1785 1790 1795 | |

| AAT GCT GAG AGA GTT TTC TCA GAC AAC AAA GAT TCA AAG AAA CAG AAT | 5478 |
|---|---|
| Asn Ala Glu Arg Val Phe Ser Asp Asn Lys Asp Ser Lys Lys Gln Asn | |
| 1800 1805 1810 1815 | |

| TTG AAA AAT AAT TCC AAG GAC TTC AAT GAT AAG CTC CCA AAT AAT GAA | 5526 |
|---|---|
| Leu Lys Asn Asn Ser Lys Asp Phe Asn Asp Lys Leu Pro Asn Asn Glu | |
| 1820 1825 1830 | |

| GAT AGA GTC AGA GGA AGT TTT GCT TTT GAT TCA CCT CAT CAT TAC ACG | 5574 |
|---|---|
| Asp Arg Val Arg Gly Ser Phe Ala Phe Asp Ser Pro His His Tyr Thr | |
| 1835 1840 1845 | |

| CCT ATT GAA GGA ACT CCT TAC TGT TTT TCA CGA AAT GAT TCT TTG AGT | 5622 |
|---|---|
| Pro Ile Glu Gly Thr Pro Tyr Cys Phe Ser Arg Asn Asp Ser Leu Ser | |
| 1850 1855 1860 | |

| TCT CTA GAT TTT GAT GAT GAT GAT GTT GAC CTT TCC AGG GAA AAG GCT | 5670 |
|---|---|
| Ser Leu Asp Phe Asp Asp Asp Asp Val Asp Leu Ser Arg Glu Lys Ala | |
| 1865 1870 1875 | |

| GAA TTA AGA AAG GCA AAA GAA AAT AAG GAA TCA GAG GCT AAA GTT ACC | 5718 |
|---|---|
| Glu Leu Arg Lys Ala Lys Glu Asn Lys Glu Ser Glu Ala Lys Val Thr | |
| 1880 1885 1890 1895 | |

| AGC CAC ACA GAA CTA ACC TCC AAC CAA CAA TCA GCT AAT AAG ACA CAA | 5766 |
|---|---|
| Ser His Thr Glu Leu Thr Ser Asn Gln Gln Ser Ala Asn Lys Thr Gln | |
| 1900 1905 1910 | |

| GCT ATT GCA AAG CAG CCA ATA AAT CGA GGT CAG CCT AAA CCC ATA CTT | 5814 |
|---|---|
| Ala Ile Ala Lys Gln Pro Ile Asn Arg Gly Gln Pro Lys Pro Ile Leu | |
| 1915 1920 1925 | |

| CAG AAA CAA TCC ACT TTT CCC CAG TCA TCC AAA GAC ATA CCA GAC AGA | 5862 |
|---|---|
| Gln Lys Gln Ser Thr Phe Pro Gln Ser Ser Lys Asp Ile Pro Asp Arg | |
| 1930 1935 1940 | |

| GGG GCA GCA ACT GAT GAA AAG TTA CAG AAT TTT GCT ATT GAA AAT ACT | 5910 |
|---|---|
| Gly Ala Ala Thr Asp Glu Lys Leu Gln Asn Phe Ala Ile Glu Asn Thr | |
| 1945 1950 1955 | |

| CCA GTT TGC TTT TCT CAT AAT TCC TCT CTG AGT TCT CTC AGT GAC ATT | 5958 |
|---|---|
| Pro Val Cys Phe Ser His Asn Ser Ser Leu Ser Ser Leu Ser Asp Ile | |
| 1960 1965 1970 1975 | |

| GAC CAA GAA AAC AAC AAT AAA GAA AAT GAA CCT ATC AAA GAG ACT GAG | 6006 |
|---|---|
| Asp Gln Glu Asn Asn Asn Lys Glu Asn Glu Pro Ile Lys Glu Thr Glu | |
| 1980 1985 1990 | |

| CCC CCT GAC TCA CAG GGA GAA CCA AGT AAA CCT CAA GCA TCA GGC TAT | 6054 |
|---|---|
| Pro Pro Asp Ser Gln Gly Glu Pro Ser Lys Pro Gln Ala Ser Gly Tyr | |
| 1995 2000 2005 | |

| GCT CCT AAA TCA TTT CAT GTT GAA GAT ACC CCA GTT TGT TTC TCA AGA | 6102 |
|---|---|
| Ala Pro Lys Ser Phe His Val Glu Asp Thr Pro Val Cys Phe Ser Arg | |
| 2010 2015 2020 | |

| | | | | | | | | | | | | | | | | |
|---|---|---|---|---|---|---|---|---|---|---|---|---|---|---|---|---|
| AAC | AGT | TCT | CTC | AGT | TCT | CTT | AGT | ATT | GAC | TCT | GAA | GAT | GAC | CTG | TTG | 6150 |
| Asn | Ser | Ser | Leu | Ser | Ser | Leu | Ser | Ile | Asp | Ser | Glu | Asp | Asp | Leu | Leu | |
| | | 2025 | | | | 2030 | | | | 2035 | | | | | | |
| CAG | GAA | TGT | ATA | AGC | TCC | GCA | ATG | CCA | AAA | AAG | AAA | AAG | CCT | TCA | AGA | 6198 |
| Gln | Glu | Cys | Ile | Ser | Ser | Ala | Met | Pro | Lys | Lys | Lys | Lys | Pro | Ser | Arg | |
| 2040 | | | | 2045 | | | | 2050 | | | | | | | 2055 | |
| CTC | AAG | GGT | GAT | AAT | GAA | AAA | CAT | AGT | CCC | AGA | AAT | ATG | GGT | GGC | ATA | 6246 |
| Leu | Lys | Gly | Asp | Asn | Glu | Lys | His | Ser | Pro | Arg | Asn | Met | Gly | Gly | Ile | |
| | | | | 2060 | | | | | 2065 | | | | | 2070 | | |
| TTA | GGT | GAA | GAT | CTG | ACA | CTT | GAT | TTG | AAA | GAT | ATA | CAG | AGA | CCA | GAT | 6294 |
| Leu | Gly | Glu | Asp | Leu | Thr | Leu | Asp | Leu | Lys | Asp | Ile | Gln | Arg | Pro | Asp | |
| | | | | 2075 | | | | 2080 | | | | 2085 | | | | |
| TCA | GAA | CAT | GGT | CTA | TCC | CCT | GAT | TCA | GAA | AAT | TTT | GAT | TGG | AAA | GCT | 6342 |
| Ser | Glu | His | Gly | Leu | Ser | Pro | Asp | Ser | Glu | Asn | Phe | Asp | Trp | Lys | Ala | |
| | | 2090 | | | | 2095 | | | | 2100 | | | | | | |
| ATT | CAG | GAA | GGT | GCA | AAT | TCC | ATA | GTA | AGT | AGT | TTA | CAT | CAA | GCT | GCT | 6390 |
| Ile | Gln | Glu | Gly | Ala | Asn | Ser | Ile | Val | Ser | Ser | Leu | His | Gln | Ala | Ala | |
| | 2105 | | | | 2110 | | | | | 2115 | | | | | | |
| GCT | GCT | GCA | TGT | TTA | TCT | AGA | CAA | GCT | TCG | TCT | GAT | TCA | GAT | TCC | ATC | 6438 |
| Ala | Ala | Ala | Cys | Leu | Ser | Arg | Gln | Ala | Ser | Ser | Asp | Ser | Asp | Ser | Ile | |
| 2120 | | | | | 2125 | | | | | 2130 | | | | | 2135 | |
| CTT | TCC | CTG | AAA | TCA | GGA | ATC | TCT | CTG | GGA | TCA | CCA | TTT | CAT | CTT | ACA | 6486 |
| Leu | Ser | Leu | Lys | Ser | Gly | Ile | Ser | Leu | Gly | Ser | Pro | Phe | His | Leu | Thr | |
| | | | | 2140 | | | | | 2145 | | | | | 2150 | | |
| CCT | GAT | CAA | GAA | GAA | AAA | CCC | TTT | ACA | AGT | AAT | AAA | GGC | CCA | CGA | ATT | 6534 |
| Pro | Asp | Gln | Glu | Glu | Lys | Pro | Phe | Thr | Ser | Asn | Lys | Gly | Pro | Arg | Ile | |
| | | | 2155 | | | | | 2160 | | | | | 2165 | | | |
| CTA | AAA | CCA | GGG | GAG | AAA | AGT | ACA | TTG | GAA | ACT | AAA | AAG | ATA | GAA | TCT | 6582 |
| Leu | Lys | Pro | Gly | Glu | Lys | Ser | Thr | Leu | Glu | Thr | Lys | Lys | Ile | Glu | Ser | |
| | | 2170 | | | | | 2175 | | | | | 2180 | | | | |
| GAA | AGT | AAA | GGA | ATC | AAA | GGA | GGA | AAA | AAA | GTT | TAT | AAA | AGT | TTG | ATT | 6630 |
| Glu | Ser | Lys | Gly | Ile | Lys | Gly | Gly | Lys | Lys | Val | Tyr | Lys | Ser | Leu | Ile | |
| 2185 | | | | | 2190 | | | | | | 2195 | | | | | |
| ACT | GGA | AAA | GTT | CGA | TCT | AAT | TCA | GAA | ATT | TCA | GGC | CAA | ATG | AAA | CAG | 6678 |
| Thr | Gly | Lys | Val | Arg | Ser | Asn | Ser | Glu | Ile | Ser | Gly | Gln | Met | Lys | Gln | |
| 2200 | | | | | 2205 | | | | | 2210 | | | | | 2215 | |
| CCC | CTT | CAA | GCA | AAC | ATG | CCT | TCA | ATC | TCT | CGA | GGC | AGG | ACA | ATG | ATT | 6726 |
| Pro | Leu | Gln | Ala | Asn | Met | Pro | Ser | Ile | Ser | Arg | Gly | Arg | Thr | Met | Ile | |
| | | | 2220 | | | | | 2225 | | | | | 2230 | | | |
| CAT | ATT | CCA | GGA | GTT | CGA | AAT | AGC | TCC | TCA | AGT | ACA | AGT | CCT | GTT | TCT | 6774 |
| His | Ile | Pro | Gly | Val | Arg | Asn | Ser | Ser | Ser | Thr | Ser | Pro | Val | Ser | | |
| | | | 2235 | | | | | 2240 | | | | | 2245 | | | |
| AAA | AAA | GGC | CCA | CCC | CTT | AAG | ACT | CCA | GCC | TCC | AAA | AGC | CCT | AGT | GAA | 6822 |
| Lys | Lys | Gly | Pro | Pro | Leu | Lys | Thr | Pro | Ala | Ser | Lys | Ser | Pro | Ser | Glu | |
| | | | 2250 | | | | 2255 | | | | | 2260 | | | | |
| GGT | CAA | ACA | GCC | ACC | ACT | TCT | CCT | AGA | GGA | GCC | AAG | CCA | TCT | GTG | AAA | 6870 |
| Gly | Gln | Thr | Ala | Thr | Thr | Ser | Pro | Arg | Gly | Ala | Lys | Pro | Ser | Val | Lys | |
| | 2265 | | | | | 2270 | | | | | | 2275 | | | | |
| TCA | GAA | TTA | AGC | CCT | GTT | GCC | AGG | CAG | ACA | TCC | CAA | ATA | GGT | GGG | TCA | 6918 |
| Ser | Glu | Leu | Ser | Pro | Val | Ala | Arg | Gln | Thr | Ser | Gln | Ile | Gly | Gly | Ser | |
| 2280 | | | | | 2285 | | | | | 2290 | | | | | 2295 | |
| AGT | AAA | GCA | CCT | TCT | AGA | TCA | GGA | TCT | AGA | GAT | TCG | ACC | CCT | TCA | AGA | 6966 |
| Ser | Lys | Ala | Pro | Ser | Arg | Ser | Gly | Ser | Arg | Asp | Ser | Thr | Pro | Ser | Arg | |
| | | | | 2300 | | | | | 2305 | | | | | 2310 | | |
| CCT | GCC | CAG | CAA | CCA | TTA | AGT | AGA | CCT | ATA | CAG | TCT | CCT | GGC | CGA | AAC | 7014 |
| Pro | Ala | Gln | Gln | Pro | Leu | Ser | Arg | Pro | Ile | Gln | Ser | Pro | Gly | Arg | Asn | |
| | | | | 2315 | | | | | 2320 | | | | | 2325 | | |
| TCA | ATT | TCC | CCT | GGT | AGA | AAT | GGA | ATA | AGT | CCT | CCT | AAC | AAA | TTA | TCT | 7062 |
| Ser | Ile | Ser | Pro | Gly | Arg | Asn | Gly | Ile | Ser | Pro | Pro | Asn | Lys | Leu | Ser | |
| | | | | 2330 | | | | | 2335 | | | | | 2340 | | |
| CAA | CTT | CCA | AGG | ACA | TCA | TCC | CCT | AGT | ACT | GCT | TCA | ACT | AAG | TCC | TCA | 7110 |

```
Gln Leu Pro Arg Thr Ser Ser Pro Ser Thr Ala Ser Thr Lys Ser Ser
    2345                2350                2355

GGT TCT GGA AAA ATG TCA TAT ACA TCT CCA GGT AGA CAG ATG AGC CAA      7158
Gly Ser Gly Lys Met Ser Tyr Thr Ser Pro Gly Arg Gln Met Ser Gln
2360                2365                2370                2375

CAG AAC CTT ACC AAA CAA ACA GGT TTA TCC AAG AAT GCC AGT AGT ATT      7206
Gln Asn Leu Thr Lys Gln Thr Gly Leu Ser Lys Asn Ala Ser Ser Ile
            2380                2385                2390

CCA AGA AGT GAG TCT GCC TCC AAA GGA CTA AAT CAG ATG AAT AAT GGT      7254
Pro Arg Ser Glu Ser Ala Ser Lys Gly Leu Asn Gln Met Asn Asn Gly
                2395                2400                2405

AAT GGA GCC AAT AAA AAG GTA GAA CTT TCT AGA ATG TCT TCA ACT AAA      7302
Asn Gly Ala Asn Lys Lys Val Glu Leu Ser Arg Met Ser Ser Thr Lys
                    2410                2415                2420

TCA AGT GGA AGT GAA TCT GAT AGA TCA GAA AGA CCT GTA TTA GTA CGC      7350
Ser Ser Gly Ser Glu Ser Asp Arg Ser Glu Arg Pro Val Leu Val Arg
                2425                2430                2435

CAG TCA ACT TTC ATC AAA GAA GCT CCA AGC CCA ACC TTA AGA AGA AAA      7398
Gln Ser Thr Phe Ile Lys Glu Ala Pro Ser Pro Thr Leu Arg Arg Lys
2440                2445                2450                2455

TTG GAG GAA TCT GCT TCA TTT GAA TCT CTT TCT CCA TCA TCT AGA CCA      7446
Leu Glu Glu Ser Ala Ser Phe Glu Ser Leu Ser Pro Ser Ser Arg Pro
                    2460                2465                2470

GCT TCT CCC ACT AGG TCC CAG GCA CAA ACT CCA GTT TTA AGT CCT TCC      7494
Ala Ser Pro Thr Arg Ser Gln Ala Gln Thr Pro Val Leu Ser Pro Ser
                2475                2480                2485

CTT CCT GAT ATG TCT CTA TCC ACA CAT TCG TCT GTT CAG GCT GGT GGA      7542
Leu Pro Asp Met Ser Leu Ser Thr His Ser Ser Val Gln Ala Gly Gly
                2490                2495                2500

TGG CGA AAA CTC CCA CCT AAT CTC AGT CCC ACT ATA GAG TAT AAT GAT      7590
Trp Arg Lys Leu Pro Pro Asn Leu Ser Pro Thr Ile Glu Tyr Asn Asp
    2505                2510                2515

GGA AGA CCA GCA AAG CGC CAT GAT ATT GCA CGG TCT CAT TCT GAA AGT      7638
Gly Arg Pro Ala Lys Arg His Asp Ile Ala Arg Ser His Ser Glu Ser
2520                2525                2530                2535

CCT TCT AGA CTT CCA ATC AAT AGG TCA GGA ACC TGG AAA CGT GAG CAC      7686
Pro Ser Arg Leu Pro Ile Asn Arg Ser Gly Thr Trp Lys Arg Glu His
                2540                2545                2550

AGC AAA CAT TCA TCA TCC CTT CCT CGA GTA AGC ACT TGG AGA AGA ACT      7734
Ser Lys His Ser Ser Ser Leu Pro Arg Val Ser Thr Trp Arg Arg Thr
            2555                2560                2565

GGA AGT TCA TCT TCA ATT CTT TCT GCT TCA TCA GAA TCC AGT GAA AAA      7782
Gly Ser Ser Ser Ser Ile Leu Ser Ala Ser Ser Glu Ser Ser Glu Lys
        2570                2575                2580

GCA AAA AGT GAG GAT GAA AAA CAT GTG AAC TCT ATT TCA GGA ACC AAA      7830
Ala Lys Ser Glu Asp Glu Lys His Val Asn Ser Ile Ser Gly Thr Lys
2585                2590                2595

CAA AGT AAA GAA AAC CAA GTA TCC GCA AAA GGA ACA TGG AGA AAA ATA      7878
Gln Ser Lys Glu Asn Gln Val Ser Ala Lys Gly Thr Trp Arg Lys Ile
2600                2605                2610                2615

AAA GAA AAT GAA TTT TCT CCC ACA AAT AGT ACT TCT CAG ACC GTT TCC      7926
Lys Glu Asn Glu Phe Ser Pro Thr Asn Ser Thr Ser Gln Thr Val Ser
                2620                2625                2630

TCA GGT GCT ACA AAT GGT GCT GAA TCA AAG ACT CTA ATT TAT CAA ATG      7974
Ser Gly Ala Thr Asn Gly Ala Glu Ser Lys Thr Leu Ile Tyr Gln Met
            2635                2640                2645

GCA CCT GCT GTT TCT AAA ACA GAG GAT GTT TGG GTG AGA ATT GAG GAC      8022
Ala Pro Ala Val Ser Lys Thr Glu Asp Val Trp Val Arg Ile Glu Asp
                2650                2655                2660

TGT CCC ATT AAC AAT CCT AGA TCT GGA AGA TCT CCC ACA GGT AAT ACT      8070
Cys Pro Ile Asn Asn Pro Arg Ser Gly Arg Ser Pro Thr Gly Asn Thr
    2665                2670                2675
```

```
CCC CCG GTG ATT GAC AGT GTT TCA GAA AAG GCA AAT CCA AAC ATT AAA        8118
Pro Pro Val Ile Asp Ser Val Ser Glu Lys Ala Asn Pro Asn Ile Lys
2680            2685                2690                2695

GAT TCA AAA GAT AAT CAG GCA AAA CAA AAT GTG GGT AAT GGC AGT GTT        8166
Asp Ser Lys Asp Asn Gln Ala Lys Gln Asn Val Gly Asn Gly Ser Val
                2700                2705                2710

CCC ATG CGT ACC GTG GGT TTG GAA AAT CGC CTG ACC TCC TTT ATT CAG        8214
Pro Met Arg Thr Val Gly Leu Glu Asn Arg Leu Thr Ser Phe Ile Gln
            2715                2720                2725

GTG GAT GCC CCT GAC CAA AAA GGA ACT GAG ATA AAA CCA GGA CAA AAT        8262
Val Asp Ala Pro Asp Gln Lys Gly Thr Glu Ile Lys Pro Gly Gln Asn
        2730                2735                2740

AAT CCT GTC CCT GTA TCA GAG ACT AAT GAA AGT CCT ATA GTG GAA CGT        8310
Asn Pro Val Pro Val Ser Glu Thr Asn Glu Ser Pro Ile Val Glu Arg
2745                2750                2755

ACC CCA TTC AGT TCT AGC AGC TCA AGC AAA CAC AGT TCA CCT AGT GGG        8358
Thr Pro Phe Ser Ser Ser Ser Ser Ser Lys His Ser Ser Pro Ser Gly
2760            2765                2770                2775

ACT GTT GCT GCC AGA GTG ACT CCT TTT AAT TAC AAC CCA AGC CCT AGG        8406
Thr Val Ala Ala Arg Val Thr Pro Phe Asn Tyr Asn Pro Ser Pro Arg
                2780                2785                2790

AAA AGC AGC GCA GAT AGC ACT TCA GCT CGG CCA TCT CAG ATC CCA ACT        8454
Lys Ser Ser Ala Asp Ser Thr Ser Ala Arg Pro Ser Gln Ile Pro Thr
            2795                2800                2805

CCA GTG AAT AAC AAC ACA AAG AAG CGA GAT TCC AAA ACT GAC AGC ACA        8502
Pro Val Asn Asn Asn Thr Lys Lys Arg Asp Ser Lys Thr Asp Ser Thr
        2810                2815                2820

GAA TCC AGT GGA ACC CAA AGT CCT AAG CGC CAT TCT GGG TCT TAC CTT        8550
Glu Ser Ser Gly Thr Gln Ser Pro Lys Arg His Ser Gly Ser Tyr Leu
2825                2830                2835

GTG ACA TCT GTT TAAAAGAGAG GAAGAATGAA ACTAAGAAAA TTCTATGTTA            8602
Val Thr Ser Val
2840

ATTACAACTG CTATATAGAC ATTTTGTTTC AAATGAAACT TTAAAAGACT GAAAAATTTT      8662

GTAAATAGGT TTGATTCTTG TTAGAGGGTT TTTGTTCTGG AAGCCATATT TGATAGTATA      8722

CTTTGTCTTC ACTGGTCTTA TTTTGGGAGG CACTCTTGAT GGTTAGGAAA AAATAGAAAG      8782

CCAAGTATGT TTGTACAGTA TGTTTACAT GTATTTAAAG TAGCATCCCA TCCCAACTTC       8842

CTTAATTATT GCTTGTCTAA AATAATGAAC ACTACAGATA GGAAATATGA TATATTGCTG      8902

TTATCAATCA TTTCTAGATT ATAAACTGAC TAAACTTACA TCAGGGGAAA ATTGGTATTT      8962

ATGCAAAAAA AAAATGTTTT TGTCCTTGTG AGTCCATCTA ACATCATAAT TAATCATGTG      9022

GCTGTGAAAT TCACAGTAAT ATGGTTCCCG ATGAACAAGT TTACCCAGCC TGCTTTGCTT      9082

ACTGCATGAA TGAAACTGAT GGTTCAATTT CAGAAGTAAT GATTAACAGT TATGTGGTCA      9142

CATGATGTGC ATAGAGATAG CTACAGTGTA ATAATTTACA CTATTTGTG CTCCAAACAA       9202

AACAAAAATC TGTGTAACTG TAAAACATTG AATGAAACTA TTTTACCTGA ACTAGATTTT     9262

ATCTGAAAGT AGGTAGAATT TTTGCTATGC TGTAATTTGT TGTATATTCT GGTATTTGAG     9322

GTGAGATGGC TGCTCTTTAT TAATGAGACA TGAATTGTGT CTCAACAGAA ACTAAATGAA     9382

CATTTCAGAA TAAATTATTG CTGTATGTAA ACTGTTACTG AAATTGGTAT TTGTTTGAAG     9442

GGTTTGTTTC ACATTTGTAT TAATTAATTG TTTAAATGC CTCTTTTAAA AGCTTATATA      9502

AATTTTTTCT TCAGCTTCTA TGCATTAAGA GTAAAATTCC TCTTACTGTA ATAAAAACAT     9562

TGAAGAAGAC TGTTGCCACT TAACCATTCC ATGCGTTGGC ACTT                      9606
```

( 2 ) INFORMATION FOR SEQ ID NO:2:

5,352,775

-continued ( i ) SEQUENCE CHARACTERISTICS:
  ( A ) LENGTH: 2843 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Ala Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
             20                  25                  30

His Leu Thr Lys Leu Glu Thr Glu Ala Ser Asn Met Lys Glu Val Leu
         35                  40                  45

Lys Gln Leu Gln Gly Ser Ile Glu Asp Glu Ala Met Ala Ser Ser Gly
 50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
             85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Leu Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
```

|     |     |     |     |     |     |     |     |     |     |     |     |     |     |     |     |
|---|---|---|---|---|---|---|---|---|---|---|---|---|---|---|---|
| 385 | | | | 390 | | | | 395 | | | | 400 | | | |
| Arg | Arg | Glu | Ile | Arg | Val | Leu | His | Leu | Leu | Glu | Gln | Ile | Arg | Ala | Tyr |
| | | | | 405 | | | | 410 | | | | 415 | | | |
| Cys | Glu | Thr | Cys | Trp | Glu | Trp | Gln | Glu | Ala | His | Glu | Pro | Gly | Met | Asp |
| | | | 420 | | | | 425 | | | | | 430 | | | |
| Gln | Asp | Lys | Asn | Pro | Met | Pro | Ala | Pro | Val | Glu | His | Gln | Ile | Cys | Pro |
| | | | 435 | | | | 440 | | | | | 445 | | | |
| Ala | Val | Cys | Val | Leu | Met | Lys | Leu | Ser | Phe | Asp | Glu | His | Arg | His | |
| 450 | | | | | 455 | | | | | 460 | | | | | |
| Ala | Met | Asn | Glu | Leu | Gly | Gly | Leu | Gln | Ala | Ile | Ala | Glu | Leu | Leu | Gln |
| 465 | | | | 470 | | | | 475 | | | | | | | 480 |
| Val | Asp | Cys | Glu | Met | Tyr | Gly | Leu | Thr | Asn | Asp | His | Tyr | Ser | Ile | Thr |
| | | | | 485 | | | | | 490 | | | | | 495 | |
| Leu | Arg | Arg | Tyr | Ala | Gly | Met | Ala | Leu | Thr | Asn | Leu | Thr | Phe | Gly | Asp |
| | | | 500 | | | | | 505 | | | | | 510 | | |
| Val | Ala | Asn | Lys | Ala | Thr | Leu | Cys | Ser | Met | Lys | Gly | Cys | Met | Arg | Ala |
| | | | 515 | | | | 520 | | | | | 525 | | | |
| Leu | Val | Ala | Gln | Leu | Lys | Ser | Glu | Ser | Glu | Asp | Leu | Gln | Gln | Val | Ile |
| | 530 | | | | | 535 | | | | | 540 | | | | |
| Ala | Ser | Val | Leu | Arg | Asn | Leu | Ser | Trp | Arg | Ala | Asp | Val | Asn | Ser | Lys |
| 545 | | | | | 550 | | | | | 555 | | | | | 560 |
| Lys | Thr | Leu | Arg | Glu | Val | Gly | Ser | Val | Lys | Ala | Leu | Met | Glu | Cys | Ala |
| | | | | 565 | | | | | 570 | | | | | 575 | |
| Leu | Glu | Val | Lys | Lys | Glu | Ser | Thr | Leu | Lys | Ser | Val | Leu | Ser | Ala | Leu |
| | | | 580 | | | | | 585 | | | | | 590 | | |
| Trp | Asn | Leu | Ser | Ala | His | Cys | Thr | Glu | Asn | Lys | Ala | Asp | Ile | Cys | Ala |
| | | 595 | | | | | 600 | | | | | 605 | | | |
| Val | Asp | Gly | Ala | Leu | Ala | Phe | Leu | Val | Gly | Thr | Leu | Thr | Tyr | Arg | Ser |
| | 610 | | | | | 615 | | | | | 620 | | | | |
| Gln | Thr | Asn | Thr | Leu | Ala | Ile | Ile | Glu | Ser | Gly | Gly | Ile | Leu | Arg | |
| 625 | | | | | 630 | | | | | 635 | | | | | 640 |
| Asn | Val | Ser | Ser | Leu | Ile | Ala | Thr | Asn | Glu | Asp | His | Arg | Gln | Ile | Leu |
| | | | | 645 | | | | | 650 | | | | | 655 | |
| Arg | Glu | Asn | Asn | Cys | Leu | Gln | Thr | Leu | Leu | Gln | His | Leu | Lys | Ser | His |
| | | | 660 | | | | | 665 | | | | | 670 | | |
| Ser | Leu | Thr | Ile | Val | Ser | Asn | Ala | Cys | Gly | Thr | Leu | Trp | Asn | Leu | Ser |
| | | 675 | | | | | 680 | | | | | 685 | | | |
| Ala | Arg | Asn | Pro | Lys | Asp | Gln | Glu | Ala | Leu | Trp | Asp | Met | Gly | Ala | Val |
| | 690 | | | | | 695 | | | | | 700 | | | | |
| Ser | Met | Leu | Lys | Asn | Leu | Ile | His | Ser | Lys | His | Lys | Met | Ile | Ala | Met |
| 705 | | | | | 710 | | | | | 715 | | | | | 720 |
| Gly | Ser | Ala | Ala | Ala | Leu | Arg | Asn | Leu | Met | Ala | Asn | Arg | Pro | Ala | Lys |
| | | | | 725 | | | | | 730 | | | | | 735 | |
| Tyr | Lys | Asp | Ala | Asn | Ile | Met | Ser | Pro | Gly | Ser | Ser | Leu | Pro | Ser | Leu |
| | | | 740 | | | | | 745 | | | | | 750 | | |
| His | Val | Arg | Lys | Gln | Lys | Ala | Leu | Glu | Ala | Glu | Leu | Asp | Ala | Gln | His |
| | | | 755 | | | | | 760 | | | | | 765 | | |
| Leu | Ser | Glu | Thr | Phe | Asp | Asn | Ile | Asp | Asn | Leu | Ser | Pro | Lys | Ala | Ser |
| | 770 | | | | | 775 | | | | | 780 | | | | |
| His | Arg | Ser | Lys | Gln | Arg | His | Lys | Gln | Ser | Leu | Tyr | Gly | Asp | Tyr | Val |
| 785 | | | | | 790 | | | | | 795 | | | | | 800 |
| Phe | Asp | Thr | Asn | Arg | His | Asp | Asp | Asn | Arg | Ser | Asp | Asn | Phe | Asn | Thr |
| | | | | 805 | | | | | 810 | | | | | 815 | |
| Gly | Asn | Met | Thr | Val | Leu | Ser | Pro | Tyr | Leu | Asn | Thr | Thr | Val | Leu | Pro |
| | | | 820 | | | | | 825 | | | | | 830 | | |

| | | | | | | | | | | | | | |
|---|---|---|---|---|---|---|---|---|---|---|---|---|---|
|Ser|Ser|Ser|Ser|Ser|Arg|Gly|Ser|Leu|Asp|Ser|Ser|Arg|Ser|Glu|Lys|
| | |835| | | |840| | | |845| | | |

Asp Arg Ser Leu Glu Arg Glu Arg Gly Ile Gly Leu Gly Asn Tyr His
850                855                860

Pro Ala Thr Glu Asn Pro Gly Thr Ser Ser Lys Arg Gly Leu Gln Ile
865                870                875                880

Ser Thr Thr Ala Ala Gln Ile Ala Lys Val Met Glu Glu Val Ser Ala
                885                890                895

Ile His Thr Ser Gln Glu Asp Arg Ser Ser Gly Ser Thr Thr Glu Leu
            900                905                910

His Cys Val Thr Asp Glu Arg Asn Ala Leu Arg Arg Ser Ser Ala Ala
            915                920                925

His Thr His Ser Asn Thr Tyr Asn Phe Thr Lys Ser Glu Asn Ser Asn
930                935                940

Arg Thr Cys Ser Met Pro Tyr Ala Lys Leu Glu Tyr Lys Arg Ser Ser
945                950                955                960

Asn Asp Ser Leu Asn Ser Val Ser Ser Asn Asp Gly Tyr Gly Lys Arg
                965                970                975

Gly Gln Met Lys Pro Ser Ile Glu Ser Tyr Ser Glu Asp Asp Glu Ser
            980                985                990

Lys Phe Cys Ser Tyr Gly Gln Tyr Pro Ala Asp Leu Ala His Lys Ile
        995                1000               1005

His Ser Ala Asn His Met Asp Asp Asn Asp Gly Glu Leu Asp Thr Pro
    1010               1015               1020

Ile Asn Tyr Ser Leu Lys Tyr Ser Asp Glu Gln Leu Asn Ser Gly Arg
1025               1030               1035               1040

Gln Ser Pro Ser Gln Asn Glu Arg Trp Ala Arg Pro Lys His Ile Ile
            1045               1050               1055

Glu Asp Glu Ile Lys Gln Ser Glu Gln Arg Gln Ser Arg Asn Gln Ser
        1060               1065               1070

Thr Thr Tyr Pro Val Tyr Thr Glu Ser Thr Asp Asp Lys His Leu Lys
    1075               1080               1085

Phe Gln Pro His Phe Gly Gln Gln Glu Cys Val Ser Pro Tyr Arg Ser
    1090               1095               1100

Arg Gly Ala Asn Gly Ser Glu Thr Asn Arg Val Gly Ser Asn His Gly
1105               1110               1115               1120

Ile Asn Gln Asn Val Ser Gln Ser Leu Cys Gln Glu Asp Asp Tyr Glu
            1125               1130               1135

Asp Asp Lys Pro Thr Asn Tyr Ser Glu Arg Tyr Ser Glu Glu Glu Gln
        1140               1145               1150

His Glu Glu Glu Glu Arg Pro Thr Asn Tyr Ser Ile Lys Tyr Asn Glu
    1155               1160               1165

Glu Lys Arg His Val Asp Gln Pro Ile Asp Tyr Ser Leu Lys Tyr Ala
    1170               1175               1180

Thr Asp Ile Pro Ser Ser Gln Lys Gln Ser Phe Ser Phe Ser Lys Ser
1185               1190               1195               1200

Ser Ser Gly Gln Ser Ser Lys Thr Glu His Met Ser Ser Ser Ser Glu
            1205               1210               1215

Asn Thr Ser Thr Pro Ser Ser Asn Ala Lys Arg Gln Asn Gln Leu His
            1220               1225               1230

Pro Ser Ser Ala Gln Ser Arg Ser Gly Gln Pro Gln Lys Ala Ala Thr
    1235               1240               1245

Cys Lys Val Ser Ser Ile Asn Gln Glu Thr Ile Gln Thr Tyr Cys Val
1250               1255               1260

```
Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
            1285                1290                1295

Asp Ser Ala Asn Thr Leu Gln Ile Ala Glu Ile Lys Gly Lys Ile Gly
            1300                1305                1310

Thr Arg Ser Ala Glu Asp Pro Val Ser Glu Val Pro Ala Val Ser Gln
            1315                1320                1325

His Pro Arg Thr Lys Ser Ser Arg Leu Gln Gly Ser Ser Leu Ser Ser
            1330                1335                1340

Glu Ser Ala Arg His Lys Ala Val Glu Phe Pro Ser Gly Ala Lys Ser
1345                1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
            1395                1400                1405

Pro Cys Ser Gly Met Val Ser Gly Ile Ile Ser Pro Ser Asp Leu Pro
            1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
                1445                1450                1455

Ala Pro Thr Ala Glu Lys Arg Glu Ser Gly Pro Lys Gln Ala Ala Val
            1460                1465                1470

Asn Ala Ala Val Gln Arg Val Gln Val Leu Pro Asp Ala Asp Thr Leu
            1475                1480                1485

Leu His Phe Ala Thr Glu Ser Thr Pro Asp Gly Phe Ser Cys Ser Ser
            1490                1495                1500

Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
                1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Glu Lys Asp Leu Leu Asp Asp Ser Asp
            1555                1560                1565

Asp Asp Asp Ile Glu Ile Leu Glu Glu Cys Ile Ile Ser Ala Met Pro
            1570                1575                1580

Thr Lys Ser Ser Arg Lys Gly Lys Lys Pro Ala Gln Thr Ala Ser Lys
1585                1590                1595                1600

Leu Pro Pro Pro Val Ala Arg Lys Pro Ser Gln Leu Pro Val Tyr Lys
                1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
            1635                1640                1645

Ile Asn Phe Ser Thr Ala Thr Ser Leu Ser Asp Leu Thr Ile Glu Ser
            1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
                1685                1690                1695

Thr Asp Glu Ala Gln Gly Gly Lys Thr Ser Ser Val Thr Ile Pro Glu
```

|       |       |       | 1700  |       |       |       | 1705  |       |       |       | 1710  |       |       |
|-------|-------|-------|-------|-------|-------|-------|-------|-------|-------|-------|-------|-------|-------|
| Leu | Asp | Asp | Asn | Lys | Ala | Glu | Glu | Gly | Asp | Ile | Leu | Ala | Glu | Cys | Ile |
| | | | 1715 | | | | 1720 | | | | 1725 | | |
| Asn | Ser | Ala | Met | Pro | Lys | Gly | Lys | Ser | His | Lys | Pro | Phe | Arg | Val | Lys |
| | | | 1730 | | | | 1735 | | | | 1740 | | |
| Lys | Ile | Met | Asp | Gln | Val | Gln | Gln | Ala | Ser | Ala | Ser | Ser | Ser | Ala | Pro |
| 1745 | | | | 1750 | | | | 1755 | | | | 1760 |
| Asn | Lys | Asn | Gln | Leu | Asp | Gly | Lys | Lys | Lys | Pro | Thr | Ser | Pro | Val |
| | | | | 1765 | | | | 1770 | | | | 1775 |
| Lys | Pro | Ile | Pro | Gln | Asn | Thr | Glu | Tyr | Arg | Thr | Arg | Val | Arg | Lys | Asn |
| | | | 1780 | | | | 1785 | | | | 1790 | | |
| Ala | Asp | Ser | Lys | Asn | Asn | Leu | Asn | Ala | Glu | Arg | Val | Phe | Ser | Asp | Asn |
| | | | 1795 | | | | 1800 | | | | 1805 | | |
| Lys | Asp | Ser | Lys | Lys | Gln | Asn | Leu | Lys | Asn | Asn | Ser | Lys | Asp | Phe | Asn |
| | | | 1810 | | | | 1815 | | | | 1820 | | |
| Asp | Lys | Leu | Pro | Asn | Asn | Glu | Asp | Arg | Val | Arg | Gly | Ser | Phe | Ala | Phe |
| 1825 | | | | 1830 | | | | 1835 | | | | 1840 |
| Asp | Ser | Pro | His | His | Tyr | Thr | Pro | Ile | Glu | Gly | Thr | Pro | Tyr | Cys | Phe |
| | | | | 1845 | | | | 1850 | | | | 1855 |
| Ser | Arg | Asn | Asp | Ser | Leu | Ser | Ser | Leu | Asp | Phe | Asp | Asp | Asp | Val |
| | | | 1860 | | | | 1865 | | | | 1870 | |
| Asp | Leu | Ser | Arg | Glu | Lys | Ala | Glu | Leu | Arg | Lys | Ala | Lys | Glu | Asn | Lys |
| | | | 1875 | | | | 1880 | | | | 1885 | | |
| Glu | Ser | Glu | Ala | Lys | Val | Thr | Ser | His | Thr | Glu | Leu | Thr | Ser | Asn | Gln |
| | | | 1890 | | | | 1895 | | | | 1900 | | |
| Gln | Ser | Ala | Asn | Lys | Thr | Gln | Ala | Ile | Ala | Lys | Gln | Pro | Ile | Asn | Arg |
| 1905 | | | | 1910 | | | | 1915 | | | | 1920 |
| Gly | Gln | Pro | Lys | Pro | Ile | Leu | Gln | Lys | Gln | Ser | Thr | Phe | Pro | Gln | Ser |
| | | | | 1925 | | | | 1930 | | | | 1935 |
| Ser | Lys | Asp | Ile | Pro | Asp | Arg | Gly | Ala | Ala | Thr | Asp | Glu | Lys | Leu | Gln |
| | | | | 1940 | | | | 1945 | | | | 1950 |
| Asn | Phe | Ala | Ile | Glu | Asn | Thr | Pro | Val | Cys | Phe | Ser | His | Asn | Ser | Ser |
| | | | | 1955 | | | | 1960 | | | | 1965 |
| Leu | Ser | Ser | Leu | Ser | Asp | Ile | Asp | Gln | Glu | Asn | Asn | Asn | Lys | Glu | Asn |
| | | | | 1970 | | | | 1975 | | | | 1980 |
| Glu | Pro | Ile | Lys | Glu | Thr | Glu | Pro | Pro | Asp | Ser | Gln | Gly | Glu | Pro | Ser |
| 1985 | | | | 1990 | | | | 1995 | | | | 2000 |
| Lys | Pro | Gln | Ala | Ser | Gly | Tyr | Ala | Pro | Lys | Ser | Phe | His | Val | Glu | Asp |
| | | | | 2005 | | | | 2010 | | | | 2015 |
| Thr | Pro | Val | Cys | Phe | Ser | Arg | Asn | Ser | Ser | Leu | Ser | Ser | Leu | Ser | Ile |
| | | | | 2020 | | | | 2025 | | | | 2030 |
| Asp | Ser | Glu | Asp | Asp | Leu | Leu | Gln | Glu | Cys | Ile | Ser | Ser | Ala | Met | Pro |
| | | | | 2035 | | | | 2040 | | | | 2045 |
| Lys | Lys | Lys | Lys | Pro | Ser | Arg | Leu | Lys | Gly | Asp | Asn | Glu | Lys | His | Ser |
| | | | | 2050 | | | | 2055 | | | | 2060 |
| Pro | Arg | Asn | Met | Gly | Gly | Ile | Leu | Gly | Glu | Asp | Leu | Thr | Leu | Asp | Leu |
| 2065 | | | | 2070 | | | | 2075 | | | | 2080 |
| Lys | Asp | Ile | Gln | Arg | Pro | Asp | Ser | Glu | His | Gly | Leu | Ser | Pro | Asp | Ser |
| | | | | 2085 | | | | 2090 | | | | 2095 |
| Glu | Asn | Phe | Asp | Trp | Lys | Ala | Ile | Gln | Glu | Gly | Ala | Asn | Ser | Ile | Val |
| | | | | 2100 | | | | 2105 | | | | 2110 |
| Ser | Ser | Leu | His | Gln | Ala | Ala | Ala | Ala | Ala | Cys | Leu | Ser | Arg | Gln | Ala |
| | | | | 2115 | | | | 2120 | | | | 2125 |
| Ser | Ser | Asp | Ser | Asp | Ser | Ile | Leu | Ser | Leu | Lys | Ser | Gly | Ile | Ser | Leu |
| | | | | 2130 | | | | 2135 | | | | 2140 |

Gly Ser Pro Phe His Leu Thr Pro Asp Gln Glu Glu Lys Pro Phe Thr
2145                    2150                2155                    2160

Ser Asn Lys Gly Pro Arg Ile Leu Lys Pro Gly Glu Lys Ser Thr Leu
            2165                2170                    2175

Glu Thr Lys Lys Ile Glu Ser Glu Ser Lys Gly Ile Lys Gly Gly Lys
                2180                2185                    2190

Lys Val Tyr Lys Ser Leu Ile Thr Gly Lys Val Arg Ser Asn Ser Glu
            2195                2200                2205

Ile Ser Gly Gln Met Lys Gln Pro Leu Gln Ala Asn Met Pro Ser Ile
            2210                2215                2220

Ser Arg Gly Arg Thr Met Ile His Ile Pro Gly Val Arg Asn Ser Ser
2225                    2230                2235                    2240

Ser Ser Thr Ser Pro Val Ser Lys Lys Gly Pro Pro Leu Lys Thr Pro
                2245                2250                    2255

Ala Ser Lys Ser Pro Ser Glu Gly Gln Thr Ala Thr Thr Ser Pro Arg
            2260                2265                    2270

Gly Ala Lys Pro Ser Val Lys Ser Glu Leu Ser Pro Val Ala Arg Gln
            2275                2280                    2285

Thr Ser Gln Ile Gly Gly Ser Ser Lys Ala Pro Ser Arg Ser Gly Ser
            2290                2295                2300

Arg Asp Ser Thr Pro Ser Arg Pro Ala Gln Gln Pro Leu Ser Arg Pro
2305                    2310                2315                    2320

Ile Gln Ser Pro Gly Arg Asn Ser Ile Ser Pro Gly Arg Asn Gly Ile
                2325                2330                    2335

Ser Pro Pro Asn Lys Leu Ser Gln Leu Pro Arg Thr Ser Ser Pro Ser
                2340                2345                    2350

Thr Ala Ser Thr Lys Ser Ser Gly Ser Gly Lys Met Ser Tyr Thr Ser
            2355                2360                    2365

Pro Gly Arg Gln Met Ser Gln Gln Asn Leu Thr Lys Gln Thr Gly Leu
        2370                    2375                2380

Ser Lys Asn Ala Ser Ser Ile Pro Arg Ser Glu Ser Ala Ser Lys Gly
2385                    2390                2395                    2400

Leu Asn Gln Met Asn Asn Gly Asn Gly Ala Asn Lys Lys Val Glu Leu
                2405                2410                    2415

Ser Arg Met Ser Ser Thr Lys Ser Ser Gly Ser Glu Ser Asp Arg Ser
            2420                2425                    2430

Glu Arg Pro Val Leu Val Arg Gln Ser Thr Phe Ile Lys Glu Ala Pro
        2435                    2440                2445

Ser Pro Thr Leu Arg Arg Lys Leu Glu Glu Ser Ala Ser Phe Glu Ser
2450                    2455                2460

Leu Ser Pro Ser Ser Arg Pro Ala Ser Pro Thr Arg Ser Gln Ala Gln
2465                    2470                2475                    2480

Thr Pro Val Leu Ser Pro Ser Leu Pro Asp Met Ser Leu Ser Thr His
            2485                2490                    2495

Ser Ser Val Gln Ala Gly Gly Trp Arg Lys Leu Pro Pro Asn Leu Ser
            2500                2505                    2510

Pro Thr Ile Glu Tyr Asn Asp Gly Arg Pro Ala Lys Arg His Asp Ile
        2515                    2520                2525

Ala Arg Ser His Ser Glu Ser Pro Ser Arg Leu Pro Ile Asn Arg Ser
            2530                2535                2540

Gly Thr Trp Lys Arg Glu His Ser Lys His Ser Ser Ser Leu Pro Arg
2545                    2550                2555                    2560

Val Ser Thr Trp Arg Arg Thr Gly Ser Ser Ser Ser Ile Leu Ser Ala
            2565                2570                    2575

| | | | | | | | | | | | | | | |
|---|---|---|---|---|---|---|---|---|---|---|---|---|---|---|
| Ser | Ser | Glu | Ser | Ser | Glu | Lys | Ala | Lys | Ser | Glu | Asp | Glu | Lys | His | Val |
| | | | 2580 | | | | 2585 | | | | 2590 | | | | |
| Asn | Ser | Ile | Ser | Gly | Thr | Lys | Gln | Ser | Lys | Glu | Asn | Gln | Val | Ser | Ala |
| | | | 2595 | | | | 2600 | | | | 2605 | | | | |
| Lys | Gly | Thr | Trp | Arg | Lys | Ile | Lys | Glu | Asn | Glu | Phe | Ser | Pro | Thr | Asn |
| | | | 2610 | | | | 2615 | | | | 2620 | | | | |
| Ser | Thr | Ser | Gln | Thr | Val | Ser | Ser | Gly | Ala | Thr | Asn | Gly | Ala | Glu | Ser |
| 2625 | | | | | 2630 | | | | | 2635 | | | | | 2640 |
| Lys | Thr | Leu | Ile | Tyr | Gln | Met | Ala | Pro | Ala | Val | Ser | Lys | Thr | Glu | Asp |
| | | | | 2645 | | | | 2650 | | | | | 2655 | | |
| Val | Trp | Val | Arg | Ile | Glu | Asp | Cys | Pro | Ile | Asn | Asn | Pro | Arg | Ser | Gly |
| | | | 2660 | | | | 2665 | | | | 2670 | | | | |
| Arg | Ser | Pro | Thr | Gly | Asn | Thr | Pro | Pro | Val | Ile | Asp | Ser | Val | Ser | Glu |
| | | | 2675 | | | | 2680 | | | | 2685 | | | | |
| Lys | Ala | Asn | Pro | Asn | Ile | Lys | Asp | Ser | Lys | Asp | Asn | Gln | Ala | Lys | Gln |
| | | | 2690 | | | | 2695 | | | | 2700 | | | | |
| Asn | Val | Gly | Asn | Gly | Ser | Val | Pro | Met | Arg | Thr | Val | Gly | Leu | Glu | Asn |
| 2705 | | | | | 2710 | | | | | 2715 | | | | | 2720 |
| Arg | Leu | Thr | Ser | Phe | Ile | Gln | Val | Asp | Ala | Pro | Asp | Gln | Lys | Gly | Thr |
| | | | | 2725 | | | | 2730 | | | | | 2735 | | |
| Glu | Ile | Lys | Pro | Gly | Gln | Asn | Asn | Pro | Val | Pro | Val | Ser | Glu | Thr | Asn |
| | | | 2740 | | | | 2745 | | | | 2750 | | | | |
| Glu | Ser | Pro | Ile | Val | Glu | Arg | Thr | Pro | Phe | Ser | Ser | Ser | Ser | Ser | Ser |
| | | 2755 | | | | | 2760 | | | | | 2765 | | | |
| Lys | His | Ser | Ser | Pro | Ser | Gly | Thr | Val | Ala | Ala | Arg | Val | Thr | Pro | Phe |
| | 2770 | | | | | 2775 | | | | | 2780 | | | | |
| Asn | Tyr | Asn | Pro | Ser | Pro | Arg | Lys | Ser | Ser | Ala | Asp | Ser | Thr | Ser | Ala |
| 2785 | | | | | 2790 | | | | | 2795 | | | | | 2800 |
| Arg | Pro | Ser | Gln | Ile | Pro | Thr | Pro | Val | Asn | Asn | Asn | Thr | Lys | Lys | Arg |
| | | | | 2805 | | | | 2810 | | | | | 2815 | | |
| Asp | Ser | Lys | Thr | Asp | Ser | Thr | Glu | Ser | Ser | Gly | Thr | Gln | Ser | Pro | Lys |
| | | | 2820 | | | | 2825 | | | | 2830 | | | | |
| Arg | His | Ser | Gly | Ser | Tyr | Leu | Val | Thr | Ser | Val |
| | | | 2835 | | | | 2840 | | | |

( 2 ) INFORMATION FOR SEQ ID NO:3:

( i ) SEQUENCE CHARACTERISTICS:
        ( A ) LENGTH: 3172 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP1(TB2)

( i x ) FEATURE:
        ( A ) NAME/KEY: CDS
        ( B ) LOCATION: 1..630

( x i ) SEQUENCE DESCRIPTION: SEQ ID NO:3:

| GCA | GTC | GCC | GCT | CCA | GTC | TAT | CCG | GCA | CTA | GGA | ACA | GCC | CCG | GGN | GGC | 48 |
|---|---|---|---|---|---|---|---|---|---|---|---|---|---|---|---|---|
| Ala | Val | Ala | Ala | Pro | Val | Tyr | Pro | Ala | Leu | Gly | Thr | Ala | Pro | Gly | Gly | |
| 1 | | | | 5 | | | | | 10 | | | | | 15 | | |

| GAG | ACG | GTC | CCC | GCC | ATG | TCT | GCG | GCC | ATG | AGG | GAG | AGG | TTC | GAC | CGG | 96 |
|---|---|---|---|---|---|---|---|---|---|---|---|---|---|---|---|---|
| Glu | Thr | Val | Pro | Ala | Met | Ser | Ala | Ala | Met | Arg | Glu | Arg | Phe | Asp | Arg | |
| | 20 | | | | | 25 | | | | | 30 | | | | | |

-continued

| | | | | | | | | | | | | | | | | |
|---|---|---|---|---|---|---|---|---|---|---|---|---|---|---|---|---|
| TTC | CTG | CAC | GAG | AAG | AAC | TGC | ATG | ACT | GAC | CTT | CTG | GCC | AAG | CTC | GAG | 144 |
| Phe | Leu | His<br>35 | Glu | Lys | Asn | Cys | Met<br>40 | Thr | Asp | Leu | Leu | Ala<br>45 | Lys | Leu | Glu | |
| GCC | AAA | ACC | GGC | GTG | AAC | AGG | AGC | TTC | ATC | GCT | CTT | GGT | GTC | ATC | GGA | 192 |
| Ala | Lys<br>50 | Thr | Gly | Val | Asn | Arg<br>55 | Ser | Phe | Ile | Ala | Leu<br>60 | Gly | Val | Ile | Gly | |
| CTG | GTG | GCC | TTG | TAC | CTG | GTG | TTC | GGT | TAT | GGA | GCC | TCT | CTC | CTC | TGC | 240 |
| Leu<br>65 | Val | Ala | Leu | Tyr | Leu<br>70 | Val | Phe | Gly | Tyr | Gly<br>75 | Ala | Ser | Leu | Leu | Cys<br>80 | |
| AAC | CTG | ATA | GGA | TTT | GGC | TAC | CCA | GCC | TAC | ATC | TCA | ATT | AAA | GCT | ATA | 288 |
| Asn | Leu | Ile | Gly | Phe<br>85 | Gly | Tyr | Pro | Ala | Tyr<br>90 | Ile | Ser | Ile | Lys | Ala<br>95 | Ile | |
| GAG | AGT | CCC | AAC | AAA | GAA | GAT | GAT | ACC | CAG | TGG | CTG | ACC | TAC | TGG | GTA | 336 |
| Glu | Ser | Pro | Asn<br>100 | Lys | Glu | Asp | Asp | Thr<br>105 | Gln | Trp | Leu | Thr | Tyr<br>110 | Trp | Val | |
| GTG | TAT | GGT | GTG | TTC | AGC | ATT | GCT | GAA | TTC | TTC | TCT | GAT | ATC | TTC | CTG | 384 |
| Val | Tyr | Gly<br>115 | Val | Phe | Ser | Ile | Ala<br>120 | Glu | Phe | Phe | Ser | Asp<br>125 | Ile | Phe | Leu | |
| TCA | TGG | TTC | CCC | TTC | TAC | TAC | ATG | CTG | AAG | TGT | GGC | TTC | CTG | TTG | TGG | 432 |
| Ser | Trp<br>130 | Phe | Pro | Phe | Tyr | Tyr<br>135 | Met | Leu | Lys | Cys | Gly<br>140 | Phe | Leu | Leu | Trp | |
| TGC | ATG | GCC | CCG | AGC | CCT | TCT | AAT | GGG | GCT | GAA | CTG | CTC | TAC | AAG | CGC | 480 |
| Cys<br>145 | Met | Ala | Pro | Ser | Pro<br>150 | Ser | Asn | Gly | Ala | Glu<br>155 | Leu | Leu | Tyr | Lys | Arg<br>160 | |
| ATC | ATC | CGT | CCT | TTC | TTC | CTG | AAG | CAC | GAG | TCC | CAG | ATG | GAC | AGT | GTG | 528 |
| Ile | Ile | Arg | Pro | Phe<br>165 | Phe | Leu | Lys | His | Glu<br>170 | Ser | Gln | Met | Asp | Ser<br>175 | Val | |
| GTC | AAG | GAC | CTT | AAA | GAC | AAG | TCC | AAA | GAG | ACT | GCA | GAT | GCC | ATC | ACT | 576 |
| Val | Lys | Asp | Leu<br>180 | Lys | Asp | Lys | Ser | Lys<br>185 | Glu | Thr | Ala | Asp | Ala<br>190 | Ile | Thr | |
| AAA | GAA | GCG | AAG | AAA | GCT | ACC | GTG | AAT | TTA | CTG | GGT | GAA | GAA | AAG | AAG | 624 |
| Lys | Glu | Ala<br>195 | Lys | Lys | Ala | Thr | Val<br>200 | Asn | Leu | Leu | Gly | Glu<br>205 | Glu | Lys | Lys | |
| AGC | ACC | TAAACCAGAC | | TAAACCAGAC | | TGGATGGAAA | | CTTCCTGCCC | | TCTCTGTACC | | | | | | 680 |
| Ser | Thr<br>210 | | | | | | | | | | | | | | | |

| | | | | |
|---|---|---|---|---|
| TTCCTACTGG | AGCTTGATGT | TATATTAGGG | ACTGTGGTAT | AATTATTTTA ATAATGTTGC | 740 |
| CTTGGAAACA | TTTTTGAGAT | ATTAAAGATT | GGAATGTGTT | GTAAGTTTCT TTGCTTACTT | 800 |
| TTACTGTCTA | TATATATAGG | GAGCACTTTA | AACTTAATGC | AGTGGGCAGT GTCCACGTTT | 860 |
| TTGGAAAATG | TATTTTGCCT | CTGGGTAGGA | AAAGATGTAT | GTTGCTATCC TGCAGGAAAT | 920 |
| ATAAACTTAA | AATAAAATTA | TATACCCCAC | AGGCTGTGTA | CTTTACTGGG CTCTCCCTGC | 980 |
| ACGSATTTTC | TCTGTAGTTA | CATTTAGGRT | AATCTTTATG | GTTCTACTTC CTRTAATGTA | 1040 |
| CAATTTTATA | TAATTCNGRA | ATGTTTTTAA | TGTATTTGTG | CACATGTACA TATGGAAATG | 1100 |
| TTACTGTCTG | ACTACANCAT | GCATCATGCT | CATGGGGAGG | GAGCAGGGGA AGGTTGTATG | 1160 |
| TGTCATTTAT | AACTTCTGTA | CAGTAAGACC | ACCTGCCAAA | AGCTGGAGGA ACCATTGTGC | 1220 |
| TGGTGTGGTC | TACTAAATAA | TACTTTAGGA | AATACGTGAT | TAATATGCAA GTGAACAAAG | 1280 |
| TGAGAAATGA | AATCGAATGG | AGATTGGCCT | GGTTGTTTCC | GTAGTATATG GCATATGAAT | 1340 |
| ACCAGGATAG | CTTTATAAAG | CAGTTAGTTA | GTTAGTTACT | CACTCTAGTG ATAAATCGGG | 1400 |
| AAATTTACAC | ACACACACAC | ACACACACAC | ACACACACAC | ACACACACAC ACACACACAG | 1460 |
| AGTACCCTGT | AACTCTCAAT | TCCCTGAAAA | ACTAGTAATA | CTGTCTTATC TGCTATAAAC | 1520 |
| TTTACATATT | TGTCTATTGT | CAAGATGCTA | CANTGGAMNC | CATTTCTGGT TTTATCTTCA | 1580 |
| NAGSGGAGAN | ACATGTTGAT | TTAGTCTTCT | TTCCCAATCT | TCTTTTTTAA MCCAGTTTNA | 1640 |
| GGMNCTTCTG | RAGATTTGYC | CACCTCTGAT | TACATGTATG | TTCTYGTTTG TATCATKAGC | 1700 |

| | | | | | |
|---|---|---|---|---|---|
| AACAACATGC | TAATGRCGAC | ACCTAGCTCT | RAGMGCAATT | CTGGGAGANT | GARAGGNWGT | 1760 |
| ATARAGTMNC | CCATAATCTG | CTTGGCAATA | GTTAAGTCAA | TCTATCTTCA | GTTTTCTCT | 1820 |
| GGCCTTTAAG | GTCAAACACA | AGAGGCTTCC | CTAGTTTACA | AGTCAGAGTC | ACTTGTAGTC | 1880 |
| CATTTAAATG | CCCTCATCCG | TATTCTTTGT | GTTGATAAGC | TGCACAKGAC | TACATAGTAA | 1940 |
| GTACAGANCA | GTAAAGTTAA | NNCGGATGTC | TCCATTGATC | TGCCAANTCG | NTATAGAGAG | 2000 |
| CAATTTGTCT | GGACTAGAAA | ATCTGAGTTT | TACACCATAC | TGTTAAGAGT | CCTTTTGAAT | 2060 |
| TAAACTAGAC | TAAAACAAGT | GTATAACTAA | ACTAACAAGA | TTAAATATCC | AGCCAGTACA | 2120 |
| GTATTTTTTA | AGGCAAATAA | AGATGATTAG | CTCACCTTGA | GNTAACAATC | AGGTAAGATC | 2180 |
| ATNACAATGT | CTCATGATGT | NAANAATATT | AAAGATATCA | ATACTAAGTG | ACAGTATCAC | 2240 |
| NNCTAATATA | ATATGGATCA | GAGCATTTAT | TTTGGGGAGG | AAAACAGTGG | TGATTACCGG | 2300 |
| CATTTTATTA- | AACTTAAAAC | TTTGTAGAAA | GCAAACAAAA | TTGTTCTTGG | GAGAAAATCA | 2360 |
| ACTTTTAGAT | TAAAAAAATT | TTAAGTAWCT | AGGAGTATTT | AAATCCTTTT | CCCATAAATA | 2420 |
| AAAGTACAGT | TTTCTTGGTG | GCAGAATGAA | AATCAGCAAC | NTCTAGCATA | TAGACTATAT | 2480 |
| AATCAGATTG | ACAGCATATA | GAATATATTA | TCAGACAAGA | TGAGGAGGTA | CAAAAGTTAC | 2540 |
| TATTGCTCAT | AATGACTTAC | AGGCTAAAAN | TAGNTNTAAA | ATACTATATT | AAATTCTGAA | 2600 |
| TGCAATTTTT | TTTTGTTCCC | TTGAGACCAA | AATTTAAGTT | AACTGTTGCT | GGCAGTCTAA | 2660 |
| GTGTAAATGT | TAACAGCAGG | AGAAGTTAAG | AATTGAGCAG | TTCTGTTGCA | TGATTTCCCA | 2720 |
| AATGAAATAC | TGCCTTGGCT | AGAGTTTGAA | AAACTAATTG | AGCCTGTGCC | TGGCTAGAAA | 2780 |
| ACAAGCGTTT | ATTTGAATGT | GAATAGTGTT | TCAAGGTAT | GTAGTTACAG | AATTCCTACC | 2840 |
| AAACAGCTTA | AATTCTTCAA | GAAAGAATTC | CTGCAGCAGT | TATTCCCTTA | CCTGAAGGCT | 2900 |
| TCAATCATTT | GGATCAACAA | CTGCTACTCT | CGGGAAGACT | CCTCTACTCA | CAGCTGAAGA | 2960 |
| AAATGAGCAC | ACCCTTCACA | CTGTTATCAC | CTATCCTGAA | GATGTGATAC | ACTGAATGGA | 3020 |
| AATAAATAGA | TGTAAATAAA | ATTGAGWTCT | CATTTAAAAA | AAACCATGTG | CCCAATGGGA | 3080 |
| AAATGACCTC | ATGTTGTGGT | TTAAACAGCA | ACTGCACCCA | CTAGCACAGC | CCATTGAGCT | 3140 |
| ANCCTATATA | TACATCTCTG | TCAGTGCCCC | TC | | | 3172 |

( 2 ) INFORMATION FOR SEQ ID NO:4:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala  Val  Ala  Ala  Pro  Val  Tyr  Pro  Ala  Leu  Gly  Thr  Ala  Pro  Gly  Gly
  1                5                   10                  15

Glu  Thr  Val  Pro  Ala  Met  Ser  Ala  Ala  Met  Arg  Glu  Arg  Phe  Asp  Arg
                20                  25                  30

Phe  Leu  His  Glu  Lys  Asn  Cys  Met  Thr  Asp  Leu  Leu  Ala  Lys  Leu  Glu
            35                  40                  45

Ala  Lys  Thr  Gly  Val  Asn  Arg  Ser  Phe  Ile  Ala  Leu  Gly  Val  Ile  Gly
    50                  55                  60

Leu  Val  Ala  Leu  Tyr  Leu  Val  Phe  Gly  Tyr  Gly  Ala  Ser  Leu  Leu  Cys
 65                  70                  75                  80

Asn  Leu  Ile  Gly  Phe  Gly  Tyr  Pro  Ala  Tyr  Ile  Ser  Ile  Lys  Ala  Ile
                85                  90                  95

Glu  Ser  Pro  Asn  Lys  Glu  Asp  Asp  Thr  Gln  Trp  Leu  Thr  Tyr  Trp  Val
            100                 105                 110
```

-continued

| | | | | | | | | | | | | | | |
|---|---|---|---|---|---|---|---|---|---|---|---|---|---|---|
| Val | Tyr | Gly 115 | Val | Phe | Ser | Ile | Ala 120 | Glu | Phe | Phe | Ser | Asp 125 | Ile | Phe | Leu |
| Ser | Trp 130 | Phe | Pro | Phe | Tyr | Tyr 135 | Met | Leu | Lys | Cys | Gly 140 | Phe | Leu | Leu | Trp |
| Cys 145 | Met | Ala | Pro | Ser | Pro 150 | Ser | Asn | Gly | Ala | Glu 155 | Leu | Leu | Tyr | Lys | Arg 160 |
| Ile | Ile | Arg | Pro | Phe 165 | Phe | Leu | Lys | His | Glu 170 | Ser | Gln | Met | Asp | Ser 175 | Val |
| Val | Lys | Asp | Leu 180 | Lys | Asp | Lys | Ser | Lys 185 | Glu | Thr | Ala | Asp | Ala 190 | Ile | Thr |
| Lys | Glu | Ala 195 | Lys | Lys | Ala | Thr | Val 200 | Asn | Leu | Leu | Gly | Glu 205 | Lys | Lys |
| Ser | Thr 210 | | | | | | | | | | | | | |

(2) INFORMATION FOR SEQ ID NO:5:

(i) SEQUENCE CHARACTERISTICS:
        (A) LENGTH: 434 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: TB1

(xi) SEQUENCE DESCRIPTION: SEQ ID NO:5:

| | | | | | | | | | | | | | | |
|---|---|---|---|---|---|---|---|---|---|---|---|---|---|---|
| Val 1 | Ala | Pro | Val | Val 5 | Val | Gly | Ser | Gly | Arg 10 | Ala | Pro | Arg | His | Pro 15 | Ala |
| Pro | Ala | Ala | Met 20 | His | Pro | Arg | Arg | Pro 25 | Asp | Gly | Phe | Asp | Gly 30 | Leu | Gly |
| Tyr | Arg | Gly 35 | Gly | Ala | Arg | Asp | Glu 40 | Gln | Gly | Phe | Gly | Gly 45 | Ala | Phe | Pro |
| Ala | Arg 50 | Ser | Phe | Ser | Thr | Gly 55 | Ser | Asp | Leu | Gly | His 60 | Trp | Val | Thr | Thr |
| Pro 65 | Pro | Asp | Ile | Pro | Gly 70 | Ser | Arg | Asn | Leu | His 75 | Trp | Gly | Glu | Lys | Ser 80 |
| Pro | Pro | Tyr | Gly | Val 85 | Pro | Thr | Thr | Ser | Thr 90 | Pro | Tyr | Glu | Gly | Pro 95 | Thr |
| Glu | Glu | Pro | Phe 100 | Ser | Ser | Gly | Gly | Gly 105 | Gly | Ser | Val | Gln | Gly 110 | Gln | Ser |
| Ser | Glu | Gln 115 | Leu | Asn | Arg | Phe | Ala 120 | Gly | Phe | Gly | Ile | Gly 125 | Leu | Ala | Ser |
| Leu | Phe 130 | Thr | Glu | Asn | Val | Leu 135 | Ala | His | Pro | Cys | Ile 140 | Val | Leu | Arg | Arg |
| Gln | Cys 145 | Gln | Val | Asn | Tyr 150 | His | Ala | Gln | His | Tyr 155 | His | Leu | Thr | Pro | Phe 160 |
| Thr | Val | Ile | Asn | Ile 165 | Met | Tyr | Ser | Phe | Asn 170 | Lys | Thr | Gln | Gly | Pro 175 | Arg |
| Ala | Leu | Trp | Lys 180 | Gly | Met | Gly | Ser | Thr 185 | Phe | Ile | Val | Gln | Gly 190 | Val | Thr |
| Leu | Gly | Ala 195 | Glu | Gly | Ile | Ile | Ser 200 | Glu | Phe | Thr | Pro | Leu 205 | Pro | Arg | Glu |
| Val | Leu 210 | His | Lys | Trp | Ser | Pro 215 | Lys | Gln | Ile | Gly | Glu 220 | His | Leu | Leu | Leu |

| | | | | | | | | | | | | | | | |
|---|---|---|---|---|---|---|---|---|---|---|---|---|---|---|---|
| Lys<br>225 | Ser | Leu | Thr | Tyr | Val<br>230 | Val | Ala | Met | Pro | Phe<br>235 | Tyr | Ser | Ala | Ser | Leu<br>240 |
| Ile | Glu | Thr | Val | Gln<br>245 | Ser | Glu | Ile | Ile | Arg<br>250 | Asp | Asn | Thr | Gly | Ile<br>255 | Leu |
| Glu | Cys | Val | Lys<br>260 | Glu | Gly | Ile | Gly | Arg<br>265 | Val | Ile | Gly | Met | Gly<br>270 | Val | Pro |
| His | Ser | Lys<br>275 | Arg | Leu | Leu | Pro | Leu<br>280 | Leu | Ser | Leu | Ile | Phe<br>285 | Pro | Thr | Val |
| Leu | His<br>290 | Gly | Val | Leu | His | Tyr<br>295 | Ile | Ile | Ser | Ser | Val<br>300 | Ile | Gln | Lys | Phe |
| Val<br>305 | Leu | Leu | Ile | Leu | Lys<br>310 | Arg | Lys | Thr | Tyr | Asn<br>315 | Ser | His | Leu | Ala | Glu<br>320 |
| Ser | Thr | Ser | Pro | Val<br>325 | Gln | Ser | Met | Leu | Asp<br>330 | Ala | Tyr | Phe | Pro | Glu<br>335 | Leu |
| Ile | Ala | Asn | Phe<br>340 | Ala | Ala | Ser | Leu | Cys<br>345 | Ser | Asp | Val | Ile | Leu<br>350 | Tyr | Pro |
| Leu | Glu | Thr<br>355 | Val | Leu | His | Arg | Leu<br>360 | His | Ile | Gln | Gly | Thr<br>365 | Arg | Thr | Ile |
| Ile | Asp<br>370 | Asn | Thr | Asp | Leu<br>375 | Gly | Tyr | Glu | Val | Leu<br>380 | Pro | Ile | Asn | Thr | Gln |
| Tyr<br>385 | Glu | Gly | Met | Arg | Asp<br>390 | Cys | Ile | Asn | Thr | Ile<br>395 | Arg | Gln | Glu | Glu | Gly<br>400 |
| Val | Phe | Gly | Phe | Tyr<br>405 | Lys | Gly | Phe | Gly | Ala<br>410 | Val | Ile | Ile | Gln | Tyr<br>415 | Thr |
| Leu | His | Ala | Ala<br>420 | Val | Leu | Gln | Ile | Thr<br>425 | Lys | Ile | Ile | Tyr | Ser<br>430 | Thr | Leu |
| Leu | Gln | | | | | | | | | | | | | | |

( 2 ) INFORMATION FOR SEQ ID NO:6:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: YS-39(TB2)

( x i ) SEQUENCE DESCRIPTION: SEQ ID NO:6:

| | | | | | | | | | | | | | | | |
|---|---|---|---|---|---|---|---|---|---|---|---|---|---|---|---|
| Glu<br>1 | Leu | Arg | Arg | Phe<br>5 | Asp | Arg | Phe | Leu | His<br>10 | Glu | Lys | Asn | Cys | Met<br>15 | Thr |
| Asp | Leu | Leu | Ala<br>20 | Lys | Leu | Glu | Ala | Lys<br>25 | Thr | Gly | Val | Asn | Arg<br>30 | Ser | Phe |
| Ile | Ala | Leu<br>35 | Gly | Val | Ile | Gly | Leu<br>40 | Val | Ala | Leu | Tyr | Leu<br>45 | Val | Phe | Gly |
| Tyr | Gly<br>50 | Ala | Ser | Leu | Leu | Cys<br>55 | Asn | Leu | Ile | Gly | Phe<br>60 | Gly | Tyr | Pro | Ala |
| Tyr<br>65 | Ile | Ser | Ile | Lys | Ala<br>70 | Ile | Glu | Ser | Pro | Asn<br>75 | Lys | Glu | Asp | Asp<br>80 | Thr |
| Gln | Trp | Leu | Thr | Tyr<br>85 | Trp | Val | Val | Tyr | Gly<br>90 | Val | Phe | Ser | Ile | Ala<br>95 | Glu |
| Phe | Phe | Ser | Asp<br>100 | Ile | Phe | Leu | Ser | Trp<br>105 | Phe | Pro | Phe | Tyr | Tyr<br>110 | Ile | Leu |

```
Lys  Cys  Gly  Phe  Leu  Leu  Trp  Cys  Met  Ala  Pro  Ser  Pro  Ser  Asn  Gly
          115                      120                 125

Ala  Glu  Leu  Leu  Tyr  Lys  Arg  Ile  Ile  Arg  Pro  Phe  Phe  Leu  Lys  His
     130                      135                 140

Glu  Ser  Gln  Met  Asp  Ser  Val  Val  Lys  Asp  Leu  Lys  Asp  Lys  Ala  Lys
145                      150                      155                      160

Glu  Thr  Ala  Asp  Ala  Ile  Thr  Lys  Glu  Ala  Lys  Lys  Ala  Thr  Val  Asn
                    165                 170                           175

Leu  Leu  Gly  Glu  Glu  Lys  Lys  Ser  Thr
               180                 185
```

( 2 ) INFORMATION FOR SEQ ID NO:7:

( i ) SEQUENCE CHARACTERISTICS:
        ( A ) LENGTH: 2842 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: APC ( x i ) SEQUENCE DESCRIPTION: SEQ ID NO:7:

```
Met  Ala  Ala  Ala  Ser  Tyr  Asp  Gln  Leu  Leu  Lys  Gln  Val  Glu  Ala  Leu
1                   5                      10                      15

Lys  Met  Glu  Asn  Ser  Asn  Leu  Arg  Gln  Glu  Leu  Glu  Asp  Asn  Ser  Asn
               20                 25                      30

His  Leu  Thr  Lys  Leu  Glu  Thr  Glu  Ala  Ser  Asn  Met  Lys  Glu  Val  Leu
          35                 40                      45

Lys  Gln  Leu  Gln  Gly  Ser  Ile  Glu  Asp  Glu  Ala  Met  Ala  Ser  Ser  Gly
     50                      55                      60

Gln  Ile  Asp  Leu  Leu  Glu  Arg  Leu  Lys  Glu  Leu  Asn  Leu  Asp  Ser  Ser
65                      70                 75                           80

Asn  Phe  Pro  Gly  Val  Lys  Leu  Arg  Ser  Lys  Met  Ser  Leu  Arg  Ser  Tyr
               85                 90                           95

Gly  Ser  Arg  Glu  Gly  Ser  Val  Ser  Ser  Arg  Ser  Gly  Glu  Cys  Ser  Pro
               100                105                      110

Val  Pro  Met  Gly  Ser  Phe  Pro  Arg  Arg  Gly  Phe  Val  Asn  Gly  Ser  Arg
          115                      120                 125

Glu  Ser  Thr  Gly  Tyr  Leu  Glu  Glu  Leu  Glu  Lys  Glu  Arg  Ser  Leu  Leu
     130                      135                 140

Leu  Ala  Asp  Leu  Asp  Lys  Glu  Glu  Lys  Glu  Lys  Asp  Trp  Tyr  Tyr  Ala
145                      150                      155                      160

Gln  Leu  Gln  Asn  Leu  Thr  Lys  Arg  Ile  Asp  Ser  Leu  Leu  Thr  Glu  Asn
                    165                 170                           175

Phe  Ser  Leu  Gln  Thr  Asp  Met  Thr  Arg  Arg  Gln  Leu  Glu  Tyr  Glu  Ala
               180                 185                      190

Arg  Gln  Ile  Arg  Val  Ala  Met  Glu  Glu  Gln  Leu  Gly  Thr  Cys  Gln  Asp
               195                 200                      205

Met  Glu  Lys  Arg  Ala  Gln  Arg  Arg  Ile  Ala  Arg  Ile  Gln  Gln  Ile  Glu
     210                      215                      220

Lys  Asp  Ile  Leu  Arg  Ile  Arg  Gln  Leu  Leu  Gln  Ser  Gln  Ala  Thr  Glu
225                      230                      235                      240

Ala  Glu  Arg  Ser  Ser  Gln  Asn  Lys  His  Glu  Thr  Gly  Ser  His  Asp  Ala
                    245                 250                           255
```

| | | | | | | | | | | | | | | |
|---|---|---|---|---|---|---|---|---|---|---|---|---|---|---|
|Glu|Arg|Gln|Asn<br>260|Glu|Gly|Gln|Gly|Val<br>265|Gly|Glu|Ile|Asn|Met<br>270|Ala|Thr|
|Ser|Gly|Asn<br>275|Gly|Gln|Gly|Ser|Thr<br>280|Thr|Arg|Met|Asp|His<br>285|Glu|Thr|Ala|
|Ser|Val<br>290|Leu|Ser|Ser|Ser|Ser<br>295|Thr|His|Ser|Ala|Pro<br>300|Arg|Arg|Leu|Thr|
|Ser<br>305|His|Leu|Gly|Thr|Lys<br>310|Val|Glu|Met|Val|Tyr<br>315|Ser|Leu|Leu|Ser|Met<br>320|
|Leu|Gly|Thr|His|Asp<br>325|Lys|Asp|Asp|Met|Ser<br>330|Arg|Thr|Leu|Leu|Ala<br>335|Met|
|Ser|Ser|Ser|Gln<br>340|Asp|Ser|Cys|Ile|Ser<br>345|Met|Arg|Gln|Ser|Gly<br>350|Cys|Leu|
|Pro|Leu|Leu<br>355|Ile|Gln|Leu|Leu|His<br>360|Gly|Asn|Asp|Lys|Asp<br>365|Ser|Val|Leu|
|Leu|Gly<br>370|Asn|Ser|Arg|Gly|Ser<br>375|Lys|Glu|Ala|Arg|Ala<br>380|Arg|Ala|Ser|Ala|
|Ala<br>385|Leu|His|Asn|Ile|Ile<br>390|His|Ser|Gln|Pro|Asp<br>395|Asp|Lys|Arg|Gly|Arg<br>400|
|Arg|Glu|Ile|Arg|Val<br>405|Leu|His|Leu|Leu|Glu<br>410|Gln|Ile|Arg|Ala|Tyr<br>415|Cys|
|Glu|Thr|Cys|Trp<br>420|Glu|Trp|Gln|Glu|Ala<br>425|His|Glu|Pro|Gly|Met<br>430|Asp|Gln|
|Asp|Lys|Asn<br>435|Pro|Met|Pro|Ala|Pro<br>440|Val|Glu|His|Gln|Ile<br>445|Cys|Pro|Ala|
|Val|Cys<br>450|Val|Leu|Met|Lys|Leu<br>455|Ser|Phe|Asp|Glu|Glu<br>460|His|Arg|His|Ala|
|Met<br>465|Asn|Glu|Leu|Gly|Gly<br>470|Leu|Gln|Ala|Ile|Ala<br>475|Glu|Leu|Leu|Gln|Val<br>480|
|Asp|Cys|Glu|Met|Tyr<br>485|Gly|Leu|Thr|Asn|Asp<br>490|His|Tyr|Ser|Ile|Thr<br>495|Leu|
|Arg|Arg|Tyr|Ala<br>500|Gly|Met|Ala|Leu|Thr<br>505|Asn|Leu|Thr|Phe|Gly<br>510|Asp|Val|
|Ala|Asn|Lys<br>515|Ala|Thr|Leu|Cys|Ser<br>520|Met|Lys|Gly|Cys|Met<br>525|Arg|Ala|Leu|
|Val|Ala<br>530|Gln|Leu|Lys|Ser|Glu<br>535|Ser|Glu|Asp|Leu|Gln<br>540|Gln|Val|Ile|Ala|
|Ser<br>545|Val|Leu|Arg|Asn|Leu<br>550|Ser|Trp|Arg|Ala|Asp<br>555|Val|Asn|Ser|Lys|Lys<br>560|
|Thr|Leu|Arg|Glu|Val<br>565|Gly|Ser|Val|Lys|Ala<br>570|Leu|Met|Glu|Cys|Ala<br>575|Leu|
|Glu|Val|Lys|Lys<br>580|Glu|Ser|Thr|Leu|Lys<br>585|Ser|Val|Leu|Ser|Ala<br>590|Leu|Trp|
|Asn|Leu|Ser<br>595|Ala|His|Cys|Thr|Glu<br>600|Asn|Lys|Ala|Asp|Ile<br>605|Cys|Ala|Val|
|Asp|Gly<br>610|Ala|Leu|Ala|Phe|Leu<br>615|Val|Gly|Thr|Leu|Thr<br>620|Tyr|Arg|Ser|Gln|
|Thr<br>625|Asn|Thr|Leu|Ala|Ile<br>630|Ile|Glu|Ser|Gly|Gly<br>635|Gly|Ile|Leu|Arg|Asn<br>640|
|Val|Ser|Ser|Leu|Ile<br>645|Ala|Thr|Asn|Glu|Asp<br>650|His|Arg|Gln|Ile|Leu<br>655|Arg|
|Glu|Asn|Asn|Cys<br>660|Leu|Gln|Thr|Leu|Leu<br>665|Gln|His|Leu|Lys|Ser<br>670|His|Ser|
|Leu|Thr|Ile<br>675|Val|Ser|Asn|Ala|Cys<br>680|Gly|Thr|Leu|Trp|Asn<br>685|Leu|Ser|Ala|
|Arg|Asn|Pro|Lys|Asp|Gln|Glu|Ala|Leu|Trp|Asp|Met|Gly|Ala|Val|Ser|

|     |     |     |     | 690 |     |     |     | 695 |     |     |     | 700 |     |     |
| --- | --- | --- | --- | --- | --- | --- | --- | --- | --- | --- | --- | --- | --- | --- |
| Met | Leu | Lys | Asn | Leu | Ile | His | Ser | Lys | His | Lys | Met | Ile | Ala | Met | Gly |
| 705 |     |     |     |     | 710 |     |     |     | 715 |     |     |     |     | 720 |     |
| Ser | Ala | Ala | Ala | Leu | Arg | Asn | Leu | Met | Ala | Asn | Arg | Pro | Ala | Lys | Tyr |
|     |     |     |     |     | 725 |     |     |     | 730 |     |     |     |     | 735 |     |
| Lys | Asp | Ala | Asn | Ile | Met | Ser | Pro | Gly | Ser | Ser | Leu | Pro | Ser | Leu | His |
|     |     |     |     | 740 |     |     |     | 745 |     |     |     |     | 750 |     |     |
| Val | Arg | Lys | Gln | Lys | Ala | Leu | Glu | Ala | Glu | Leu | Asp | Ala | Gln | His | Leu |
|     |     | 755 |     |     |     |     | 760 |     |     |     |     | 765 |     |     |     |
| Ser | Glu | Thr | Phe | Asp | Asn | Ile | Asp | Asn | Leu | Ser | Pro | Lys | Ala | Ser | His |
|     | 770 |     |     |     |     | 775 |     |     |     |     | 780 |     |     |     |     |
| Arg | Ser | Lys | Gln | Arg | His | Lys | Gln | Ser | Leu | Tyr | Gly | Asp | Tyr | Val | Phe |
| 785 |     |     |     |     | 790 |     |     |     |     | 795 |     |     |     |     | 800 |
| Asp | Thr | Asn | Arg | His | Asp | Asp | Asn | Arg | Ser | Asp | Asn | Phe | Asn | Thr | Gly |
|     |     |     |     | 805 |     |     |     |     | 810 |     |     |     |     | 815 |     |
| Asn | Met | Thr | Val | Leu | Ser | Pro | Tyr | Leu | Asn | Thr | Thr | Val | Leu | Pro | Ser |
|     |     |     | 820 |     |     |     |     | 825 |     |     |     |     | 830 |     |     |
| Ser | Ser | Ser | Ser | Arg | Gly | Ser | Leu | Asp | Ser | Ser | Arg | Ser | Glu | Lys | Asp |
|     |     | 835 |     |     |     |     | 840 |     |     |     |     | 845 |     |     |     |
| Arg | Ser | Leu | Glu | Arg | Glu | Arg | Gly | Ile | Gly | Leu | Gly | Asn | Tyr | His | Pro |
| 850 |     |     |     |     | 855 |     |     |     |     | 860 |     |     |     |     |     |
| Ala | Thr | Glu | Asn | Pro | Gly | Thr | Ser | Ser | Lys | Arg | Gly | Leu | Gln | Ile | Ser |
| 865 |     |     |     |     | 870 |     |     |     |     | 875 |     |     |     |     | 880 |
| Thr | Thr | Ala | Ala | Gln | Ile | Ala | Lys | Val | Met | Glu | Glu | Val | Ser | Ala | Ile |
|     |     |     |     | 885 |     |     |     |     | 890 |     |     |     |     | 895 |     |
| His | Thr | Ser | Gln | Glu | Asp | Arg | Ser | Ser | Gly | Ser | Thr | Thr | Glu | Leu | His |
|     |     |     | 900 |     |     |     |     | 905 |     |     |     |     | 910 |     |     |
| Cys | Val | Thr | Asp | Glu | Arg | Asn | Ala | Leu | Arg | Arg | Ser | Ser | Ala | Ala | His |
|     |     |     | 915 |     |     |     |     | 920 |     |     |     |     | 925 |     |     |
| Thr | His | Ser | Asn | Thr | Tyr | Asn | Phe | Thr | Lys | Ser | Glu | Asn | Ser | Asn | Arg |
|     | 930 |     |     |     |     | 935 |     |     |     |     | 940 |     |     |     |     |
| Thr | Cys | Ser | Met | Pro | Tyr | Ala | Lys | Leu | Glu | Tyr | Lys | Arg | Ser | Ser | Asn |
| 945 |     |     |     |     | 950 |     |     |     |     | 955 |     |     |     |     | 960 |
| Asp | Ser | Leu | Asn | Ser | Val | Ser | Ser | Ser | Asp | Gly | Tyr | Gly | Lys | Arg | Gly |
|     |     |     |     | 965 |     |     |     |     | 970 |     |     |     |     | 975 |     |
| Gln | Met | Lys | Pro | Ser | Ile | Glu | Ser | Tyr | Ser | Glu | Asp | Asp | Glu | Ser | Lys |
|     |     |     | 980 |     |     |     |     | 985 |     |     |     |     | 990 |     |     |
| Phe | Cys | Ser | Tyr | Gly | Gln | Tyr | Pro | Ala | Asp | Leu | Ala | His | Lys | Ile | His |
|     |     | 995 |     |     |     |     | 1000|     |     |     |     | 1005|     |     |     |
| Ser | Ala | Asn | His | Met | Asp | Asp | Asn | Asp | Gly | Glu | Leu | Asp | Thr | Pro | Ile |
|     |     |     | 1010|     |     |     |     | 1015|     |     |     |     | 1020|     |     |
| Asn | Tyr | Ser | Leu | Lys | Tyr | Ser | Asp | Glu | Gln | Leu | Asn | Ser | Gly | Arg | Gln |
| 1025|     |     |     |     | 1030|     |     |     |     | 1035|     |     |     |     | 1040|
| Ser | Pro | Ser | Gln | Asn | Glu | Arg | Trp | Ala | Arg | Pro | Lys | His | Ile | Ile | Glu |
|     |     |     |     | 1045|     |     |     |     | 1050|     |     |     |     | 1055|     |
| Asp | Glu | Ile | Lys | Gln | Ser | Glu | Gln | Arg | Gln | Ser | Arg | Asn | Gln | Ser | Thr |
|     |     |     |     | 1060|     |     |     |     | 1065|     |     |     |     | 1070|     |
| Thr | Tyr | Pro | Val | Tyr | Thr | Glu | Ser | Thr | Asp | Asp | Lys | His | Leu | Lys | Phe |
|     |     |     | 1075|     |     |     |     | 1080|     |     |     |     | 1085|     |     |
| Gln | Pro | His | Phe | Gly | Gln | Gln | Glu | Cys | Val | Ser | Pro | Tyr | Arg | Ser | Arg |
|     |     |     | 1090|     |     |     |     | 1095|     |     |     |     | 1100|     |     |
| Gly | Ala | Asn | Gly | Ser | Glu | Thr | Asn | Arg | Val | Gly | Ser | Asn | His | Gly | Ile |
| 1105|     |     |     |     | 1110|     |     |     |     | 1115|     |     |     |     | 1120|
| Asn | Gln | Asn | Val | Ser | Gln | Ser | Leu | Cys | Gln | Glu | Asp | Asp | Tyr | Glu | Asp |
|     |     |     |     | 1125|     |     |     |     | 1130|     |     |     |     | 1135|     |

```
Asp  Lys  Pro  Thr  Asn  Tyr  Ser  Glu  Arg  Tyr  Ser  Glu  Glu  Gln  His
               1140                      1145                 1150

Glu  Glu  Glu  Glu  Arg  Pro  Thr  Asn  Tyr  Ser  Ile  Lys  Tyr  Asn  Glu  Glu
          1155                      1160                 1165

Lys  Arg  His  Val  Asp  Gln  Pro  Ile  Asp  Tyr  Ser  Leu  Lys  Tyr  Ala  Thr
     1170                      1175                      1180

Asp  Ile  Pro  Ser  Ser  Gln  Lys  Gln  Ser  Phe  Ser  Phe  Ser  Lys  Ser  Ser
1185                      1190                      1195                      1200

Ser  Gly  Gln  Ser  Ser  Lys  Thr  Glu  His  Met  Ser  Ser  Ser  Ser  Glu  Asn
                    1205                      1210                      1215

Thr  Ser  Thr  Pro  Ser  Ser  Asn  Ala  Lys  Arg  Gln  Asn  Gln  Leu  His  Pro
               1220                      1225                 1230

Ser  Ser  Ala  Gln  Ser  Arg  Ser  Gly  Gln  Pro  Gln  Lys  Ala  Ala  Thr  Cys
               1235                      1240                      1245

Lys  Val  Ser  Ser  Ile  Asn  Gln  Glu  Thr  Ile  Gln  Thr  Tyr  Cys  Val  Glu
     1250                      1255                      1260

Asp  Thr  Pro  Ile  Cys  Phe  Ser  Arg  Cys  Ser  Ser  Leu  Ser  Ser  Leu  Ser
1265                      1270                      1275                      1280

Ser  Ala  Glu  Asp  Glu  Ile  Gly  Cys  Asn  Gln  Thr  Thr  Gln  Glu  Ala  Asp
                    1285                      1290                      1295

Ser  Ala  Asn  Thr  Leu  Gln  Ile  Ala  Glu  Ile  Lys  Glu  Lys  Ile  Gly  Thr
               1300                      1305                      1310

Arg  Ser  Ala  Glu  Asp  Pro  Val  Ser  Glu  Val  Pro  Ala  Val  Ser  Gln  His
          1315                      1320                      1325

Pro  Arg  Thr  Lys  Ser  Ser  Arg  Leu  Gln  Gly  Ser  Ser  Leu  Ser  Ser  Glu
          1330                      1335                      1340

Ser  Ala  Arg  His  Lys  Ala  Val  Glu  Phe  Ser  Ser  Gly  Ala  Lys  Ser  Pro
1345                      1350                      1355                      1360

Ser  Lys  Ser  Gly  Ala  Gln  Thr  Pro  Lys  Ser  Pro  Pro  Glu  His  Tyr  Val
                    1365                      1370                      1375

Gln  Glu  Thr  Pro  Leu  Met  Phe  Ser  Arg  Cys  Thr  Ser  Val  Ser  Ser  Leu
               1380                      1385                      1390

Asp  Ser  Phe  Glu  Ser  Arg  Ser  Ile  Ala  Ser  Ser  Val  Gln  Ser  Glu  Pro
          1395                      1400                      1405

Cys  Ser  Gly  Met  Val  Ser  Gly  Ile  Ile  Ser  Pro  Ser  Asp  Leu  Pro  Asp
     1410                      1415                      1420

Ser  Pro  Gly  Gln  Thr  Met  Pro  Pro  Ser  Arg  Ser  Lys  Thr  Pro  Pro  Pro
1425                      1430                      1435                      1440

Pro  Pro  Gln  Thr  Ala  Gln  Thr  Lys  Arg  Glu  Val  Pro  Lys  Asn  Lys  Ala
               1445                      1450                      1455

Pro  Thr  Ala  Glu  Lys  Arg  Glu  Ser  Gly  Pro  Lys  Gln  Ala  Ala  Val  Asn
          1460                      1465                      1470

Ala  Ala  Val  Gln  Arg  Val  Gln  Val  Leu  Pro  Asp  Ala  Asp  Thr  Leu  Leu
          1475                      1480                      1485

His  Phe  Ala  Thr  Glu  Ser  Thr  Pro  Asp  Gly  Phe  Ser  Cys  Ser  Ser  Ser
          1490                      1495                      1500

Leu  Ser  Ala  Leu  Ser  Leu  Asp  Glu  Pro  Phe  Ile  Gln  Lys  Asp  Val  Glu
1505                      1510                      1515                      1520

Leu  Arg  Ile  Met  Pro  Pro  Val  Gln  Glu  Asn  Asp  Asn  Gly  Asn  Glu  Thr
                    1525                      1530                      1535

Glu  Ser  Glu  Gln  Pro  Lys  Glu  Ser  Asn  Glu  Asn  Gln  Glu  Lys  Glu  Ala
               1540                      1545                      1550

Glu  Lys  Thr  Ile  Asp  Ser  Glu  Lys  Asp  Leu  Leu  Asp  Asp  Ser  Asp  Asp
          1555                      1560                      1565
```

```
Asp Asp Ile Glu Ile Leu Glu Glu Cys Ile Ile Ser Ala Met Pro Thr
    1570            1575               1580
Lys Ser Ser Arg Lys Ala Lys Lys Pro Ala Gln Thr Ala Ser Lys Leu
1585            1590              1595               1600
Pro Pro Pro Val Ala Arg Lys Pro Ser Gln Leu Pro Val Tyr Lys Leu
                1605              1610              1615
Leu Pro Ser Gln Asn Arg Leu Gln Pro Gln Lys His Val Ser Phe Thr
            1620              1625              1630
Pro Gly Asp Asp Met Pro Arg Val Tyr Cys Val Glu Gly Thr Pro Ile
            1635              1640              1645
Asn Phe Ser Thr Ala Thr Ser Leu Ser Asp Leu Thr Ile Glu Ser Pro
    1650              1655              1660
Pro Asn Glu Leu Ala Ala Gly Glu Gly Val Arg Gly Gly Ala Gln Ser
1665              1670              1675              1680
Gly Glu Phe Glu Lys Arg Asp Thr Ile Pro Thr Glu Gly Arg Ser Thr
                1685              1690              1695
Asp Glu Ala Gln Gly Gly Lys Thr Ser Ser Val Thr Ile Pro Glu Leu
            1700              1705              1710
Asp Asp Asn Lys Ala Glu Glu Gly Asp Ile Leu Ala Glu Cys Ile Asn
            1715              1720              1725
Ser Ala Met Pro Lys Gly Lys Ser His Lys Pro Phe Arg Val Lys Lys
    1730              1735              1740
Ile Met Asp Gln Val Gln Gln Ala Ser Ala Ser Ser Ser Ala Pro Asn
1745              1750              1755              1760
Lys Asn Gln Leu Asp Gly Lys Lys Lys Lys Pro Thr Ser Pro Val Lys
                1765              1770              1775
Pro Ile Pro Gln Asn Thr Glu Tyr Arg Thr Arg Val Arg Lys Asn Ala
            1780              1785              1790
Asp Ser Lys Asn Asn Leu Asn Ala Glu Arg Val Phe Ser Asp Asn Lys
            1795              1800              1805
Asp Ser Lys Lys Gln Asn Leu Lys Asn Asn Ser Lys Asp Phe Asn Asp
    1810              1815              1820
Lys Leu Pro Asn Asn Glu Asp Arg Val Arg Gly Ser Phe Ala Phe Asp
1825              1830              1835              1840
Ser Pro His His Tyr Thr Pro Ile Glu Gly Thr Pro Tyr Cys Phe Ser
                1845              1850              1855
Arg Asn Asp Ser Leu Ser Ser Leu Asp Phe Asp Asp Asp Val Asp
            1860              1865              1870
Leu Ser Arg Glu Lys Ala Glu Leu Arg Lys Ala Lys Glu Asn Lys Glu
    1875              1880              1885
Ser Glu Ala Lys Val Thr Ser His Thr Glu Leu Thr Ser Asn Gln Gln
    1890              1895              1900
Ser Ala Asn Lys Thr Gln Ala Ile Ala Lys Gln Pro Ile Asn Arg Gly
1905              1910              1915              1920
Gln Pro Lys Pro Ile Leu Gln Lys Gln Ser Thr Phe Pro Gln Ser Ser
                1925              1930              1935
Lys Asp Ile Pro Asp Arg Gly Ala Ala Thr Asp Glu Lys Leu Gln Asn
            1940              1945              1950
Phe Ala Ile Glu Asn Thr Pro Val Cys Phe Ser His Asn Ser Ser Leu
    1955              1960              1965
Ser Ser Leu Ser Asp Ile Asp Gln Glu Asn Asn Asn Lys Glu Asn Glu
    1970              1975              1980
Pro Ile Lys Glu Thr Glu Pro Pro Asp Ser Gln Gly Glu Pro Ser Lys
1985              1990              1995              2000
Pro Gln Ala Ser Gly Tyr Ala Pro Lys Ser Phe His Val Glu Asp Thr
```

-continued

```
                    2005                        2010                        2015
Pro Val Cys Phe Ser Arg Asn Ser Ser Leu Ser Ser Leu Ser Ile Asp
            2020                        2025                    2030

Ser Glu Asp Asp Leu Leu Gln Glu Cys Ile Ser Ser Ala Met Pro Lys
        2035                        2040                    2045

Lys Lys Lys Pro Ser Arg Leu Lys Gly Asp Asn Glu Lys His Ser Pro
    2050                        2055                    2060

Arg Asn Met Gly Gly Ile Leu Gly Glu Asp Leu Thr Leu Asp Leu Lys
2065                        2070                    2075                2080

Asp Ile Gln Arg Pro Asp Ser Glu His Gly Leu Ser Pro Asp Ser Glu
                    2085                    2090                    2095

Asn Phe Asp Trp Lys Ala Ile Gln Glu Gly Ala Asn Ser Ile Val Ser
                2100                    2105                    2110

Ser Leu His Gln Ala Ala Ala Ala Ala Cys Leu Ser Arg Gln Ala Ser
            2115                    2120                        2125

Ser Asp Ser Asp Ser Ile Leu Ser Leu Lys Ser Gly Ile Ser Leu Gly
        2130                        2135                    2140

Ser Pro Phe His Leu Thr Pro Asp Gln Glu Glu Lys Pro Phe Thr Ser
2145                        2150                        2155                2160

Asn Lys Gly Pro Arg Ile Leu Lys Pro Gly Glu Lys Ser Thr Leu Glu
                    2165                    2170                    2175

Thr Lys Lys Ile Glu Ser Glu Ser Lys Gly Ile Lys Gly Gly Lys Lys
                2180                    2185                        2190

Val Tyr Lys Ser Leu Ile Thr Gly Lys Val Arg Ser Asn Ser Glu Ile
            2195                    2200                    2205

Ser Gly Gln Met Lys Gln Pro Leu Gln Ala Asn Met Pro Ser Ile Ser
2210                        2215                    2220

Arg Gly Arg Thr Met Ile His Ile Pro Gly Val Arg Asn Ser Ser Ser
2225                    2230                    2235                        2240

Ser Thr Ser Pro Val Ser Lys Lys Gly Pro Pro Leu Lys Thr Pro Ala
                2245                        2250                    2255

Ser Lys Ser Pro Ser Glu Gly Gln Thr Ala Thr Thr Ser Pro Arg Gly
            2260                        2265                    2270

Ala Lys Pro Ser Val Lys Ser Glu Leu Ser Pro Val Ala Arg Gln Thr
        2275                        2280                    2285

Ser Gln Ile Gly Gly Ser Ser Lys Ala Pro Ser Arg Ser Gly Ser Arg
    2290                        2295                    2300

Asp Ser Thr Pro Ser Arg Pro Ala Gln Gln Pro Leu Ser Arg Pro Ile
2305                    2310                    2315                        2320

Gln Ser Pro Gly Arg Asn Ser Ile Ser Pro Gly Arg Asn Gly Ile Ser
                    2325                    2330                    2335

Pro Pro Asn Lys Leu Ser Gln Leu Pro Arg Thr Ser Ser Pro Ser Thr
            2340                        2345                    2350

Ala Ser Thr Lys Ser Ser Gly Ser Gly Lys Met Ser Tyr Thr Ser Pro
        2355                        2360                    2365

Gly Arg Gln Met Ser Gln Gln Asn Leu Thr Lys Gln Thr Gly Leu Ser
    2370                        2375                        2380

Lys Asn Ala Ser Ser Ile Pro Arg Ser Glu Ser Ala Ser Lys Gly Leu
2385                        2390                    2395                    2400

Asn Gln Met Asn Asn Gly Asn Gly Ala Asn Lys Lys Val Glu Leu Ser
                        2405                    2410                    2415

Arg Met Ser Ser Thr Lys Ser Ser Gly Ser Glu Ser Asp Arg Ser Glu
                2420                        2425                    2430

Arg Pro Val Leu Val Arg Gln Ser Thr Phe Ile Lys Glu Ala Pro Ser
            2435                        2440                    2445
```

```
Pro Thr Leu Arg Arg Lys Leu Glu Glu Ser Ala Ser Phe Glu Ser Leu
    2450                2455                2460

Ser Pro Ser Ser Arg Pro Ala Ser Pro Thr Arg Ser Gln Ala Gln Thr
2465                2470                2475                2480

Pro Val Leu Ser Pro Ser Leu Pro Asp Met Ser Leu Ser Thr His Ser
                2485                2490                2495

Ser Val Gln Ala Gly Gly Trp Arg Lys Leu Pro Pro Asn Leu Ser Pro
            2500                2505                2510

Thr Ile Glu Tyr Asn Asp Gly Arg Pro Ala Lys Arg His Asp Ile Ala
        2515                2520                2525

Arg Ser His Ser Glu Ser Pro Ser Arg Leu Pro Ile Asn Arg Ser Gly
    2530                2535                2540

Thr Trp Lys Arg Glu His Ser Lys His Ser Ser Leu Pro Arg Val
2545.               2550                2555                2560

Ser Thr Trp Arg Arg Thr Gly Ser Ser Ser Ile Leu Ser Ala Ser
                2565                2570                2575

Ser Glu Ser Ser Glu Lys Ala Lys Ser Glu Asp Glu Lys His Val Asn
            2580                2585                2590

Ser Ile Ser Gly Thr Lys Gln Ser Lys Glu Asn Gln Val Ser Ala Lys
        2595                2600                2605

Gly Thr Trp Arg Lys Ile Lys Glu Asn Glu Phe Ser Pro Thr Asn Ser
    2610                2615                2620

Thr Ser Gln Thr Val Ser Ser Gly Ala Thr Asn Gly Ala Glu Ser Lys
2625                2630                2635                2640

Thr Leu Ile Tyr Gln Met Ala Pro Ala Val Ser Lys Thr Glu Asp Val
                2645                2650                2655

Trp Val Arg Ile Glu Asp Cys Pro Ile Asn Asn Pro Arg Ser Gly Arg
                2660                2665                2670

Ser Pro Thr Gly Asn Thr Pro Pro Val Ile Asp Ser Val Ser Glu Lys
            2675                2680                2685

Ala Asn Pro Asn Ile Lys Asp Ser Lys Asp Asn Gln Ala Lys Gln Asn
        2690                2695                2700

Val Gly Asn Gly Ser Val Pro Met Arg Thr Val Gly Leu Glu Asn Arg
2705                2710                2715                2720

Leu Asn Ser Phe Ile Gln Val Asp Ala Pro Asp Gln Lys Gly Thr Glu
                2725                2730                2735

Ile Lys Pro Gly Gln Asn Asn Pro Val Pro Val Ser Glu Thr Asn Glu
            2740                2745                2750

Ser Ser Ile Val Glu Arg Thr Pro Phe Ser Ser Ser Ser Ser Ser Lys
    2755                2760                2765

His Ser Ser Pro Ser Gly Thr Val Ala Ala Arg Val Thr Pro Phe Asn
    2770                2775                2780

Tyr Asn Pro Ser Pro Arg Lys Ser Ser Ala Asp Ser Thr Ser Ala Arg
2785                2790                2795                2800

Pro Ser Gln Ile Pro Thr Pro Val Asn Asn Asn Thr Lys Lys Arg Asp
            2805                2810                2815

Ser Lys Thr Asp Ser Thr Glu Ser Ser Gly Thr Gln Ser Pro Lys Arg
        2820                2825                2830

His Ser Gly Ser Tyr Leu Val Thr Ser Val
    2835                2840
```

( 2 ) INFORMATION FOR SEQ ID NO:8:

( i ) SEQUENCE CHARACTERISTICS:
        ( A ) LENGTH: 31 amino acids
        ( B ) TYPE: amino acid ( C ) STRANDEDNESS: single
( D ) TOPOLOGY: linear ( i i ) MOLECULE TYPE: peptide ( v i i ) IMMEDIATE SOURCE:
    ( B ) CLONE: ral2(yeast)

( x i ) SEQUENCE DESCRIPTION: SEQ ID NO:8:

```
Leu Thr Gly Ala Lys Gly Leu Gln Leu Arg Ala Leu Arg Arg Ile Ala
1               5                   10                  15

Arg Ile Glu Gln Gly Gly Thr Ala Ile Ser Pro Thr Ser Pro Leu
            20                  25                  30
```

( 2 ) INFORMATION FOR SEQ ID NO:9:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Homo sapiens ( v i i ) IMMEDIATE SOURCE:
    ( B ) CLONE: m3(mAChR)

( x i ) SEQUENCE DESCRIPTION: SEQ ID NO:9:

```
Leu Tyr Trp Arg Ile Tyr Lys Glu Thr Glu Lys Arg Thr Lys Glu Leu
1               5                   10                  15

Ala Gly Leu Gln Ala Ser Gly Thr Glu Ala Glu Thr Glu
            20                  25
```

( 2 ) INFORMATION FOR SEQ ID NO:10:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Homo sapiens ( v i i ) IMMEDIATE SOURCE:
    ( B ) CLONE: MCC ( x i ) SEQUENCE DESCRIPTION: SEQ ID NO:10:

```
Leu Tyr Pro Asn Leu Ala Glu Glu Arg Ser Arg Trp Glu Lys Glu Leu
1               5                   10                  15

Ala Gly Leu Arg Glu Glu Asn Glu Ser Leu Thr Ala Met
            20                  25
```

( 2 ) INFORMATION FOR SEQ ID NO:11:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:11:

GTATCAAGAC TGTGACTTTT AATTGTAGTT TATCCATTTT  40

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:12:

TTTAGAATTT CATGTTAATA TATTGTGTTC TTTTTAACAG  40

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:13:

GTAGATTTTA AAAGGTGTT TTAAATAAT TTTTAAGCT  40

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:14:

AAGCAATTGT TGTATAAAAA CTTGTTTCTA TTTTATTTAG  40

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:15:

GTAACTTTTC TTCATATAGT AAACATTGCC TTGTGTACTC  40

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:16:

NNNNNNNNN NNNGTCCCTT TTTTAAAAA AAAAAAATAG     40

( 2 ) INFORMATION FOR SEQ ID NO:17:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:17:

GTAAGTAACT TGGCAGTACA ACTTATTTGA AACTTTAATA     40

( 2 ) INFORMATION FOR SEQ ID NO:18:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:18:

ATACAAGATA TTGATACTTT TTTATTATTT GTGGTTTTAG     40

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:19:

GTAAGTTACT TGTTTCTAAG TGATAAAACA GYGAAGAGCT     40

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:20:

AATAAAAACA TAACTAATTA GGTTTCTTGT TTTATTTTAG     40

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:21:

GTTAGTAAAT TSCCTTTTTT GTTTGTGGGT ATAAAAATAG     40

( 2 ) INFORMATION FOR SEQ ID NO:22:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:22:

ACCATTTTTG CATGTACTGA TGTTAACTCC ATCTTAACAG     40

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:23:

GTAAATAAAT TATTTTATCA TATTTTTAA AATTATTTAA     40

( 2 ) INFORMATION FOR SEQ ID NO:24:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:24:

CATGATGTTA TCTGTATTTA CCTATAGTCT AAATTATACC ATCTATAATG TGCTTAATTT     60

TTAG     64

( 2 ) INFORMATION FOR SEQ ID NO:25:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:25:

| GTAACAGAAG | ATTACAAACC | CTGGTCACTA | ATGCCATGAC | TACTTTGCTA | AG | 52 |

( 2 ) INFORMATION FOR SEQ ID NO:26:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:26:

| GGATATTAAA | GTCGTAATTT | TGTTTCTAAA | CTCATTTGGC | CCACAG | 46 |

( 2 ) INFORMATION FOR SEQ ID NO:27:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:27:

| GTATGTTCTC | TATAGTGTAC | ATCGTAGTGC | ATGTTTCAAA | 40 |

( 2 ) INFORMATION FOR SEQ ID NO:28:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:28:

| CATCATTGCT | CTTCAAATAA | CAAAGCATTA | TGGTTTATGT | TGATTTATT | TTTCAG | 56 |

( 2 ) INFORMATION FOR SEQ ID NO:29:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:29:

| GTAAGACAAA | AATGTTTTTT | AATGACATAG | ACAATTACTG | GTG | 43 |

( 2 ) INFORMATION FOR SEQ ID NO:30:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:30:

TTAGATGATT GTCTTTTCC TCTTGCCCTT TTTAAATTAG    40

( 2 ) INFORMATION FOR SEQ ID NO:31:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:31:

GTATGTTTTT ATAACATGTA TTTCTTAAGA TAGCTCAGGT ATGA    44

( 2 ) INFORMATION FOR SEQ ID NO:32:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:32:

GCTTGGCTTC AAGTTGNCTT TTTAATGATC CTCTATTCTG TATTTAATTT ACAG    54

( 2 ) INFORMATION FOR SEQ ID NO:33:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:33:

GTACTATTTA GAATTTCACC TGTTTTTCTT TTTTCTCTTT TTCTTTGAGG CAGGGTCTCA    60

CTCTG    65

( 2 ) INFORMATION FOR SEQ ID NO:34:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:34:

GCAACTAGTA TGATTTTATG TATAAATTAA TCTAAAATTG ATTAATTTCC AG     52

( 2 ) INFORMATION FOR SEQ ID NO:35:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:35:

GTACCTTTGA AAACATTTAG TACTATAATA TGAATTTCAT GT     42

( 2 ) INFORMATION FOR SEQ ID NO:36:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:36:

CCAACTCNAA TTAGATGACC CATATTCAGA AACTTACTAG     40

( 2 ) INFORMATION FOR SEQ ID NO:37:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:37:

GTATATATAG AGTTTTATAT TACTTTTAAA GTACAGAATT CATACTCTCA AAAA     54

( 2 ) INFORMATION FOR SEQ ID NO:38:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:38:

ATTGTGACCT TAATTTGTG ATCTCTTGAT TTTTATTTCA G     41

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:39:

TCCCCGCCTG CCGCTCTC	18

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:40:

GCAGCGGCGG CTCCCGTG	18

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:41:

GTGAACGGCT CTCATGCTGC	20

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:42:

ACGTGCGGGG AGGAATGGA	19

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA (vi) ORIGINAL SOURCE:
    (A) ORGANISM: Homo sapiens (xi) SEQUENCE DESCRIPTION: SEQ ID NO:43:

ATGATATCTT ACCAAATGAT ATAC    24

(2) INFORMATION FOR SEQ ID NO:44:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:44:

TTATTCCTAC TTCTTCTATA CAG    23

(2) INFORMATION FOR SEQ ID NO:45:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:45:

TACCCATGCT GGCTCTTTTT C    21

(2) INFORMATION FOR SEQ ID NO:46:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:46:

TGGGGCCATC TTGTTCCTGA    20

(2) INFORMATION FOR SEQ ID NO:47:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:47:

ACATTAGGCA CAAAGCTTGC AA    22

(2) INFORMATION FOR SEQ ID NO:48:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:48:

ATCAAGCTCC AGTAAGAAGG TA   22

( 2 ) INFORMATION FOR SEQ ID NO:49:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:49:

TGCGGCTCCT GGGTTGTTG   19

( 2 ) INFORMATION FOR SEQ ID NO:50:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:50:

GCCCCTTCCT TTCTGAGGAC   20

( 2 ) INFORMATION FOR SEQ ID NO:51:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:51:

TTTTCTCCTG CCTCTTACTG C   21

( 2 ) INFORMATION FOR SEQ ID NO:52:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:

( A ) ORGANISM: Homo sapiens ( x i ) SEQUENCE DESCRIPTION: SEQ ID NO:52:

ATGACACCCC CCATTCCCTC                    20

( 2 ) INFORMATION FOR SEQ ID NO:53:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:53:

CCACTTAAAG CACATATATT TAGT               24

( 2 ) INFORMATION FOR SEQ ID NO:54:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:54:

GTATGGAAAA TAGTGAAGAA CC                 22

( 2 ) INFORMATION FOR SEQ ID NO:55:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:55:

TTCTTAAGTC CTGTTTTTCT TTTG               24

( 2 ) INFORMATION FOR SEQ ID NO:56:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:56:

TTTAGAACCT TTTTGTGTT GTG                 23

( 2 ) INFORMATION FOR SEQ ID NO:57:

( i ) SEQUENCE CHARACTERISTICS:

(A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:57:

CTCAGATTAT ACACTAAGCC TAAC                                          24

(2) INFORMATION FOR SEQ ID NO:58:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:58:

CATGTCTCTT ACAGTAGTAC CA                                            22

(2) INFORMATION FOR SEQ ID NO:59:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:59:

AGGTCCAAGG GTAGCCAAGG                                               20

(2) INFORMATION FOR SEQ ID NO:60:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO:60:

TAAAAATGGA TAAACTACAA TTAAAAG                                       27

(2) INFORMATION FOR SEQ ID NO:61:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens ( x i ) SEQUENCE DESCRIPTION: SEQ ID NO:61:

AAATACAGAA TCATGTCTTG AAGT 24

( 2 ) INFORMATION FOR SEQ ID NO:62:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:62:

ACACCTAAAG ATGACAATTT GAG 23

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:63:

TAACTTAGAT AGCAGTAATT TCCC 24

( 2 ) INFORMATION FOR SEQ ID NO:64:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:64:

ACAATAAACT GGAGTACACA AGG 23

( 2 ) INFORMATION FOR SEQ ID NO:65:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:65:

ATAGGTCATT GCTTCTTGCT GAT 23

( 2 ) INFORMATION FOR SEQ ID NO:66:

( i ) SEQUENCE CHARACTERISTICS:
        ( A ) LENGTH: 24 base pairs
        ( B ) TYPE: nucleic acid ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:66:

TGAATTTTAA TGGATTACCT AGGT 24

( 2 ) INFORMATION FOR SEQ ID NO:67:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:67:

CTTTTTTGC TTTTACTGAT TAACG 25

( 2 ) INFORMATION FOR SEQ ID NO:68:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:68:

TGTAATTCAT TTTATTCCTA ATAGCTC 27

( 2 ) INFORMATION FOR SEQ ID NO:69:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:69:

GGTAGCCATA GTATGATTAT TTCT 24

( 2 ) INFORMATION FOR SEQ ID NO:70:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:70:

CTACCTATTT TTATACCCAC AAAC 24

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:71:

AAGAAAGCCT ACACCATTTT TGC 23

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:72:

GATCATTCTT AGAACCATCT TGC 23

(2) INFORMATION FOR SEQ ID NO:73:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:73:

ACCTATAGTC TAAATTATAC CATC 24

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:74:

GTCATGGCAT TAGTGACCAG 20

(2) INFORMATION FOR SEQ ID NO:75:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:75:

AGTCGTAATT TTGTTTCTAA ACTC 24

(2) INFORMATION FOR SEQ ID NO:76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:76:

TGAAGGACTC GGATTTCACG C 21

(2) INFORMATION FOR SEQ ID NO:77:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:77:

TCATTCACTC ACAGCCTGAT GAC 23

(2) INFORMATION FOR SEQ ID NO:78:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:78:

GCTTTGAAAC ATGCACTACG AT 22

(2) INFORMATION FOR SEQ ID NO:79:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:79:

AAACATCATT GCTCTTCAAA TAAC 24

( 2 ) INFORMATION FOR SEQ ID NO:80:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:80:

TACCATGATT TAAAAATCCA CCAG        24

( 2 ) INFORMATION FOR SEQ ID NO:81:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:81:

GATGATTGTC TTTTTCCTCT TGC        23

( 2 ) INFORMATION FOR SEQ ID NO:82:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:82:

CTGAGCTATC TTAAGAAATA CATG        24

( 2 ) INFORMATION FOR SEQ ID NO:83:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:83:

TTTTAAATGA TCCTCTATTC TGTAT        25

( 2 ) INFORMATION FOR SEQ ID NO:84:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA (vi) ORIGINAL SOURCE:
    (A) ORGANISM: Homo sapiens (xi) SEQUENCE DESCRIPTION: SEQ ID NO:84:

ACAGAGTCAG ACCCTGCCTC AAAG                                                      24

(2) INFORMATION FOR SEQ ID NO:85:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:85:

TTTCTATTCT TACTGCTAGC ATT                                                       23

(2) INFORMATION FOR SEQ ID NO:86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:86:

ATACACAGGT AAGAAATTAG GA                                                        22

(2) INFORMATION FOR SEQ ID NO:87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:87:

TAGATGACCC ATATTCTGTT TC                                                        22

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:88:

CAATTAGGTC TTTTTGAGAG TA                                                        22

(2) INFORMATION FOR SEQ ID NO:89:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:89:

GTTACTGCAT ACACATTGTG AC 22

( 2 ) INFORMATION FOR SEQ ID NO:90:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:90:

GCTTTTTGTT TCCTAACATG AAG 23

( 2 ) INFORMATION FOR SEQ ID NO:91:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:91:

TCTCCCACAG GTAATACTCC C 21

( 2 ) INFORMATION FOR SEQ ID NO:92:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:92:

GCTAGAACTG AATGGGGTAC G 21

( 2 ) INFORMATION FOR SEQ ID NO:93:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:

( A ) ORGANISM: Homo sapiens ( x i ) SEQUENCE DESCRIPTION: SEQ ID NO:93:

CAGGACAAAA TAATCCTGTC CC 22

( 2 ) INFORMATION FOR SEQ ID NO:94:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:94:

ATTTTCTTAG TTTCATTCTT CCTC 24

TABLE I

APC EXONS

| EXON NUCLEOTIDES[1] | EXON BOUNDARY SEQUENCE[2] |
|---|---|
| 822 to 930 | catgatgttatctgtatttacctatagtctaaattataccatctataatgtgcttaatttttag/GGTTCA ... <br> ... ACCAAG/gtaacagaagattacaaaccctggtcactaatgccatgactactttgctaag |
| 931 to 1309 | ggatattaaagtcgtaattttgtttctaaactcatttggcccacag/GTGGAA ... <br> ... ATCCAA/gtatgttctctatagtgtacatcgtagtgcatg |
| 1310 to 1405 | catcattgctcttcaaataacaaagcattatggtttatgttgattttattttcag/TGCCAG ... <br> ... AACTAG/gtaagacaaaaatgtttttaatgacatagacaattactggtg |
| 1406 to 1545 | tagatgattgtcttttccctcttgcccttttaaattag/GGGGAC ... <br> ... AACAAG/gtatgttttataacatgtatttcttaagatagctcggtatga |
| 1546 to 1623 | gcttggcttcaagttgtcttttaatgatcctctattctgtatttaatttacag/GCTACG ... <br> ... CAGAGAG/gtactatttagaatttcacctgttttcttttttctcttttctttgaggcagggtctcactctg |
| 1624 to 1740 | gcaactagtatgatttatgtataaataattctaaaattgattaatttgcag/GTTATT ... <br> ... AAAAAG/gtaccttttgaaaacatttagtactataatatgaatttcatgt |
| 1741 to 1955 | caactctaattagatgacccatattcagaaaacttactag/GAATCA ... <br> ... CCACAG/gtatatatagagtttttatattactttttaaagtacagaattcatactctcaaaa |
| 1956 to 8973 | tcttgattttattttcag/GCAAAT ... <br> ... GGTATTTATGCAAAAAAAAATGTTTTTGT |

[1]Relative to predicted translation initiation site
[2]Small case letters represent introns, large case letters represent exons
[3]The entire 3' end of the cloned APC cDNA (nt 1956-8973) appeared to be encoded in this exon, as indicated by restriction endonuclease mapping and sequencing of cloned genomic DNA. The ORF ended at nt 8535. The extreme 3' end of the APC transcript has not yet been identified.

TABLE IIA

Germline mutations of the APC gene in FAP and GS Patients

| Patient | Codon | Nucleotide Change | Amino Acid Change | Age | Extra-colonic Disease |
|---|---|---|---|---|---|
| 93 | 279 | TCA→TGA | Ser→Stop | 39 | Mandibular Osteoma |
| 24 | 301 | CGA→TGA | Arg→Stop | 46 | None |
| 34 | 301 | CGA→TGA | Arg→Stop | 27 | Desmoid Tumor |
| 21 | 413 | CGC→TGC | Arg→Cys | 24 | Mandibular Osteoma |
| 60 | 712 | TCA→TGA | Ser→Stop | 37 | Mandibular Osteoma |
| 3746 | 243 | CAGAG→CAG | splice-junction | | |
| 3460 | 301 | CGA→TGA | Arg→stop | | |
| 3827 | 456 | CTTTCA→CTT | frameshift | | |
| 3712 | 500 | CA T→G | Tyr→Stop | | |

*The mutated nucleotides are underlined.

TABLE IIB

Somatic Mutations in Sporadic CRC Patients

| PATIENT | CODON[1] | NUCLEOTIDE CHANGE | AMINO ACID CHANGE |
|---|---|---|---|
| T35 | MCC 12 | GAG/gtaaga→ | (Splice |

TABLE IIB-continued

Somatic Mutations in Sporadic CRC Patients

| PATIENT | CODON[1] | NUCLEOTIDE CHANGE | AMINO ACID CHANGE |
|---|---|---|---|
| T16 | MCC 145 | GAG/gtaaaa ctcag/GGA→ atcag/GGA | Donor) (Splice Acceptor) |
| T47 | MCC 267 | CGG→C<u>T</u>G | Arg→Leu |
| T81 | MCC 490 | TCG→T<u>T</u>G | Ser→Leu |
| T35 | MCC 506 | CGG→CA<u>G</u> | Arg→Gln |
| T91 | MCC 698 | GCT→G<u>T</u>T | Ala→Val |
| T34 | APC 288 | CCAGT→CC<u>CAGC</u>CAGT | (Insertion) |
| T27 | APC 331 | CGA→<u>T</u>GA | Arg→Stop |
| T135 | APC 437 | CAA/gtaa→CAA/g<u>c</u>aa | (Splice Donor) |
| T201 | APC 1338 | CAG→<u>T</u>AG | Gln→Stop |

[1] For splice site mutations, the codon nearest to the mutation is listed
The underlined nucleotides were mutant; small case letters represent introns, large case letters represent exons

TABLE III

Sequences of Primers Used for SSCP Analyses

| Exon | Primer 1 | Primer 2 |
|---|---|---|
| DP1 | | |
| | UP-TCCCCGCCTGCCGCTCTC | RP-GCAGCGGCGGCTCCCGTG |
| | UP-GTGAACGGCTCTCATGCTGC | RP-ACGTGCGGGGAGGAATGGA |
| | UP-ATGATATCTTACCAAATGATATAC | RP-TTATTCCTACTTCTTCTATACAG |
| | UP-TACCCATGCTGGCTCTTTTTC | RP-TGGGGCCATCTTGTTCCTGA |
| | UP-ACATTAGGCACAAAGCTTGCAA | RP-ATCAAGCTCCAGTAAGAAGGTA |
| SRP19 | | |
| | UP-TGCGGCTCCTGGGTTGTTG | RP-GCCCCTTCCTTTCTGAGGAC |
| | UP-TTTTCTCCTGCCTCTTACTGC | RP-ATGACACCCCCCATTCCCTC |
| | UP-CCACTTAAAGCACATATATTTAGT | RP-GTATGGAAAATAGTGAAGAACC |
| | UP-TTCTTAAGTCCTGTTTTTCTTTTG | RP-TTTAGAACCTTTTTTGTGTTGTG |
| | UP-CTCAGATTATACACTAAGCCTAAC | RP-CATGTCTCTTACAGTAGTACCA |
| DP2.5 | | |
| | UP-AGGTCCAAGGGTAGCCAAGG* | RP-TAAAAATGGATAAACTACAATTAAAAG |
| | UP-AAATACAGAATCATGTCTTGAAGT | RP-ACACCTAAAGATGACAATTTGAG |
| | UP-TAACTTAGATAGCAGTAATTTCCC* | RP-ACAATAAACTGGAGTACACAAGG |
| | UP-ATAGGTCATTGCTTCTTGCTGAT* | RP-TGAATTTTAATGGATTACCTAGGT |
| | UP-CTTTTTTTGCTTTTACTGATTAACG | RP-TGTAATTCATTTTATTCCTAATACCTC |
| | UP-GGTAGCCATAGTATGATTATTTCT | RP-CTACCTATTTTTATACCCACAAAC |
| | UP-AAGAAAGCCTACACCATTTTTGC | RP-GATCATTCTTAGAACCATCTTGC |
| | UP-ACCTATAGTCTAAATTATACCATC | RP-GTCATGGCATTACTGACCAG |
| | UP-AGTCGTAATTTTGTTTCTAAACTC | RP-TGAAGGACTCCGATTTCACCC* |
| | UP-TCATTCACTCACAGCCTGATGAC* | RP-GCTTTGAAACATGCACTACGAT |
| | UP-AAACATCATTGCTCTTCAAATAAC | RP-TACCATGATTTAAAAATCCACCAG |
| | UP-GATGATTGTCTTTTTCCTCTTGC | RP-CTGAGCTATCTTAAGAAATACATG |
| | UP-TTTTAAATGATCCTCTATTCTGTAT | RP-ACAGAGTCAGACCCTCCCTCAAAG |
| | UP-TTTCTATTCTTACTGCTAGCATT | RP-ATACACAGGTAAGAAATTAGGA |
| | UP-TAGATGACCCATATTCTCTTTC | RP-CAATTAGGTCTTTTTGAGAGTA |
| 3-A | UP-GTTACTGCATACACATTGTGAC | RP-GCTTTTTGTTTCGTAACATGAAG* |
| -B | UP-AGTACAAGGATGCCAATTTATG* | RP-ACTTCTATCTTTTTCAGAACGAG* |
| -C | UP-ATTTGAATACTACAGTGTTACCC* | RP-CTTGTATTCTAATTTGGCATAAGG* |
| -D | UP-CTGCCCATACACATTCAAACAC* | RP-TGTTTGCGTCTTGCCCATCTT* |
| -E | UP-AGTCTTAAATATTCAGATGAGCAG* | RP-GTTTCTCTTCATTATATTTTATGCTA* |
| -F | UP-AAGCCTACCAATTATAGTGAACG* | RP-AGCTGATGACAAAGATGATAATC* |
| -G | UP-AAGAAACAATACAGACTTATTGTG* | RP-ATGAGTGGGGTCTCCTGAAC* |
| -H | UPATCTCCCTCCAAAAGTGGTGC* | RP-TCCATCTGGGAGTACTTTCTGTG* |
| -I | UP-AGTAAATGCTGCAGTTCAGAGG* | RP-CCGTGGCATATCATCCCCC* |
| -J | UP-CCCAGACTGCTTCAAAATTACC* | RP-GAGCCTCATCTGTACTTCTGC* |
| -K | UP-CCCTCCAAATGATTAGCTGC* | RP-TTGTGGTATAGGTTTTACTGGTG* |
| -L | UP-ACCCAACAAAAATCAGTTAGATG* | RP-GTGGCTGGTAACTTTAGCCTC* |
| -N | UP-ATGATGTTGACCTTTCCAGGG* | RP-ATTGTGTAACTTTTCATCAGTTGC* |
| -M | UP-AAAGACATACCAGACAGAGGG* | RP-CTTTTTTGGCATTGCGGAGCT* |
| -O | UP-AAGATGACCTGTTGCAGGAATG* | RP-GAATCAGACCAAGCTTGTCTAGAT* |
| -P | UP-CAATAGTAAGTAGTTTACATCAAG* | RP-AAACAGGACTTGTACTGTAGGA* |
| -Q | UP-CAGCCCCTTCAAGCAAACATC* | RP-GAGGACTTATTCCATTTCTACC* |
| -R | UP-CAGTCTCCTGGCCGAAACTC* | RP-GTTGACTGGCGTACTAATACAG* |
| -S | UP-TGGTAATGGAGCCAATAAAAAGG* | RP-TGGGACTTTTCGCCATCCAC* |
| -T | UP-TGTCTCTATCCACACATTCGTC* | RP-ATGTTTTTCATCCTCACTTTTTGC* |
| -U | UP-GGAGAAGAACTGGAAGTTCATC* | RP-TTGAATCTTTAATGTTTGGATTTGC* |
| -V | UP-TCTCCCACAGGTAATACTCCC | RP-GCTACAACTGAATGGGGTACG |
| -W | UP-CAGGACAAAATAATCCTGTCCC | RP-ATTTTCTTACTTTCATTCTTCCTC |

All primers are read in the 5' to 3' direction. the first primer in each pair lies 5' of the exon it amplifies; the second primer lies 3' of the exon it amplifies. Primers that lie within the exon are identified by an asterisk. UP represents the - 21M13 universal primer sequence: RP represents the M13 reverse primer sequence.

TABLE IV

Seven Different Versions of the 20-Amino Acid Repeat

| Consensus: | F | . | V | E | . | T | P | . | C | F | S | R | . | S | S | L | S | S | L | S |
|---|---|---|---|---|---|---|---|---|---|---|---|---|---|---|---|---|---|---|---|---|
| 1262: | Y | C | V | E | D | T | P | I | C | F | S | R | C | S | S | L | S | S | L | S |
| 1376: | H | Y | V | Q | E | T | P | L | M | F | S | R | C | T | S | V | S | S | L | D |
| 1492: | F | A | T | E | S | T | P | D | G | F | S | C | S | S | S | L | S | A | L | S |

TABLE IV-continued

| | Seven Different Versions of the 20-Amino Acid Repeat | | | | | | | | | | | | | | | | | | | |
|---|---|---|---|---|---|---|---|---|---|---|---|---|---|---|---|---|---|---|---|---|
| Consensus: | F | . | V | E | . | T | P | . | C | F | S | R | . | S | S | L | S | S | L | S |
| 1643: | Y | C | V | E | G | T | P | I | N | F | S | T | A | T | S | L | S | D | L | T |
| 1848: | T | P | I | E | G | T | P | Y | C | F | S | R | N | D | S | L | S | S | L | D |
| 1953: | F | A | I | E | N | T | P | V | C | P | S | H | N | S | S | L | S | S | L | S |
| 2013: | F | H | V | E | D | T | P | V | C | F | S | R | N | S | S | L | S | S | L | S |

Numbers denote the first amino acid of each repeat. The consensus sequence at the top relfects a majority amino acid at a given position.

We claim:

1. A cDNA molecule having the nucleotide sequence shown in SEQ ID NO: 1 or its complement.

2. An isolated DNA molecule having the nucleotide sequence shown in SEQ ID NO:1 or its complement.

3. A cDNA molecule which encodes a protein having the amino acid sequence shown in FIG. 3 or 7 (SEQ ID NO: 7 or 2).

4. An isolated DNA molecule which encodes a protein having the amino acid sequence shown in FIG. 3 or 7 (SEQ ID NO: 7 or 2).

5. A nucleic acid probe complementary to all or part of human wild-type APC gene coding sequences or the complement of said sequence such that said probe selectively hybridizes under stringent conditions to said APC gene or identifies endogenous, random modifications in said APC gene.

6. The nucleic acid probe of claim 5 which hybridizes to all or part of an exon selected from the group consisting of: (1) nucleotides 822 to 930; (2) nucleotides 931 to 1309; (3) nucleotides 1406 to 1545; and (4) nucleotides 1956 to 2256.

7. A set of probes useful for detecting alteration of wild-type APC genes comprising a plurality of nucleic acid probes wherein said set is complementary to all nucleotides of the APC gene coding sequences as shown in SEQ ID NO:1 or the complement of said sequences.

8. A pair of signal stranded DNA primers for determination of a nucleotide sequence of an APC gene by polymerase chain reaction, the sequence of said primers being derived from said APC gene, wherein the use of said primers in a polymerase chain reaction results in synthesis of DNA having all or part of the sequence shown in FIG. 7 (SEQ ID NO:1).

9. The pair of primers of claim 8 which have restriction enzyme sites at each 5' end.

10. The pair of primers of claim 9 having sequences complementary to all or part of one or more APC introns.

* * * * *

UNITED STATES PATENT AND TRADEMARK OFFICE
CERTIFICATE OF CORRECTION

PATENT NO. : 5,352,775
DATED : October 4, 1994
INVENTOR(S) : Hans Albertsen, et al It is certified that error appears in the above-indentified patent and that said Letters Patent is hereby corrected as shown below:

IN THE CLAIMS

In claim 5, column 127, line 25, please delete the word "sequence" and insert therefor --sequences--.

In claim 8, column 128, line 19, please delete the word "signal" and insert therefc --single--.

In claim 10, column 128, line 28, please delete the number "9" and insert therefor --8--

Signed and Sealed this

Tenth Day of September, 1996

Attest:

BRUCE LEHMAN

*Attesting Officer*     *Commissioner of Patents and Trademarks*